United States Patent [19]

Ratcliffe et al.

[11] Patent Number: 5,294,620
[45] Date of Patent: Mar. 15, 1994

[54] 1,6-NAPHTHYRIDINONE DERIVATIVES HAVING ANGIOTENSION II ANTAGONIST ACTIVITY

[75] Inventors: Arnold H. Ratcliffe, Poynton; Robert J. Pearce, Wilmslow; Keith H. Gibson, Macclesfield; Robin Wood, Stockport, all of England; Brian B. Masek, West Grove, Pa.

[73] Assignee: Imperial Chemical Industries PLC, London, England

[21] Appl. No.: 42,321

[22] Filed: Apr. 2, 1993

Related U.S. Application Data

[62] Division of Ser. No. 890,453, May 29, 1992, Pat. No. 5,217,976.

[30] Foreign Application Priority Data

May 31, 1991 [GB] United Kingdom ............ 9111759
Jul. 29, 1991 [GB] United Kingdom ............ 9116309

[51] Int. Cl.⁵ ............... A61K 31/435; C07D 471/04
[52] U.S. Cl. ............................. 514/300; 544/328; 546/122; 546/123
[58] Field of Search ............ 546/122, 123; 544/328; 514/300

[56] References Cited

U.S. PATENT DOCUMENTS

| | | | |
|---|---|---|---|
| 4,920,131 | 4/1990 | Huang et al. | 514/311 |
| 5,028,615 | 6/1991 | Huang et al. | 514/314 |
| 5,126,344 | 6/1992 | Roberts et al. | 514/248 |
| 5,130,318 | 7/1992 | Roberts et al. | 514/299 |
| 5,149,699 | 9/1992 | Ellingboe et al. | 514/258 |

FOREIGN PATENT DOCUMENTS

| | | |
|---|---|---|
| 0315399 | 5/1989 | European Pat. Off. |
| 0326328 | 8/1989 | European Pat. Off. |
| 0326330 | 8/1989 | European Pat. Off. |
| 0348155 | 12/1989 | European Pat. Off. |
| 0399731 | 11/1990 | European Pat. Off. |
| 0400974 | 12/1990 | European Pat. Off. |
| 0412848 | 2/1991 | European Pat. Off. |
| 0436333 | 7/1991 | European Pat. Off. |
| 0445811 | 9/1991 | European Pat. Off. |
| 0475206 | 3/1992 | European Pat. Off. |
| 0487745 | 6/1992 | European Pat. Off. |
| 498721 | 8/1992 | European Pat. Off. |
| 0500297 | 8/1992 | European Pat. Off. |
| 518033A1 | 12/1992 | European Pat. Off. |
| WO91/07404 | 5/1991 | PCT Int'l Appl. |
| 920577 | 3/1993 | South Africa . |

OTHER PUBLICATIONS

G. R. Proctor, et al., "Azabenzocycloheptenones. Part XIV. Cyyclisation of Amino-acid Derivatives to Tetrahydro-1-benzazepin-5-ones and Tetrahydroquiolin-4-ones" *J. Chem. Soc., Perkin Trans. I* (1972), 1803–08.

R. D. Youssefyeh, et al. (principal author Huang) *J. Med. Chem.* (1990), 33, 1186–1194; *Chem. Abst.* (1990), 112, 17, abstract 131,890u.

F. Huang *J. Med. Chem.* (1990), 33, 1194–1200.

F. Haglid, *Ark. Kemi* (1967), 26, 489–95; as Chem. Abstr. (1967), 67, 3084, abstract 32,611z.

*Primary Examiner*—Bernard Dentz
*Attorney, Agent, or Firm*—Thomas E. Jackson

[57] ABSTRACT

The invention concerns pharmaceutically useful compounds of the formula I, in which $R^1$, $R^2$, $R^3$, $R^4$, Ra, Rb, A, X and Z have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

10 Claims, No Drawings

1,6-NAPHTHYRIDINONE DERIVATIVES HAVING ANGIOTENSION II ANTAGONIST ACTIVITY

This is a divisional of co-pending application Ser. No. 07/890,453 filed on May 29, 1992 now U.S. Pat. No. 5,217,976.

This invention concerns novel heterocyclic derivatives and, more particularly, novel heterocyclic derivatives which possess pharmacologically useful properties in antagonising at least in part one or more of the actions of the substances known as angiotensins, and in particular of that known as angiotensin Ii (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) on angiotensin I, itself produced by the action of the enzyme renin on the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

In our co-pending European Patent Application (EPA), Publication No. 454831 there are described certain naphthyridine derivatives having AII antagonist activity.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a heterocyclic derivative of the formula I (set out hereinafter, together with the other chemical formulae identified by Roman numerals) wherein $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, (1-4C)alkoxy or phenyl substituent; $R^2$ is hydrogen, (1-4C)alkyl, (1-4C)alkoxy, halogeno, trifluoromethyl, carboxy, (1-4C)alkoxycarbonyl, (3-6C)alkenyloxycarbonyl, cyano, nitro, carbamoyl, (1-4C)alkanoyl, N-alkylcarbamoyl and di-(N-alkyl)carbamoyl of up to 7 carbon atoms, amino, alkylamino and dialkylamino of up to 6 carbon atoms, 3-(1-4C)alkylureido and (1-4C)alkanoylamino; $R^3$ is selected from halogeno, (1-4C)alkoxy, hydroxy, amino, alkylamino and dialkylamino of up to 6 carbon atoms, and any of the values defined for $R^1$; A is a linking group of the formula —CH=CH—CO—, —CO—CH=CH—, —CO—CH$_2$—CH$_2$—, —CH$_2$—CH$_2$—CO—, —CH$_2$—CO— or —CO—CH$_2$—; Ra and Rb are optional substituents on linking group A independently selected from (1-4C)alkyl, substituted (1-4C)alkyl containing one or more fluoro substituents or bearing a (3-8C)cycloalkyl, (1-4C)alkoxy or phenyl substituent, (3-8C)cycloalkyl, phenyl, pyridyl, (1-4C)alkoxy, halogeno, carboxy, (1-4C)alkoxycarbonyl, (3-6C)alkenyloxycarbonyl, carbamoyl, N-alkylcarbamoyl and di-(N-alkyl)carbamoyl of up to 7 carbon atoms, cyano, nitro, (1-4C)alkanoyl, (1-4C)alkylthio, (1-4C)alkylsulphinyl, (1-4C)alkylsulphonyl, phenylthio, phenylsulphinyl and phenylsulphonyl; $R^4$ is selected from hydrogen, (1-4C)alkyl, (1-4C)alkoxy, halogeno, trifluoromethyl, cyano and nitro; X is phenylene optionally bearing a substituent selected from (1-4C)alkyl, (1-4C)alkoxy, halogeno, (1-4C)alkanoyl, trifluoromethyl, cyano and nitro, or X is a direct bond between the adjacent phenyl and methylene groups; Z is 1H-tetrazol-5-yl, —CO.NH.(1H-tetrazol-5-yl), —NHSO$_2$CF$_3$ or a group of the formula —CO.OR$^5$, —CO.NH.SO$_2$.R$^6$ or —SO$_2$.NHR in which $R^5$ is hydrogen or a non-toxic, biodegradable residue of a physiologically acceptable alcohol or phenol, $R^6$ is (1-6C)alkyl, (3-8C)cycloalkyl or phenyl, and $R^7$ is hydrogen, (1-4C)alkyl, (1-4C)alkanoyl or —CO.NH.(1-4C)alkyl; or when X is a direct bond between the adjacent phenyl and methylene groups, Z is a 2-carboxybenzamido, 2-sulfobenzamido or 2-carboxybenzyloxy group, the benzene ring of which last three groups may optionally bear 1 or 2 additonal substituents independently selected from (1-4C)alkyl, (1-4C)alkoxy and halogeno; and wherein any of said phenyl moieties may be unsubstituted or bear one or two substituents independently selected from (1-4C)alkyl, (1-4C)alkoxy, halogeno, cyano and trifluoromethyl; or an N-oxide thereof; or a non-toxic salt thereof.

It will be appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It will also be appreciated that this invention includes those compounds of formula I in which the optional substituents Ra and Rb are attached to the same or different carbon atoms of linking group A where appropriate.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$ or $R^3$ when it is alkyl is, for example, (1–6C)alkyl such as methyl, ethyl, propyl, isopropyl, butyl, isobutyl, sec-butyl, pentyl or hexyl; and when it is cycloalkyl is, for example, cyclopropyl, cyclopentyl or cyclohexyl.

A particular value for $R^1$ or $R^3$ when it is alkyl containing one or more fluoro substituents is, for example, fluoromethyl, trifluoromethyl, 2,2,2-trifluoroethyl or pentafluoroethyl; and when it is alkyl bearing a cycloalkyl, (1–4C)alkoxy or phenyl substituent is, for example, cyclopropylmethyl, cyclopentylmethyl, cyclohexylmethyl, 2-methoxyethyl, 2-ethoxyethyl, benzyl, 1-phenylethyl or 2-phenylethyl.

A particular value for $R^2$ when it is alkyl is, for example, methyl, ethyl, propyl, isopropyl or butyl; when it is alkoxycarbonyl is, for example, methoxycarbonyl, ethoxycarbonyl or propoxycarbonyl; when it is alkenyloxycarbonyl is, for example, allyloxycarbonyl, 2-methyl-2-propenyloxycarbonyl or 3-methyl-3-butenyloxycarbonyl; and when it is alkanoyl is, for example, formyl, acetyl or propionyl.

Particular values for $R^2$ or $R^3$ are, by way of example, for alkylamino: methylamino, ethylamino or butylamino; for dialkylamino: dimethylamino, diethylamino or dipropylamino; for halogeno: fluoro, chloro, bromo or iodo; and for alkoxy: methoxy or ethoxy;

Particular values for $R^2$ include, by way of example, for N-alkylcarbamoyl: N-methyl and N-ethylcarbamoyl; for di(N-alkyl)carbamoyl: N,N-dimethylcarbamoyl and N,N-diethylcarbamoyl; for alkanoylamino: formamido, acetamido and propanamido; and for 3-alkylureido: 3-methylureido, 3-ethylureido and 3-propylureido Particular values for Ra or Rb include, by way of example, for alkyl: methyl, ethyl and propyl; for alkyl containing one or more fluoro substituents or bearing a cycloalkyl, alkoxy or phenyl substituent: fluoromethyl, trifluoromethyl, 2,2,2-trifluoroethyl and pentafluoroethyl, cyclopropylmethyl, cyclopentylmethyl, cyclohexylmethyl, 2-methoxyethyl, 2-ethoxyethyl, benzyl, 1-phenylethyl and 2-phenylethyl; for cycloalkyl: cyclopropyl, cyclopentyl and cyclohexyl; for alkoxy: methoxy and ethoxy; for halogeno: fluoro, chloro, bromo and iodo; for alkoxycarbonyl: methoxycarbonyl, ethoxycarbonyl and propoxycarbonyl; for alkenyloxycarbonyl: allyloxycarbonyl, 2-methyl-2-propenyloxycarbonyl and 3-methyl-3-butenyloxycarbonyl; for alkanoyl: formyl, acetyl and propionyl; for alkylthio: methylthio and ethylthio; for alkylsulphinyl: methylsulphinyl and ethylsulphinyl; for alkylsulphonyl: methylsulphonyl and ethylsulphonyl; for N-alkylcarbamoyl: N-methylcarbamoyl and N-ethylcarbamoyl; and for di-(N-alkyl)carbamoyl: N,N-dimethylcarbamoyl and N,N-diethylcarbamoyl.

A particular value for $R^4$ when it is alkyl is, for example, methyl or ethyl; when it is halogeno is, for example, fluoro, chloro, bromo or iodo; and when it is alkoxy is, for example, methoxy or ethoxy.

A particular value for $R^5$ when it is a non-toxic, biodegradable residue of a physiologically acceptable alcohol or phenol is, for example, a residue derived from a (1–6C) alkanol such as methanol or ethanol, or phenol, glycerol or the like.

A particular value for $R^6$ when it is alkyl is, for example, methyl, ethyl, propyl, isopropyl, butyl or pentyl; and when it is cycloalkyl is, for example, cyclobutyl, cyclopentyl or cyclohexyl.

A particular value for $R^7$ when it is alkyl is, for example, methyl or ethyl; when it is alkanoyl is, for example, formyl, acetyl or propionyl; and when it is —CO.NH.(1–4C)alkyl is, for example, —CONHCH$_3$ or —CONHC$_2$H$_5$.

Particular values for optional substituents which may be present on phenyl moieties, or for an optional substituents which may be present when X is phenylene, or for an optional additional substituent on Z when it is a 2-carboxybenzamido, 2-sulfobenzamido or 2-carboxybenzyloxy group include, by way of example, for halogeno: fluoro, chloro and bromo; for alkyl: methyl and ethyl; and for alkoxy: methoxy and ethoxy.

A particular value for an optional alkanoyl substituent on X which may be present when X is phenylene is, for example, formyl, acetyl or propionyl.

A specific value for X which is of particular interest is, for example, p-phenylene.

A preferred value for $R^1$ is, for example, (1–4C)alkyl such as methyl, ethyl or propyl.

A preferred value for $R^2$ is, for example, hydrogen.

A preferred value for $R^3$ is, for example, (1–4C)alkyl such as methyl or ethyl.

A preferred value for $R^4$ or $R^5$ is, for example, hydrogen.

A preferred value for linking group A is, for example, —CH=CH—CO— or —CH$_2$—CH$_2$—CO—.

A preferred value for Ra or Rb is, for example, hydrogen, alkyl, phenyl, pyridyl, alkoxycarbonyl, carbamoyl, N,N-dialkylcarbamoyl, cyano, hydroxy, phenylthio or phenylsulphinyl.

A preferred combination of values for Ra and Rb is, for example, when they are both hydrogen.

A preferred combination of values for $R^1$ and $R^3$ is, for example, when they are both alkyl.

A preferred value for Z is, for example, 1H-tetrazol-5-yl and which is especially preferred when attached ortho to the group X.

A particular group of compounds of the formula I which are of interest comprises compounds of the formula I as defined above wherein Z is 1H-tetrazol-5-yl, —CO.NH.(1H-tetrazol-5-yl) or a group of the formula —CO.OR$^5$ or —CO.NH.SO$_2$.R$^6$ in which R$^5$ is hydrogen or a non-toxic, biodegradable residue of a physiologically acceptable alcohol or phenol, and R$^6$ is (1–6C)alkyl, (3–8C) cycloalkyl or phenyl; but excluding those compounds wherein one or both of Ra and Rb is selected from pyridyl, carbamoyl, N-alkylcarbamoyl and di-(N-alkyl)carbamoyl of up to 7 carbon atoms, phenylthio and phenylsulphinyl; or an N-oxide thereof; or a non-toxic salt thereof.

A preferred group of compounds of the formula I comprises compounds of the formula Ia wherein $R^1$, $R^2$, $R^3$, $R^4$, Ra, Rb and X have any of the meanings defined above; and $Z^1$ is carboxy or 1H-tetrazol-5-yl; and the non-toxic salts thereof.

A further preferred group of compounds of the formula I comprises compounds of the formula Ia wherein $R^1$, $R^2$, $R^3$, $R^4$ and X have any of the meanings defined above; Ra and Rb are independently selected from (1–4C)alkyl, substituted (1–4C)alkyl containing one or more fluoro substituents or bearing a (3–8C)cycloalkyl, (1–4C) alkoxy or phenyl substituent, (3–8C)cycloalkyl, phenyl, (1–4C)alkoxy, halogeno, carboxy, (1–4C)alkoxycarbonyl, (3–6C)alkenyloxycarbonyl, cyano, nitro, (1–4C)alkanoyl, (1–4C)alkylthio, (1–4C)alkylsulphinyl, (1-4C)alkylsulphonyl or phenylsulphonyl; and $Z^1$ is carboxy or 1H-tetrazol-5-yl; and the non-toxic salts thereof.

A further preferred group of compounds of the formula I comprises compounds of the formula Ib wherein $R^1$, $R^2$, $R^3$, $R^4$, Ra, Rb and X have any of the meanings defined above; and $Z^2$ is carboxy or 1H-tetrazol-5-yl; and the non-toxic salts thereof.

A further preferred group of compounds of the formula I comprises compounds of the formula Ib wherein $R^1$, $R^2$, $R^3$, $R^4$ and X have any of the meanings defined above; Ra and Rb are independently selected from (1-4-C)alkyl, substituted (1-4C)alkyl containing one or more fluoro substituents or bearing a (3-8C)cycloalkyl, (1-4C)alkoxy or phenyl substituent, (3-8C)cycloalkyl, phenyl, (1-4C)alkoxy, halogeno, carboxy, (1-4C)alkoxycarbonyl, (3-6C)alkenyloxycarbonyl, cyano, nitro, (1-4C)alkanoyl, (1-4C)alkylthio, (1-4C)alkylsulphinyl, (1-4C)alkylsulphonyl and phenylsulphonyl; and $Z^2$ is carboxy or 1H-tetrazol-5-yl; or a non-toxic salt thereof.

A further preferred group of compounds of the formula I comprises compounds of the formula Ia or Ib wherein $R^1$ is (1-4C)alkyl; $R^2$ is hydrogen; $R^3$ is (1-4C)alkyl; $R^4$ is hydrogen; Ra and Rb are independently selected from hydrogen, (1-4C)alkyl, halogeno, hydroxy, phenyl, phenyl, 2-pyridyl, 3-pyridyl, phenylthio, phenylsulphinyl, carboxy, (1-4C)alkoxycarbonyl, carbamoyl and N,N-dialkylcarbamoyl of up to 7 carbon atoms; X is p-phenylene; $Z^1$ and $Z^2$ where present are carboxy or 1H-tetrazol-5-yl; or an N-oxide thereof; or a non-toxic salt thereof.

Further groups of compounds of the formula I which are of interest comprise:
(a) Compounds of the formula I wherein X is a direct bond; A is a linking group of the formula —CH═CH—CO— or —CH$_2$—CH$_2$—CO—; and Z is a 2-carboxybenzamido or 2-sulfobenzamido group, the benzene ring of which last two groups optionally bearing 1 or 2 additional substituents independently selected from (1-4C)alkyl, (1-4C)alkoxy and halogeno; and wherein the group Z is attached at the para-position relative to X; and
(b) Compounds of the formula Ia or Ib wherein X is p-phenylene and Z is a group of the formula —SO$_2$NHR$^7$ wherein $R^7$ is hydrogen, (1-4C)alkyl, (1-4C)alkanoyl or —CO.NH.(1-4C)alkyl; and wherein said groups $R^1$, $R^2$, $R^3$, $R^4$, Ra and Rb have any of the meanings defined hereinbefore.

Compounds of the invention which are of particular interest include, for example, the specific embodiments set out hereinafter in the accompanying Examples. Of these, the compounds of formula I described in Examples 1, 2, 3, 13, 17 and 31 are of special interest and these compounds, or a non-toxic salt thereof, are provided as a further feature of the invention.

Although all of the formula I compounds can form salts with suitable acids, it will be appreciated that those compounds of formula I wherein Z is other than an ester group or in which $R^2$, Ra or Rb is a carboxy group can form salts with bases as well as with acids. Particularly suitable non-toxic salts for such compounds therefore also include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —CO.OR$^5$ in which $R^5$ is hydrogen), a carboxylic acid derivative of the formula II, in which Q is a protected carboxy group selected from (1-6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1-4C)alkanol, such as aqueous methanol or ethanol. However, it may also be performed in a mixture of an aqueous and non-aqueous solvent such as water and toluene using a conventional quaternary ammonium phase transfer catalyst. Alternatively, the hydrolysis may be carried out under acidic conditions, for example, using a suitable mineral acid, such as hydrochloric acid, and conveniently in the presence of a suitable solvent or diluent, such as dioxan. The hydrolysis is generally performed at a temperature in the range, for example, 0°–120° C., depending on the reactivity of the group Q. In general, when Q is carbamoyl, temperatures in the range, for example, 40°–120° C. are required to effect the hydrolysis.

Alternatively, when Q is benzyloxycarbonyl the conversion may also be performed by hydrogenolysis, for example using hydrogen at 1-3 bar in the presence of a suitable catalyst, such as palladium on charcoal or on calcium sulphate, in a suitable solvent or diluent such as a (1-4C)alkanol (typically ethanol or 2-propanol) and at a temperature in the range, for example, 0°–40° C.

Further, when Q is t-butoxycarbonyl, the conversion may also be carried out by hydrolysis at a temperature in the range, for example, 0°–100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of the formula VII with a trialkyltin azide, such as tributyltin azide, or triphenyltin azide respectively. The reaction is conveniently carried out in a suitable solvent or diluent, such as toluene or xylene, and at a temperature in the range, for example, 50°–150° C. In a modified procedure, a formula I compound wherein Z is tetrazolyl may be obtained directly by in situ removal of the trialkyltin or triphenyltin group without prior isolation of the formula III compound, for example by the addition of aqueous mineral acid or gaseous hydrogen chloride to the reaction mixture. The nitriles of the formula VII may be obtained, for example, by alkylation of a compound of the formula IV with a nitrile of the formula VIII wherein Hal. stands for a suitable leaving group such as chloro, bromo, iodo, methanesulphonyloxy or p-toluenesulphonyloxy, using similar conditions to those used in process (c) described hereinafter. The necessary compounds of formula VIII may be made by standard procedures such as that illustrated in Scheme 1, using methods of organic chemistry well known in the art. Alternatively, the nitriles of the formula VII may be obtained from stepwise conversion of a compound of formula I wherein Z is a group of the formula —CO.OR$^5$ under standard conditions. Trialkyltin azides and triphenyltin azides are either commercially available or may be prepared by standard procedures well known in the art, such as by reaction of a trialkyltin halide with an alkali metal azide.

c) A compound of the formula IV is alkylated with a compound of the formula V wherein Hal. stands for a suitable leaving group such as chloro, bromo, iodo, methanesulphonyloxy or p-toluenesulphonyloxy.

The reaction is generally carried out in the presence of a suitable base, for example, an alkali metal alkoxide such as sodium methoxide or sodium ethoxide or an alkali metal hydride such as sodium hydride or an alkali metal carbonate such as sodium or potassium carbonate, or an organic base such as diisopropylethylamine and in a suitable solvent or diluent, for example, a (1–4C)alkanol such as methanol or ethanol when an alkali metal alkoxide is used, or in a polar solvent such as N,N-dimethylformamide or N-methylpyrrolidone and at a temperature in the range, for example, 10°–100° C. Alternatively, a quaternary ammonium hydroxide may be used in a mixture of an aqueous and non-aqueous solvent such as water and dichloromethane. In carrying out process (c), when in the starting material Z is an acidic group, about two molecular equivalents of a suitable base is generally required, whereas when Z is a non-acidic group the presence of one molecular equivalent of a suitable base is generally sufficient.

Procedure (c) is particularly suitable for the production of those compounds of the formula I in which Z is a group of the formula —CO.OR$^5$ in which R$^5$ is other than hydrogen, for example wherein R$^5$ is (1–6C)alkyl, benzyl or phenyl, which compounds are also starting materials of formula II for the reaction described in (a) above. Similarly, using an analogous procedure, but starting with the appropriate halomethyl tetrazolyl derivative of the formula VI, the starting materials of the formula III may be obtained for procedure (b).

Certain of the compounds of formula IV are already known and others can be made by analogy therewith using standard procedures of organic chemistry well known in the art, for example as described in standard works of heterocyclic chemistry such as that edited by Elderfield, or as illustrated in Schemes 2, 2a, 2b, 3 and 4. An alternative method for preparing 4-amino-2,6-dialkylpyridines (for example 4-amino-2,6-diethylpyridine) which may be used, for example, in the procedures shown in Schemes 2, 2a or 4 is, for example, as illustrated in Scheme 6. Compounds of formula IV may also be obtained by using similar procedures to those well known in the art for the preparation of quinolones and indolinones but starting from the appropriately substituted pyridine derivative. It will be appreciated that a compound of the formula IV can be converted into another compound of the formula IV by functional group interconversion using procedures well known in the art. For example, when Ra or Rb is an ester group it may be converted into an amide by reaction with an appropriate amine or hydrolysed to a carboxylic acid group, and when Ra or Rb is hydroxy it may be converted to a halogeno group with a suitable halogenating agent (such as phosphorus oxychloride). The necessary compounds of the formula V (and also of formula VI) may be made by standard procedures such as those which are illustrated in Scheme 1 for compounds in which X is phenylene.

Compounds of the formula VI wherein X is phenylene may also be conveniently obtained by reaction of a Grignard reagent, formed from a suitably substituted 4-bromotoluene, with a trialkyltin halide, such as tributyltin chloride, followed by reaction of the resulting (substituted)phenyltrialkyltin compound with a bromobenzonitrile in the presence of a palladium(0) catalyst, such as tetrakis(triphenylphosphine)palladium, and azo(bisisobutyronitrile). The resultant substituted 4'-methyl-biphenylcarbonitrile may then be converted to a compound of the formula VI by carrying out steps (b), (c) and (d) in a similar manner to that shown in Scheme 1. Alternatively, suitably substituted 4'-methylbiphenylcarbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(bisisobutyronitrile).

(d) For those compounds of the formula I wherein X is a direct bond between the adjacent phenyl and methylene groups and Z is a 2-carboxybenzamido or 2-sulfobenzamido group, the benzene ring of which last two groups may optionally bear 1 or 2 additional substituents independently selected from (1–4C)alkyl, (1–4C)alkoxy and halogeno, a compound of the formula XII in which X is a direct bond is reacted with an anhydride of the formula XIII wherein Xa is carbonyl or sulphonyl and Rc and Rd are independently selected from hydrogen, (1–4C)alkyl, (1–4C)alkoxy or halogeno.

The reaction is generally carried out in a suitable solvent or diluent, for example, an ether such as tetrahydrofuran, and at a temperature in the range, for example, 0°–50° C. The compounds of formula XII wherein X is a direct bond may be obtained, for example, by alkylation of a compound of the formula IV with an unsubstituted or appropriately substituted nitrobenzyl halide, using analogous conditions to those described in process (c) above, followed by reduction of the nitro group under standard conditions, for example by catalytic hydrogenation over platinum oxide in a suitable solvent, such as a (1-4C)alcohol (typically ethanol or 2-propanol) or ether (for example, dioxan or tetrahydrofuran), and at a temperature in the range, for example, 0°-40° C. The anhydrides of formula XIII are commercially available or can be made by standard procedures.

(e) For those compounds wherein Z is $-NHSO_2CF_3$, a compound of the formula XII is reacted with trifluoromethanesulphonic anhydride.

The reaction is generally carried out in a suitable solvent or diluent, for example a chlorinated hydrocarbon such as dichloromethane or chloroform, and at a temperature in the range, for example, $-78°$ C. to ambient temperature. The compounds of formula XII wherein X is a direct bond may be obtained as described above and the compounds of formula XII wherein X is biphenylene may be obtained, for example, using the procedures described in EPA, publication no. 400974, or by analogy therewith.

(f) For those compounds of formula I wherein Z is a group of the formula $-SO_2NHR^7$, a compound of the formula IV is alkylated with a compound of the formula XV wherein Hal. stands for a suitable leaving group such as chloro, bromo, iodo, methanesulphonyloxy or p-toluenesulphonyloxy.

The reaction is generally carried out using similar conditions to those described for procedure (c). The compounds of formula XV may be obtained by standard procedures such as those described in EPA, Publication No. 400974 for compounds in which X is phenylene, or by analogy therewith.

(g) For those compounds of the formula I wherein X is phenylene and Z is a group of the formula $-SO_2NHR^7$, a compound of the formula X is reacted with a compound of the formula XIV wherein $W^1$ is a bromo, iodo or trifluoromethanesulphonyloxy group.

The reaction may be carried out using similar conditions to those described hereinafter for the reaction of a compound of formula X with a compound of formula XI. The compounds of formula XIV may be obtained by standard procedures well known in the art. A compound of the formula I wherein Z is $-SO_2NH_2$ may also be obtained by acid hydrolysis of a compound of the formula I wherein Z is a group of the formula $-SO_2NHR^7$ in which $R^7$ is a tert-butyl group. The hydrolysis is generally carried out in the presence of a strong acid, such as trifluoroacetic acid. The acid may be used in excess or in the presence of a suitable diluent such as tetrahydrofuran, t-butyl methyl ether or 1,2-dimethoxyethane, and at a temperature in the range, for example, 0°-100° C. Alternatively, compounds of the formula I wherein Z is $-SO_3NHR^7$ may be obtained from the corresponding compound in which Z is $-SO_2NH_2$, for example, by alkylation, acylation (such as with an appropriate acid chloride, acid anhydride or other acylating agent) or reaction with an alkyl isocyanate, using standard conditions.

Whereafter, those compounds of formula I wherein Ra or Rb is hydroxy may be obtained by reaction of a compound of the formula I wherein Ra or Rb is (1-4C-)alkoxy with a dealkylating agent under standard conditions (for example using boron tribromide in dichloromethane at a temperature in the range, for example, $-10°$ C. to ambient temperature).

Whereafter, those compounds of formula I wherein Z is 1H-tetrazol-5-yl may be obtained by stepwise conversion of a compound of the formula I wherein Z is a group of the formula $-CO.OR^5$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is $-CO.NH.(1H-tetrazol-5-yl)$, a group of the formula $-CO.NH.SO_2R^6$ or a group of the formula $-CO.OR^5$ in which $R^5$ is other than hydrogen, may be obtained, for example, by reacting a carboxylic acid of the formula I in which Z is carboxy (or a reactive derivative of said acid) with 5-aminotetrazole, a sulphonamide of the formula $NH_2.SO_2R^6$ or a salt thereof (for example, an alkali metal salt), or a hydroxy compound of the formula $HO.R^5$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine, pyridine or 4-dimethylaminopyridine. When a reactive derivative is used, either the reaction is carried out in the presence of a base such as mentioned above, or, for the preparation of a compound of the formula I wherein Z is a group of the formula $-CO.NH.SO_2R^6$ or a group of the formula $-CO.OR^5$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°-60° C.

Whereafter, when an N-oxide derivative of a compound of the formula I is required, a compound of the formula I is oxidised. Suitable oxidising agents include those well known in the art for the conversion of nitrogen heterocycles to their corresponding N-oxide derivatives, for example, hydrogen peroxide or an organic peracid such as m-chloroperbenzoic acid or peracetic acid. The oxidation is preferably carried out in a suitable conventional solvent or diluent for such oxidations, for example dichloromethane, chloroform or acetic acid, and at a temperature in the general range, for example 0° to 80° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

According to a further aspect of the invention, there is provided a process for the manufacture of a compound of the formula I wherein Z is tetrazolyl, X is p-phenylene optionally bearing a substituent selected from (1–4C)alkyl, (1–4C)alkoxy, halogeno, (1–4C)alkanoyl, trifluoromethyl, cyano and nitro, and $R^1$, $R^2$, $R^3$, $R^4$, Ra, Rb and A have any of the meanings defined hereinbefore; which comprises reaction of a compound of the formula IX wherein $P^1$ is an electron-deficient phenyl group or a pyridyl or pyrimidyl group; Ry is hydrogen, (1–4C)alkyl, (1–4)alkoxy, halogeno, (1–4C)alkanoyl, trifluoromethyl, cyano or nitro; and $R^1$, $R^2$, $R^3$, $R^4$, Ra, Rb and A have any of the values defined above; with a base selected from an alkali metal hydroxide, (1–12C)alkanolate, (1–12C)alkanethiolate, phenolate, thiophenolate or diphenylphosphide, wherein any phenyl ring of the latter three groups may optionally bear a (1–4C)alkyl, (1–4C)alkoxy or halogeno group.

A particular value for $P^1$ includes, for example, a phenyl group bearing 1, 2 or 3 electron-withdrawing groups independently selected from nitro, cyano and trifluoromethyl.

A particular value for Ry when it is alkyl is, for example, methyl or ethyl; when it is alkoxy is, for example, methoxy or ethoxy; when it is alkanoyl is, for example, formyl, acetyl or propionyl; and when it is halogeno is, for example, fluoro, chloro, bromo or iodo.

A particular value for a base includes the following by way of example:

for an alkali metal hydroxide: sodium or potassium hydroxide;

for an alkali metal alkanolate: an alkali metal (1–8C)alkanolate, for example an alkali metal (1–4C)alkoxide, such as sodium or potassium methoxide, ethoxide, propoxide or butoxide;

for an alkali metal alkanethiolate: an alkali metal (1–8C)alkanethiolate, for example an alkali metal (1–4C)alkanethiolate such as sodium or potassium methanethiolate, ethanethiolate, propanethiolate or butanethiolate.

A particular value for an optional substituent on a phenyl group of an alkali metal phenolate, thiophenolate or diphenylphosphide, when it is alkyl is, for example, methyl or ethyl; when it is alkoxy is, for example, methoxy or ethoxy; and when it is halogeno is, for example, fluoro, chloro or bromo.

A preferred value for $P^1$ is, for example, a nitrophenyl group, especially 4-nitrophenyl.

A preferred value for X is, for example, when it is unsubstituted p-phenylene.

A particularly preferred base is an alkali metal alkanethiolate such as sodium or potassium propanethiolate, an alkali metal alkanolate such as sodium or potassium ethoxide or methoxide, or an alkali metal thiophenolate such as sodium or potassium 4-fluorothiophenolate.

It will be appreciated that when the base is an alkali metal alkanolate, alkanethiolate, phenolate, thiophenolate or diphenylphosphide, it may be generated in situ from the corresponding alkanol, alkanethiol, phenol, thiophenol or diphenylphosphine with a suitable alkali metal base such as an alkali metal hydride, for example, lithium, potassium or sodium hydride.

The process of the invention is particularly useful for the preparation of compounds of the formula I wherein the tetrazolyl group is at the ortho position relative to the adjacent phenyl group.

The reaction is conveniently carried out in a suitable inert organic solvent or diluent, for example, a polar solvent such as N,N-dimethylformamide or N-methylpyrrolidone. Alternatively, an alkanol such as methanol or ethanol may be used, for example, when an alkali metal hydroxide or alkoxide such as sodium or potassium hydroxide, methoxide or ethoxide is employed. The reaction is generally carried out at a temperature in the range, for example, −30° C. to 50° C. It will be appreciated that the choice of temperature will depend on the nature of the base employed. For example, when an alkali metal alkanethiolate or alkanolate is used, a temperature in the range of 0° C. to ambient temperature is preferred.

Compounds of the formula IX may be obtained by reaction of a boronic acid of the formula X with a compound of the formula XI wherein $P^1$ is an electron-deficient phenyl group having any of the meanings defined above and W is a bromo, iodo or trifluoromethanesulphonyloxy group, in the presence of a palladium(0) catalyst, such as tetrakis(triphenylphosphine)palladium, and azo(bisisobutyronitrile). The reaction is preferably carried out in the presence of a base, such as sodium or potassium carbonate, in an inert solvent or diluent, for example, a hydrocarbon such as toluene or xylene, an ether, such as dioxan or tetrahydrofuran, an (1–4C)alkanol such as methanol or ethanol, water, or mixture thereof, for example a mixture of water, methanol and toluene, and at a temperature in the range of, for example, 50° C. to 150° C., and conveniently at or about the reflux temperature of the solvent or mixture of solvents used.

Compounds of the formula X may be obtained, for example, by heating at reflux a 4-methylphenylboronic acid in a solvent such as methyl chloroform with azeotropic removal of water, followed by radical bromination of the product which may be carried out in situ, for example with bromine or N-bromosuccinimide in the presence of azo(bisisobutyronitrile). The resultant 4-bromomethylphenylboronic acid anhydride may then be used to alkylate a compound of the formula IV (using similar alkylation conditions to those used in process (c) described above), followed by subsequent acidic hydrolysis, to give a formula X compound. Alternatively the product from the alkylation step prior to hydrolysis may be isolated and reacted directly with a compound of the formula XI under similar conditions to those described above to obtain a formula IX compound directly. In a yet further alternative procedure, a 4-methylphenylboronic acid and an appropriate alkanediol, for example 2,2-dimethylpropan-1,3-diol, may be heated at reflux in a solvent (such as cyclohexane) with azeotropic removal of water followed by free radical bromination of the product, which may be carried out in situ. The resultant bromomethyl compound may then be reacted using analogous procedures to those described above for the 4-bromomethylphenylboronic acid anhydride to obtain a formula X compound or a compound of the formula IX directly. Compounds of the formula XI may be obtained, for example, as shown in Scheme 5.

Whereafter, an N-oxide and/or a non-toxic salt and/or an optically active form of a compound of the formula I may be obtained as described above for procedures (a) to (g) if desired.

It will be appreciated that where necessary in any of the above processes, reactive or labile groups may be protected in a conventional manner and subsequently deprotected, using conventional protecting groups and deprotection procedures, for example, as described in "Protective Groups in Organic Synthesis" by Theodora Green (John Wiley and Sons Inc, 1981).

Certain of the intermediates defined herein are novel, for example the compounds of the formula II, III, IV, VII and IX and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The compounds of the invention may also be useful for the treatment of ocular hypertension, glaucoma, cognitive disorders (such as Alzheimer's disease, amnesia, senile dementia and learning disorders), as well as other diseases such as renal failure, cardiac insufficiency, post-myocardial infarction, cerebrovascular disorders, anxiety, depression and certain mental illnesses such as schizophrenia.

The antagonism of one or more of the physiological actions of AII and, in particular, the antagonism of the interaction of AII with the receptors which mediate its effects on a target tissue, may be assessed using one or more of the following, routine laboratory procedures:

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of about 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, acidic compounds of formula I as defined above show significant inhibition in Test B at a final concentration of about 50 micromolar or much less. [Note: Compounds of formula I wherein Z is a group of the formula —$CO.OR^5$ in which $R^5$ is other than hydrogen in general show only weak activity in the in vitro Tests A or B.]

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of about 50 mg/kg body weight or much less, without any overt toxicological or other untoward pharmacological effect.

Test D: This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of about 50 mg/kg body weight or much less, without any overt toxicological or other untoward pharmacological effect.

By way of illustration of the angiotensin II inhibitory properties of compounds of the formula I, the compound of Example I gave the following results in tests A and C described above:

In test A: an $IC_{50}$ of $8.84 \times 10^{-9}$M;

In test C: an $ED_{50}$ of 0.048 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt or N-oxide thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I, or a non-toxic salt thereof, may also be advantageously administered for therapeutic or prophylactic purposes together with another pharmacological agent known in the general art to be of value in treating one or more of the diseases or medical conditions referred to hereinabove, such as a beta-adrenergic blocker (for example atenolol), a calcium channel blocker (for example nifedipine), an angiotensin converting enzyme (ACE) inhibitor (for example lisinopril) or a diuretic (for example furosemide or hydrochlorothiazide). It is to be understood that such combination therapy constitutes a further aspect of the invention.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;
(ii) operations were carried out at room temperature, that is in the range 18°-26° C.;
(iii) flash column chromatography was performed on Merck Kieselgel 60 (Art. no. 9385) obtained from E Merck, Darmstadt, Germany;
(iv) yields, where given, are intended for the assistance of the reader only and are not necessarily the maximum attainable by diligent process development;
(v) $^1$H NMR spectra were determined at 200 MHz in CDCl$_3$ or d$_6$-dimethylsulphoxide (d$_6$-DMSO) using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;
(vi) the term "naphthyridinone" is equivalent to the term "naphthyridone"; the term "1,2-dihydro-1,6-naphthyridin-2-one" is equivalent to the term "1,6-naphthyridin-2(1H)-one"; and the term "1,2,3,4-tetrahydro-1,6-naphthyridin-2-one" is equivalent to the term "3,4-dihydro-1,6-naphthyridin-2(1H)-one"; and
(vi) the term "1H-tetrazol-5-yl" stands for "1H-1,2,3,4-tetrazol-5-yl".

EXAMPLE 1

Concentrated hydrochloric acid (0.3 ml) was added to a solution of 5,7-dimethyl-1-[(2'-(2-triphenylmethyl-2H-tetrazol-5-yl)biphenyl-4-yl)methyl]-1,6-naphthyridin-2(1H)-one (280 mg) (A) in dichloromethane/methanol (4 ml) (3:1 v/v) and the mixture was stirred for 30 minutes. Volatile material was removed by evaporation and the residue was stirred with ether. The insoluble solid was collected by filtration and recrystallised from ethanol/methanol (1:1 v/v) to give 5,7-dimethyl-1-[(2'-(1H-tetrazol-5-yl)biphenyl-4-yl)methyl]-1,6-naphthyridin-2(1H)-one hydrochloride (105 mg), as a solid, m.p. 278°-280° C. (decomposition); NMR (d$_6$-DMSO): 2.68(s,3H), 2.96(s,3H), 5.51(s,2H), 6.94(d,1H), 7.05(d,2H), 7.17(d,2H), 7.45-7.71(m,5H), 8.31(d,1H); mass spectrum (positive fast atom bombardment (+ve FAB), DMSO/methanol/nitrobenzyl alcohol(NBA)): 409(M+H)$^+$; microanalysis, found: C, 64.1; H, 4.6; N, 18.7%; C$_{24}$H$_{20}$N$_6$O.HCl.0.2H$_2$O requires: C,64.1; H,4.8; N,18.7%.

The starting material A was obtained as follows: 5,7-dimethyl-1,6-naphthyridin-2(1H)-one (250 mg) (obtained as described in *Chem. Pharm. Bull.*, 1985, 33, 4764) was added to a suspension of sodium hydride (88 mg) (60% dispersion in mineral oil) in N,N-dimethylformamide (DMF) (30 ml) and the mixture was stirred for 1 hour. 5-[2-(4'-Bromomethylbiphenylyl)]-2-triphenylmethyl-2H-tetrazole (1.06 g) (obtained as described in European patent application, publication no. 0291969) was added and the mixture was stirred for 4 hours. Solvent was removed by evaporation and the residue was partitioned between ethyl acetate and water. The organic layer was separated, washed with water, saturated sodium chloride solution and dried. Solvent was removed by evaporation and the residue was purified by flash chromatography eluting with dichloromethane/methanol (49:1 v/v) to give 5,7-dimethyl-1-[(2'-(2-triphenylmethyl-2H-tetrazol-5-yl)biphenyl-4-yl)methyl]-1,6-naphthyridin-2(1H)-one (320 mg) as a foam; NMR (CDCl$_3$): 2.39(s,3H), 2.77(s,3H), 5.36(s,2H), 6.73-6.82(m,2H), 6.88-7.16(complex m,10H), 7.17-7.52-(complex m,12H), 7.89(m,1H), 7.98(d,1H); mass spectrum (+ve FAB, DMSO/methanol/NBA): 651(M+H)$^+$.

EXAMPLE 2

Concentrated hydrochloric acid (0.5 ml) was added to a solution of 5,7-diethyl-1-[(2'-(2-triphenylmethyl-2H-tetrazol-5-yl)biphenyl-4-yl)methyl]-1,6-naphthyridin-2(1H)-one (500 mg) (A) in methanol (5 ml) and the mixture was stirred for 30 minutes. Volatile material was removed by evaporation and the residue was dissolved in hot ethanol. The solution was cooled, evaporated to small volume and the product collected by filtration to give 5,7-diethyl-1-[(2'-(1H-tetrazol-5-yl)biphenyl-4-yl)methyl]-1,6-naphthyridin-2(1H)-one hydrochloride (230 mg), as a solid, m.p. 265°-269° C. (decomposition); NMR (d$_6$-DMSO): 1.15-1.4(m,6H), 2.95(q,2H), 3.35(q,2H), 5.55(s,2H), 6.9(d,1H), 7.05(d,2H), 7.2(d,2H), 7.4-7.75(m,5H), 8.45(d,1H); mass spectrum (+ve FAB, methanol/NBA): 459(M+Na)$^+$, 437(M+H)$^+$; microanalysis, found: C, 64.8; H, 5.4; N, 17.4; C$_{26}$H$_{24}$N$_6$O.HCl.0.5H$_2$O requires C, 64.8; H, 5.4; N, 17.4%.

The starting material A was obtained as follows:

(i) A solution of tin tetrachloride (24 ml) in toluene (70 ml) was added to a stirred solution of 3-amino-2-pentenenitrile (10 g) (obtained as described in *J. Het. Chem.*, 1989, 26, 1575) and methyl propionylacetate (13.4 g) in toluene (150 ml). The mixture was heated at reflux for 6 hours and then stirred at ambient temperature for 16 hours. Saturated sodium carbonate solution was added to the stirred mixture until the aqueous phase was basic (pH>9). Ether (200 ml) was added to the mixture and the precipitated tin salts removed by filtration through diatomaceous earth. The organic phase of the filtrate was separated, washed with sodium chloride solution and dried (MgSO$_4$). Solvent was removed by evaporation and the residue was extracted with hot hexane (3×50 ml). The combined hexane extracts were evaporated and the residue was dissolved in minimum of hot hexane. The solution was then cooled at 4° C. for 16 hours when a yellow solid crystallised. The solid (7.3 g) was collected by filtration and purified by flash chromatography eluting with dichloromethane/methanol (1:19 v/v) to give methyl 4-amino-2,6-diethylpyridine-3-carboxylate (B) (6 g) as a light yellow solid, m.p. 75° C.; NMR (CDCl$_3$): 1.25(t,6H), 2.65(q,2H), 2.95(q,2H), 3.9(s,3H), 5.65(broad s,2H), 6.25(s,1H); mass spectrum (chemical ionisation (CI), ammonia): 209(M+H)+.

(ii) Methyl 4-amino-2,6-diethylpyridine-3-carboxylate (B) (3.94 g) was added to a mixture of 2M sodium hydroxide solution (9.5 ml) and methanol (40 ml) and the mixture was heated at reflux for 16 hours. The solution was cooled to ambient temperature and volatile material was removed by evaporation. The residue was partitioned between ethyl acetate and a mixture of 2M hydrochloric acid (9.5 ml) and water (20 ml). The aqueous phase was separated, water was removed by evaporation and the residue was extracted with ethyl acetate/methanol (1:1 v/v). The combined organic extracts were filtered and solvent was removed from the filtrate by evaporation to give 4-amino-2,6-diethylpyridine-3-carboxylic acid (C) (3.46 g) as a yellow-brown foam; NMR (d$_6$-DMSO): 1.18(m,6H), 2.64(q,2H), 3.12(q,2H), 6.49(s,1H), 8.28(broad s,2H); mass spectrum (chemical ionisation, ammonia): 195(M+H)+.

(iii) 4-Amino-2,6-diethylpyridine-3-carboxylic acid (C) (3.26 g) was heated at 220° C. for 50 minutes. The residue was cooled to ambient temperature and purified by flash chromatography eluting with concentrated aqueous ammonia solution/dichloromethane/methanol (1:85:15 v/v) to give 4-amino-2,6-diethylpyridine (D) (1.94 g) as a solid, m.p. 133°-137° C.; NMR (CDCl$_3$/d$_6$-DMSO): 1.24(t,6H), 2.68(q,4H), 4.48(broad s,2H), 6.27(s,2H); mass spectrum (chemical ionisation, ammonia): 151(M+H)+.

(iv) 4-Amino-2,6-diethylpyridine (D) (1.8 g) was added to a solution of iodine (3.1 g) and [bis(trifluoroacetoxy)iodo]benzene (5.7 g) in a mixture of dichloromethane (70 ml) and methanol (20 ml) and the mixture was stirred for 16 hours. Solvent was removed by evaporation and the residue was partitioned between ethyl acetate and a mixture of saturated sodium metabisulphite solution (50 ml) and saturated sodium carbonate solution (150 ml). The organic phase was separated, washed with saturated sodium chloride solution and dried (MgSO$_4$). Solvent was removed by evaporation and the residue was purified by flash chromatography eluting with dichloromethane/methanol (97:3 v/v) to give 4-amino-2,6-diethyl-3-iodopyridine (E) (1.33 g) as a solid, m.p. 72°-74° C.; NMR (CDCl$_3$): 1.25(m,6H), 2.65(q,2H), 2.96(q,2H), 4.59(broad s,2H), 6.30(s,1H); mass spectrum (chemical ionisation, ammonia): 277(M+H)+.

(v) Palladium (II) acetate (50 mg) and tri(2-methylphenyl)phosphine (50 mg) were added to a solution of 4-amino-2,6-diethyl-3-iodopyridine (E) (1.3 g), ethyl acrylate (1.2 ml) and triethylamine (1.2 ml) in DMF (25 ml). The mixture was heated at 130° C. for 2 hours and then allowed to cool. Volatile material was removed by evaporation and the residue was purified by flash chromatography, eluting with aqueous ammonia (density 0.88 g/ml)/dichloromethane/methanol (1:200:20, v/v/v) to give ethyl -3-[(4-amino-2,6-diethyl) pyridin-3-yl]acrylate (G), as an oil; NMR (CDCl$_3$): 1.15-1.45(m,9H), 2.7(q,2H), 2.8(q,2H), 4.25(q,2H), 4.5(broad s,2H), 6.25(d,2H), 7.75(d,2H); mass spectrum (chemical ionisation, ammonia): 249 (M+H)+.

(vi) A solution of ethyl-3-[(4-amino-2,6-diethyl)pyridin-3-yl]acrylate (G) (600 mg) in dry methanol (10 ml) was added to a solution of sodium methoxide, prepared from sodium (500 mg) and dry methanol (30 ml), and the mixture was heated at reflux under an atmosphere of argon for 3 hours. Solvent was removed by evaporation and the residue partitioned between ethyl acetate and water. The aqueous phase was separated and extracted with ethyl acetate. The combined organic solutions were washed with saturated sodium chloride solution and then dried (MgSO$_4$). The solvent was removed by evaporation and the residue was triturated with ether to give 5,7-diethyl-1,6-naphthyridin-2(1H)-one (H) (310 mg), as a solid, m.p. 170°-171° C.; NMR (CDCl$_3$): 1.45(m,6H), 2.85(q,2H), 3.1(q,2H), 6.7(d,1H), 6.95(s,1H), 8.05(d,1H), 12.05(broad s,1H): mass spectrum (chemical ionisation, ammonia): 203(M+H)+.

(vii) 5,7-Diethyl-1,6-naphthyridin-2(1H)-one (H) (290 mg) was added to a suspension of sodium hydride (60% dispersion in mineral oil; 90 mg) in DMF (20 ml) and the mixture was stirred for 40 minutes. 5-[2-(4'-Bromomethylbiphenylyl)]-2-triphenylmethyl-2H-tetrazole (1.06 g) was added and the mixture was stirred for 2.5 hours. Solvent was removed by evaporation and the residue was partitioned between ethyl acetate and water. The organic layer was separated, washed with water, saturated sodium chloride solution and dried (MgSO$_4$). Solvent was removed by evaporation and the residue was purified by flash chromatography eluting with ethyl acetate/hexane (3:7 v/v, increasing to 1:1 v/v) to give 5,7-diethyl-1-[2'-(2-triphenylmethyl-2H-tetrazol-5-yl)biphenyl-4-yl)methyl]-1,6-naphthyridin-2(1H)-one (A) (616 mg), as a foam; NMR (CDCl$_3$): 1.15(t,3H), 1.35(t,3H), 2.65(q,2H), 3.1(q,2H), 5.4(s,2H), 6.7-7.5-(complex m,24H), 7.85(m,1H), 7.95(d,1H); mass spectrum (+ve FAB, DMSO/nitrobenzyl alcohol): 701(M+Na)+, 679(M+H)+.

5,7-Diethyl-1,6-naphthyridin-2(1H)-one was alternatively prepared according to the following procedure:

Procedure 1

(i) A mixture of methyl 3-aminopentenoate (7.3 g) and 5-(1-hydroxypropylidene)-2,2-dimethyl-1,3-dioxane-4,6-dione (23.0 g) (obtained as described in *J. Org. Chem.*, 1978, 43, 2087) was heated at 120° C. for 2 hours. The mixture was cooled to ambient temperature and triturated with ether (50 ml). The product was collected by filtration to give methyl 2,6-diethyl-4-oxo-1,4-dihydropyridine-3-carboxylate (5.2 g) as a solid, m.p. 124°-127° C.; NMR (d$_6$-DMSO): 1.2(t, 6H), 2.3-2.6(m, 4H), 3.7(s, 3H), 5.9(s, 1H), 11.2(s, 1H); mass spectrum (CI, ammonia): 210 (M+H)+; microanalysis, found: C, 63.1; H, 7.5; N, 6.7%; $C_{11}H_{15}NO_3$ requires: C, 63.1; H, 7.2; N, 6.7%.

(ii) Tosyl isocyanate (39.12 g) was added to a stirred suspension of methyl 2,6-diethyl-4-oxo-1,4-dihydropyridine-3-carboxylate (25.0 g) in acetonitrile (300 ml). After the initial exotherm had subsided the mixture was heated at reflux for 2 hours. The mixture was cooled to ambient temperature and the suspended solid was collected by filtration to give methyl 2,6-diethyl-4-(4-tosylamino)pyridine-3-carboxylate (37.12 g) as a solid, m.p. 185°-187° C.; NMR ($d_4$-methanol): 1.22(t, 6H), 2.38(s, 3H), 2.62(two q, 4H), 3.88(s, 3H), 7.1(s, 1H), 7.28(d, 2H), 7.75(d, 2H); mass spectrum: (CI, ammonia): 363 (M+H)+; microanalysis, found: C, 59.3; H, 6.1; N, 7.8%; $C_{18}H_{22}N_2SO_4$ requires C, 59.6; H, 6.12; N, 7.73%.

(iii) 2,6-Diethyl-4-(4-tosylamino)pyridine-3-carboxylate (36.4 g) was dissolved in concentrated sulphuric acid (50 ml) and the mixture was stirred at 50° C. for 1 hour. The mixture was cooled to ambient temperature and poured onto ice. The mixture was then adjusted to pH 8 with solid sodium bicarbonate and the suspended solid was collected by filtration to give methyl 4-amino-2,6-diethylpyridine-3-carboxylate (18.23 g) as a white solid, m.p. 82.5°-84.5° C.; NMR ($d_6$-DMSO): 1.13(two t, 6H), 2.51(q, 2H), 2.72(q, 2H), 3.80(s, 3H), 6.37(s, 1H), 6.45(s, 2H); mass spectrum (CI, ammonia): 209 (M+H)+; microanalysis, found: C, 62.8; H, 7.8; N, 13.5%; $C_{11}H_{16}N_2O_2.0.1H_2O$ requires: C, 62.9; H, 7.7; N, 13.3%.

(iv) A solution of methyl 4-amino-2,6-diethyl-pyridine-3-carboxylate (25 g) in THF (125 ml) was added dropwise to a stirred suspension of lithium aluminum hydride (6.5 g) in anhydrous ether (500 ml) over 1 hour. The reaction mixture was then stirred and heated under reflux for 2 hours. The reaction mixture was cooled in an ice-bath and water (6.5 ml) was added cautiously. 2M Aqueous sodium hydroxide solution (6.5 ml) was then added cautiously, followed by water (20 ml), and the resulting mixture was stirred for 1 hour. THF (150 ml) was added and the mixture was stirred for a further hour. Insoluble material was removed by filtration and washed with ethyl acetate (500 ml). The combined filtrates were dried (MgSO$_4$) and volatile material was removed by evaporation to give 4-amino-2,6-diethyl-3-hydroxymethylpyridine as a solid (21.5 g), m.p. 135°-137° C. (after recrystallisation from ethyl acetate/petroleum ether); NMR (CDCl$_3$+$d_6$-DMSO): 1.19(t, 3H), 1.21(t, 3H), 2.58(q, 2H), 2.75(q, 2H), 4.62(s, 2H) 5.12(s, 2H), 6.33(s, 1H); mass spectrum (CI): 181 (M+H)+; microanalysis, found: C, 66.6; H, 9.0; N, 15.5%; $C_{10}H_{16}N_2O$ requires: C, 66.6; H, 8.95; N, 15.5%.

(v) A mixture of 4-amino-2,6-diethyl-3-hydroxymethylpyridine (21.5 g) and activated manganese dioxide (21.0 g) in toluene (500 ml) was stirred and heated at reflux for 3 hours. The hot reaction mixture was filtered and the solid washed with ethyl acetate (500 ml). The combined filtrates were concentrated by evaporation to give 4-amino-2,6-diethylpyridine-3-carbaldehyde (B) as a yellow solid (20.3 g), m.p. 92°-94° C. (after recrystallisation from petroleum ether); NMR (CDCl$_3$): 1.25(t, 3H), 1.33(t, 3H), 2.65(q, 2H), 3.03(q, 2H), 6.24(s, 1H), 10.35(s, 1H); mass spectrum (CI): 179 (M+H)+; microanalysis, found: C, 67.0; H, 7.9; N, 15.7%; $C_{10}H_{14}N_2O$ requires: C, 67.4; H, 7.9; N, 15.7%.

(vi) A mixture of 4-amino-2,6-diethylpyridine-3-carbaldehyde (40 g) and (carboxymethylene)triphenylphosphorane (82.5 g) in toluene (1 l) was stirred and heated at reflux for 3 hours. The solution was cooled and the solvent was removed by evaporation. A solution of sodium (20 g) in methanol (800 ml) was added to the residue and the resulting solution was heated at reflux for 4 hours. Methanol was removed by evaporation and water (500 ml) was added. The mixture was acidified to pH 1-2 by addition of concentrated hydrochloric acid. The mixture was then extracted with ethyl acetate (2×500 ml) and ether (1×500) and the extracts were discarded. The aqueous phase was then basified by addition of solid potassium carbonate and the solid which crystallised was collected by filtration and washed with water. The solid was recrystallised from acetone to give 5,7-diethyl-1,6-naphthyridin-2(1H)-one (34.6 g), m.p. 168°-169° C.; NMR ($d_6$-DMSO): 1.24(dt, 6H), 2.72(q, 2H), 3.0(q, 2H), 6.46(d, 1H), 6.9(s, 1H), 8.07(d, 1H); mass spectrum (CI): 203 (M+H)+; microanalysis, found: C, 70.9; H, 6.9; N, 13.8%; $C_{12}H_{14}N_2O$ requires: C, 71.3; H, 6.98; N, 13.9%.

5,7-Diethyl-1-[(2'-(2-triphenylmethyl-2H-tetrazol-5-yl)biphenyl-4-yl)methyl]-1,6-naphthyridin-2(1H)-one was alternatively obtained according to the following procedure:

Procedure 2

(i) A mixture of 4-amino-2,6-diethylpyridine-3-carbaldehyde (2.0 g) and acetic anhydride (10 ml) in pyridine (20 ml) was heated at reflux for 3 hours. Volatile material was removed by evaporation and the residue was dissolved in ethyl acetate. The solution was washed with aqueous sodium carbonate solution, followed by saturated sodium chloride solution and then dried (MgSO$_4$). Volatile material was removed by evaporation to give an oil which was purified by flash chromatography, eluting with ethyl acetate/petroleum ether (1:1 v/v) to give 4-acetylamino-2,6-diethylpyridine-3-carboxaldehyde as a yellow solid (0.9 g); m.p. 91°-92° C.; NMR (CDCl$_3$): 1.3(t, 3H), 1.35(t, 3H), 2.26(s, 3H), 2.8(q, 2H), 3.14(q, 2H), 8.38(s, 1H), 10.4(s, 1H), 11.7(broad, 1H); mass spectrum (CI): 221 (M+H)+; microanalysis, found: C, 65.3; H, 7.3; N, 12.3%; $C_{12}H_{16}N_2O_2$ requires: C, 65.4; H, 7.3; N, 12.7%.

(ii) Sodium hydride (50% dispersion in oil; 110 mg) was added to a solution of 4-acetylamino-2,6-diethylpyridine-3-carbaldehyde (440 mg) in DMF (10 ml) and the mixture was stirred until effervescence ceased. 5-[2-(4'-Bromomethylbiphenylyl)]-2-triphenylmethyl-2H-tetrazole (1.47 g) was added and the mixture was stirred for 3 hours. The reaction mixture was poured into water and extracted twice with ethyl acetate. The combined extracts were washed with water, followed by saturated sodium chloride solution and dried (MgSO$_4$). Volatile material was removed by evaporation to give an oil which was purified by flash chromatography, eluting with ethyl acetate/petroleum ether (1:3 v/v gradually increasing to 2:3 v/v). The first product eluted was 2,6-diethyl-4-[N-([2'-(2-triphenylmethyl-2H-tetrazol-5-yl)biphenyl-4-yl]methyl)acetamido]pyridine-3-carbaldehyde obtained as an oil; NMR (CDCl$_3$): 1.17(t, 3H), 1.23(t, 3H), 1.85(s, 3H), 2.73(q, 2H), 3.11(q, 2H), 4.41(d, 1H), 5.09(d, 1H), 6.55(s, 1H), 6.85-8.0(complex m, 23H), 10.05(s, 1H)]. The second product eluted was 5,7-diethyl-1-[(2'-(2-triphenylmethyl-2H-tetrazol-5-yl)biphenyl-4-yl)methyl]-1,6-naphthyridin-2(1H)-one (92 mg) as a solid, m.p. 128°-132° C.; NMR ($d_6$-DMSO); 1.07(t, 3H), 1.23(t, 3H), 2.58(q, 2H), 3.05(q, 2H), 5.45(s, 2H), 6.62(d, 1H), 6.8-7.8(complex m, 24H), 8.22(d, 1H); mass spectrum (+ve FAB, methanol/NBA): 679 (M+H)+; microanalysis, found: C, 77.4; H, 5.7; N, 12.0%; $C_{45}H_{38}N_6O.H_2O$ requires: C, 77.5; H, 5.7; N, 12.1%.

EXAMPLE 3

Using an analogous procedure to that described in Example 2, but starting from 5,7-diethyl-1-[(2'-(2-triphenylmethyl-2H-tetrazol-5-yl)biphenyl-4-yl)methyl]-1,2,3,4-tetrahydro-1,6-naphthyridin-2-one (A), there was obtained 5,7-diethyl-1-[(2'-(1H-tetrazol-5-yl)biphenyl-4-yl)methyl]-1,2,3,4-tetrahydro-1,6-naphthyridin-2-one hydrochloride (70% yield), as a solid, m.p. 257°–260° C. (decomposition); NMR ($d_6$-DMSO): 1.2(m,6H), 2.7–3.2(m,8H), 5.25(s,2H), 7.05(d,2H), 7.15(s,1H), 7.25(d,2H), 7.4–7.75(m,4H); mass spectrum (+ve FAB, methanol/nitrobenzyl alcohol): 439(M+H)+; microanalysis, found: C, 65.2; H, 5.7; N, 17.7%; $C_{26}H_{26}N_6O.HCl.0.2H_2O$ requires C, 65.1; H, 5.7; N, 17.5%.

The starting material A was obtained as follows:

(i) A solution of ethyl-3-[(4-amino-2,6-diethyl)pyridin-3-yl]acrylate (540 mg) (prepared as described in Example 2, part (v)) in ethanol (30 ml) was catalytically hydrogenated over 30% palladium on carbon. When uptake of hydrogen ceased the catalyst was removed by filtration through diatomaceous earth. The filtrate was concentrated by evaporation and the residue was purified by flash chromatography, eluting with dichloromethane/methanol (9:1 v/v), to give 5,7-diethyl-1,2,3,4-tetrahydro-1,6-naphthyridin-one (B) (380 mg), as a solid, m.p. 100° C.; NMR (CDCl₃): 1.15°–1.4(m,6H), 2.6–2.9(m,6H), 2.95(t,2H), 6.45(s,1H), 8.5(broad s,1H); mass spectrum (chemical ionisation, ammonia): 205(M+H)+.

(ii) 5,7-diethyl-1,2,3,4-tetrahydro-1,6-naphthyridin-2-one (B) (300 mg) was added to a suspension of sodium hydride (60% dispersion in mineral oil; 90 mg) in DMF (20 ml) and the mixture was stirred for 1 hour. 5-[2-(4'-Bromomethylbiphenylyl)]-2-triphenylmethyl-2H-tetrazole (1.8 gm) was added and the mixture was stirred for 2.5 hours. Solvent was removed by evaporation and the residue was partitioned between ethyl acetate and water. The organic layer was separated, washed with water, saturated sodium chloride solution and dried (MgSO₄). Solvent was removed by evaporation and the residue was purified by flash chromatography eluting with ethyl acetate/hexane (1:1 v/v, increasing to 7:3 v/v) to give 5,7-diethyl-1-[(2'-(2-triphenylmethyl-2H-tetrazol-5-yl)biphenyl-4-yl)methyl]-1,2,3,4-tetrahydro-1,6-naphthyridin-2-one (A) (890 mg), as a foam; NMR (CDCl₃): 1.1(t,3H), 1.25(t,3H), 2.55(q,2H), 2.7–2.9(m,4H), 2.9–3.05(m,2H), 5.05(s,2H), 6.5(s,1H), 6.85–7.15(complex m,10H), 7.2–7.55(complex m,12H), 7.9(m,1H); mass spectrum (+ve FAB; DMSO/methanol/nitrobenzyl alcohol): 1362.8(2M+H)+, 681.5(M+H)+.

5,7-Diethyl-1,2,3,4-tetrahydro-1,6-naphthyridin-2-one was alternatively prepared according to the following procedure:

Procedure 3

5,7-Diethyl-1,6-naphthyridin-2(1H)-one (1 g) was dissolved in acetic acid (25 ml) and ethanol (25 ml) and catalytically hydrogenated over 10% palladium on carbon at 20 atmospheres pressure and 70° C. for 16 hours. The catalyst was removed by filtration through diatomaceous earth and the filtrate was concentrated by evaporation. Water (20 ml) was added to the residue and the mixture was basified by addition of solid potassium carbonate. The solution was extracted twice with ethyl acetate and the combined extracts were washed with saturated sodium chloride solution and dried (MgSO₄). The solvent was removed by evaporation to give an oil which solidified on standing. The solid was recrystallised from petroleum ether to give 5,7-diethyl-1,2,3,4-dihydro-1,6-naphthyridin-2-one (0.4 g) as a solid, m.p. 103°–105° C.; NMR (CDCl₃): 1.24(t, 3H), 1.27(t, 3H), 2.6–2.85(complex m, 6H), 2.95(dd, 2H), 6.46(s, 1H), 8.9(broad, 1H); mass spectrum (CI): 205 (M+H)+; microanalysis, found: C, 70.3; H, 7.9; N, 13.7%; $C_{12}H_{16}N_2O$ requires: C, 70.6; H, 7.9; N, 13.7%.

EXAMPLE 4

Using an analogous procedure to that described in Example 2, but starting from 4-chloro-5,7-diethyl-1-[(2'-(2-triphenylmethyl-2H-tetrazol-5-yl)biphenyl-4-yl)methyl]-1,6-napthyridin-2(1H)-one (A) (400 mg) there was obtained 4-chloro-5,7-diethyl-1-[(2'-(1H-tetrazol-5-yl)biphenyl-4-yl)methyl]-1,6-naphthyridin-2(1H)-one hydrochloride (120 mg); m.p. 243°–247° C. (ethanol/ether); NMR ($d_6$-DMSO): 1.2(t, 3H), 1.37(t, 3H), 2.97(q, 2H), 3.6(q, 2H), 5.55(s, 2H), 7.07(d, 2H), 7.15–7.75(complex m, 8H); mass spectrum (+ve FAB, methanol/NBA): 471 (M+H)+; microanalysis, found: C, 60.4; H, 4.9; N, 15.9%; $C_{26}H_{23}ClN_6O.HCl.0.5H_2O$ requires: C, 60.4; H, 4.6; N, 16.3%.

The starting material A was obtained as follows:

(i) Diethyl malonate (14.5 ml) and methyl 4-amino-2,6-diethylpyridine-3-carboxylate (21.3 g) was added to a solution of sodium (2.33 g) in ethanol (60 ml) and the resulting mixture was heated at 150° C. for 20 hours in an autoclave. The mixture was allowed to cool and then volatile material was removed by evaporation and the resultant semi-crystalline solid was triturated with ether. The solid was collected by filtration and dissolved in a minimum of water. The solution was acidified with 2M hydrochloric acid and the resulting precipitate was collected by filtration and washed with water. The solid was dried under vacuum to give ethyl 5,7-diethyl-4-hydroxy-2-oxo-1,2-dihydro-1,6-naphthyridine-3-carboxylate (B) (12.72 g); m.p. 240°–242° C.; NMR (CDCl₃): 1.34(dt, 6H), 1.52(t, 3H), 2.84(q, 2H), 3.36(q, 2H), 4.52(q, 2H), 6.87(s, 1H), 7.26(s, 1H), 11.41(broad, 1H); mass spectrum (CI, ammonia): 291 (M+H)+; microanalysis, found: C, 62.1; H, 6.2; N, 9.7%; $C_{15}H_{18}N_2O_4$ requires: C, 62.1; H, 6.3; N, 9.7%.

(ii) Compound B (1 g) was dissolved in a mixture of water (1 ml), 1,4-dioxan (2 ml) and concentrated hydrochloric acid (1 ml) and the mixture was heated at reflux for 3 hours. The reaction mixture was then cooled and the suspended solid was collected by filtration. The solid was washed with ethanol and ether and dried under vacuum to give 5,7-diethyl-4-hydroxy-1,6-naphthyridin-2(1H)-one (C) (0.42 g), m.p. 322°–325° C.; NMR ($d_6$-DMSO): 1.3(dt, 6H), 2.99(q, 2H), 3.47(q, 2H), 6.0(s, 1H), 7.28(s, 1H), 12.3(s, 1H); mass spectrum (CI, ammonia): 219 (M+H)+; microanalysis, found: C, 55.7; H, 5.9; N, 10.5%; $C_{12}H_{14}N_2O_2.HCl.0.25H_2O$ requires: C, 55.6; H, 5.6; N, 10.8%.

(iii) Compound C (17.6 g) was dissolved in phosphorus oxychloride (100 ml) and the mixture was heated at reflux for 24 hours. Unreacted phosphorus oxychloride was removed by evaporation and the residue was dissolved in concentrated hydrochloric acid (100 ml) containing water (15 ml). The mixture was heated at reflux for 4 hour. The mixture was then diluted with water (500 ml) and basified with solid potassium carbonate.

The resulting precipitate was collected by filtration and washed with water. The solid was purified by flash chromatography, eluting with ethyl acetate, to give 4-chloro-5,7-diethyl-1,6-naphthyridin-2(1H)-one (D) (8.9 g); m.p. 172°-174° C.; NMR (CDCl$_3$): 1.35(dt, 6H), 2.86(q, 2H), 3.49(q, 2H), 6.83(s, 1H), 7.0(s, 1H), 12.4(broad, 1H); mass spectrum (CI, ammonia): 237 (M+H)$^+$; microanalysis, found: C, 60.3; H, 5.5; N, 11.5%; C$_{12}$H$_{13}$ClN$_2$O requires: C, 60.9; H, 5.5; N, 11.8%.

(iv) Sodium hydride (50% dispersion in oil; 50 mg) was added to a stirred solution of compound D (236 mg) in DMF (5 ml) and the mixture was stirred under argon until effervescence ceased. 5-[2-(4'-Bromomethylbiphenylyl)]-2-triphenylmethyl-2H-tetrazole (680 mg) was added and the mixture was stirred for 16 hours. The mixture was then poured into water and extracted with ethyl acetate. The combined extracts were washed with water, saturated sodium chloride solution and dried (MgSO$_4$). Solvent was removed by evaporation to give an oil. The oil was purified by flash chromatography, eluting with ethyl acetate/petrol (3:7 v/v, increasing to 4:6 v/v), to give 4-chloro-5,7-diethyl-1-[(2'-(2-triphenylmethyl-2H-tetrazol-5-yl)biphenyl-4-yl)methyl]-1,6-naphthyridin-2-(1H)-one (A) as a solid (242 mg); m.p. 165°-167° C. (ethyl acetate/petroleum ether); NMR (CDCl$_3$): 1.42(t, 3H), 1.36(t, 3H), 2.66(q, 2H), 3.47(q, 2H), 5.38(s, 2H), 6.8-7.95(complex m, 25H); mass spectrum (+ve FAB, methanol/NBA): 713 (M+H)$^+$; microanalysis, found: C, 74.7; H, 5.1; N, 11.6%; C$_{45}$H$_{37}$ClN$_6$O.0.5H$_2$O requires C, 74.8; H, 5.3; N, 11.6%.

EXAMPLE 5

A mixture of 4-chloro-5,7-diethyl-1-[(2'-(2-triphenylmethyl2H-tetrazol-5-yl)biphenyl-4-yl)methyl]-1,6-naphthyridin-2(1H)-one (1.0 g), water (10 ml), DMSO (20 ml) and sodium hydroxide (1 g) was stirred and heated at reflux for one hour. The resulting mixture was diluted with water (50 ml), acidified with acetic acid and then extracted twice with ethyl acetate. The combined extracts were washed with water, saturated sodium chloride solution and then dried (MgSO$_4$). Volatile material was removed by evaporation to give a solid, which was washed with ether and collected by filtration. A mixture of the solid (0.2 g), methanol (4 ml) and concentrated hydrochloric acid (1 ml) was stirred for one hour and then volatile material was removed by evaporation. The residue was purified by repeated precipitation from a methanolic solution with ether to give 5,7-diethyl-4-hydroxy-1-[(2'-(1H-tetrazol-5-yl)biphenyl-4-yl)methyl]-1,6-naphthyridin-2(1H)-one hydrochloride (0.11 g); m.p. 222°-225° C.; NMR (d$_6$-DMSO): 1.21(t, 3H), 1.31(t, 3H), 2.93(q, 2H), 3.47(q, 2H), 5.51(s, 2H), 6.21(s, 1H), 7.06(d, 2H), 7.18(d, 2H), 7.4-7.75(complex m, 5H); mass spectrum (+ve FAB, methanol/NBA): 453 (M+H)$^+$; microanalysis, found: C, 62.0; H, 5.2; N, 16.7%; C$_{26}$H$_{24}$N$_6$O$_2$.HCl.H$_2$O requires: C, 61.6; H, 5.3; N, 16.6%.

EXAMPLE 6

Using an analogous procedure to that described in Example 2, but starting from 7-ethyl-5-methyl-4-phenyl-1-[2'-(2-triphenylmethyl2H-tetrazol-5-yl)biphenyl-4-yl)methyl]-1,6-naphthyridin-2(1H)-one (A) (0.6 g), there was obtained 7-ethyl-5-methyl-4-phenyl-1-[(2'-(1Htetrazol-5-yl)biphenyl-4-yl)methyl]-1,6-naphthyridin-2(1H)-one hydrochloride (0.07 g) as a solid, m.p. 210°-213° C. (after repeated precipitation from a methanolic solution with ether); NMR (d$_6$-DMSO): 1.20(t, 3H), 2.09(s, 3H), 2.91(q, 2H), 5.61(s, 2H), 6.68(s, 1H), 7.08(d, 2H), 7.25(d, 2H), 7.4-7.75(complex m, 10H); mass spectrum (+ve FAB, methanol/NBA): 499 (M+H)$^+$; microanalysis, found: C, 68.5; H, 5.0; N, 15.4%; C$_{31}$H$_{26}$N$_6$O.HCl.0.5H$_2$O requires: C, 68.4; H, 5.2; N, 15.5%.

The starting material A was obtained as follows:

(i) A mixture of 3-amino-1-phenyl-2-buten-1-one (2.3 g) and 5-(1-hydroxypropylidene)-2,2-dimethyl-1,3-dioxane-4,6-dione (4.0 g) was heated at 120° C. for 1 hour. The mixture was cooled to ambient temperature and the residue was purified by flash chromatography eluting with dichloromethane/methanol (19:1 v/v), to give 3-benzoyl-6-ethyl-2-methyl-4-oxo-1,4-dihydropyridine (B) (0.15 g) as a solid, m.p. 203° C.; NMR (d$_6$-DMSO): 1.2(t, 3H), 2.07(s, 3H), 2.5(q, 2H), 5.96(s, 1H), 7.44-7.50(m, 2H), 7.57-7.60(m, 1H), 7.72-7.76(m, 2H), 11.3(broad s, 1H); mass spectrum (CI, ammonia): 242(M+H)$^+$.

(ii) Tosyl isocyanate (0.66 ml) was added to a stirred suspension of compound B (0.48 g) in acetonitrile and the mixture was heated at reflux for 2.5 hours. The mixture was cooled to ambient temperature and the product was collected by filtration to give 3-benzoyl-6-ethyl-2-methyl-4-(tosylamino)pyridine (C) (0.65 g) as a solid, m.p. 244°-246° C.; NMR (d$_6$-DMSO): 1.19(t, 3H), 2.13(s, 3H), 2.31(s, 3H), 2.65(q, 2H), 7.08(s, 1H), 7.15(d, 2H), 7.32(d, 2H), 7.50-7.68(m, 5H), 12.63(s, 1H); mass spectrum (+ve FAB, glycerol/methanol): 395(M+H)$^+$.

(iii) Compound C (1.4 g) was added to concentrated sulphuric acid (6 ml) and the mixture was stirred and heated at 55° C. for 1.5 hours. The reaction mixture was cooled to ambient temperature and poured onto crushed ice. The mixture was then basified by addition of solid potassium carbonate and then extracted with dichloromethane. The combined extracts were dried (MgSO$_4$) and solvent was removed by evaporation to leave a solid. The solid was washed with petroleum ether and collected by filtration to give 4-amino-3-benzoyl-6-ethyl-2-methylpyridine (D) (0.6 g); NMR (d$_6$-DMSO): 1.19(t, 3H), 1.97(s, 3H), 2.55(q, 2H), 5.85(s, 2H), 6.41(s, 1H), 7.45-7.75(complex m, 5H); mass spectrum (CI, ammonia): 241(M+H)$^+$; and which was used without further purification.

(iv) Compound D (452 mg) and (carbethoxymethylene)triphenylphosphorane (0.77 g) were added to xylene (50 ml) and the mixture was heated at reflux for 16 hours. A further quantity of (carbethoxymethylene)triphenylphosphorane (0.77 g) was added and heating at reflux was continued for a further 24 hours. Volatile material was removed by evaporation and the residue was purified by flash chromatography, eluting with acetic acid/ethyl acetate (3:97 v/v), to give 7-ethyl-5-methyl-4-phenyl-1,6-naphthyridin-2(1H)-one (E) (240 mg), m.p. 221°-223° C. (after recrystallisation from ethyl acetate/petroleum ether): NMR (d$_6$-DMSO): 1.22(t, 3H), 1.89(s, 3H), 2.70(q, 2H), 6.22(s, 1H), 7.02(s, 1H), 7.3-7.55(complex m, 5H), 12.00(broad, 1H); mass spectrum (CI, ammonia): 265 (M+H)$^+$; microanalysis, found: C, 75.1; H, 5.9; N, 10.3; C$_{17}$H$_{16}$N$_2$O.0.5H$_2$O requires: C, 74.7; H, 6.2; N, 10.3%.

(v) Compound E was alkylated with 5-[2-(4'-bromomethylbiphenylyl)]-2-triphenylmethyl-2H-tetrazole, using an analogous procedure to that described in Example 4, part (iv), to give 7-ethyl-5-methyl-4-phenyl-1-[2'-(2-triphenylmethyl-2H-tetrazol-5-yl)biphenyl-4-yl)methyl]-1,6-naphthyridin-2(1H)-one in 50% yield; m.p. 168°-170° C.; NMR (d$_6$-DMSO): 1.07(t, 3H), 1.95(s, 3H), 2.58(q, 2H), 5.54(s, 2H), 6.51(s, 1H), 6.8-7.8-(complex m, 29H); mass spectrum (+ve FAB, methanol/NBA): 741 (M+H)$^+$; microanalysis, found: C, 80.6; N, 5.4; N, 11.2%; C$_{50}$H$_{40}$N$_6$O requires: C, 81.1; N, 5.4; N, 11.3%.

EXAMPLE 7

Methyl 4-[(4-chloro-5,7-diethyl-2-oxo-1,2-dihydro-1,6-naphthyridin-1-yl)methyl]benzoate (A) (300 mg) was dissolved in a mixture of dioxan (4 ml), water (1 ml) and concentrated hydrochloric acid (1 ml) and the resulting mixture was heated at reflux for 16 hours. Volatile material was removed by evaporation and toluene was added to the residue. Volatile material was again removed by evaporation. The solid residue was recrystallised from ethanol/ether to give 4-[(4-chloro-5,7-diethyl-2-oxo-1,2-dihydro-1,6-naphthyridin-1-yl)methyl]benzoic acid (180 mg), m.p. 250°-253° C.; NMR (d$_6$-DMSO): 1.81(t, 3H), 1.37(t, 3H), 2.92(q, 2H), 3.62(q, 2H), 5.65(s, 2H), 7.23(s, 1H), 7.37(d, 2H), 7.48(s, 1H), 7.88(d, 2H); mass spectrum (CI, ammonia): 370 (M$^+$); microanalysis, found: C, 58.6; H, 5.1; N, 6.7%; C$_{20}$H$_{19}$ClN$_2$O$_3$ requires: C, 59.0; H, 4.9; N, 6.9%.

The starting material A was obtained as follows:

Sodium hydride (50% dispersion in oil, 225 mg) was added to a stirred solution of 4-chloro-5,7-diethyl-1,6-naphthyridin-2(1H)-one (944 mg) in DMF (20 ml) under an atmosphere of argon and the mixture was stirred until effervescence ceased. Methyl 4-bromomethylbenzoate (1 g) was added and the mixture was stirred for 16 hours. The reaction mixture was poured into water and extracted twice with ethyl acetate. The combined extracts were washed with water, dried (MgSO$_4$) and the solvent removed by evaporation to leave a solid. The solid was purified by flash chromatography, eluting with ethyl acetate/petroleum ether (2:3 v/v) to give methyl 4-[(4-chloro-5,7-diethyl-2-oxo-1,2-dihydro-1,6-naphthyridin-1-yl)methyl]benzoate (A) as a yellow-orange solid (780 mg), m.p. 126° C. (after recrystallisation from petroleum ether); NMR (CDCl$_3$): 1.8(t, 3H), 1.37(t, 3H), 2.73(q, 2H), 3.48(q, 2H), 3.9(s, 3H), 5.52(s, 2H), 6.78(s, 1H), 6.93(s, 1H), 7.26(d, 2H), 7.99(d, 2H); mass spectrum (CI, ammonia): 385 (M+H)$^+$; microanalysis, found: C, 65.8; H, 5.6; N, 7.1%; C$_{21}$H$_{21}$ClN$_2$O$_3$ requires: C, 65.5; H, 5.5; N, 7.3%. 1

EXAMPLE 8

Methyl 4-[(5,7-diethyl-2-oxo-4-phenylthio-1,2-dihydro-1,6-naphthyridin-1-yl)methyl]benzoate (A) (250 mg) was dissolved in ethanol (10 ml) and sodium hydroxide (250 mg) and water (1 ml) was added. The mixture was heated at reflux for 3 hours and then volatile material was removed by evaporation. The residue was dissolved in water (10 ml) and the aqueous solution acidified to pH 4 with acetic acid. The aqueous mixture was then extracted twice with ethyl acetate and the combined extracts were washed with saturated sodium chloride solution and dried (MgSO$_4$). The solvent was removed by evaporation and the residue was recrystallised first from ethyl acetate/THF/petroleum ether and then from ethanol/ether/petroleum ether to give 4-[(4-ethoxy-5,7-diethyl-2-oxo-1,2-dihydro-1,6-naphthyridin-1-yl)methyl]benzoic acid (40 mg) as a solid, m.p. 254°-256° C.; NMR (d$_6$-DMSO): 1.09(t, 3H), 1.22(t, 3H), 1.48(t, 3H), 2.64(q, 2H), 2.22(q, 2H), 4.23(q, 2H), 5.51(s, 2H), 6.08(s, 1H), 6.97(s, 1H), 7.28(d, 2H), 7.87(d, 2H), 12.85(broad, 1H); mass spectrum (CI, ammonia): 381(M+H)$^+$; microanalysis, found: C, 68.2; H, 6.4; N, 7.3%; C$_{20}$H$_{20}$N$_2$O$_4$ requires: C, 68.2; H, 5.7; N, 7.9%.

The starting material A was obtained as follows:

Sodium hydride (50% dispersion in oil; 60 mg) was added to a solution of thiophenol (120 mg) in dimethylacetamide (DMA) (10 ml) and the mixture was stirred until effervescence ceased. Methyl 4-[(4-chloro-5,7-diethyl-2-oxo-1,2-dihydro-1,6-naphthyridin-1-yl)methyl]benzoate (384 mg) was added and the resulting mixture was stirred at 50° C. for 3 hours. The reaction mixture was then poured into water and extracted twice with ethyl acetate. The combined extracts were washed with water, saturated sodium chloride solution and dried (MgSO$_4$). Solvent was removed by evaporation and the residue oil was purified by flash chromatography, eluting with ethyl acetate/petroleum ether (2:3 v/v), to give methyl 4-[(5,7-diethyl-2-oxo-4-phenylthio-1,2-dihydro-1,6-naphthyridin-1-yl)methyl]benzoate (A) (290 mg) as a solid, m.p. 150°-152° C. (after recrystallisation from ethyl acetate/petroleum ether); NMR (CDCl$_3$): 1.19(t, 3H), 1.49(t, 3H), 2.76(q, 2H), 3.59(q, 2H), 3.89(s, 3H), 5.47(s, 2H), 6.08(s, 1H), 6.75(s, 1H), 7.24(d, 2H), 7.5-7.7(complex m, 5H), 7.97(d, 2H); mass spectrum (CI, ammonia): 459 (M+H)$^+$; microanalysis, found: C, 70.2; H, 5.7; N, 6.1%; C$_{27}$H$_{26}$N$_2$O$_3$S requires: C, 70.7; H, 5.7; N, 6.1%.

EXAMPLE 9

Methyl 4-[(5,7-diethyl-2-oxo-4-phenylthio-1,2-dihydro-1,6-naphthyridin-1-yl)methyl]benzoate (200 mg) was dissolved in a mixture of dioxan (4 ml), water (1 ml) and concentrated hydrochloric acid (1 ml) and the mixture was heated at reflux for 4 hours. Volatile material was then removed by evaporation and toluene was added to the residue. Volatile material was again removed by evaporation. The solid residue was recrystallised from ethanol/ether to give 4-[(5,7-diethyl-2-oxo-4-phenylthio-1,2-dihydro-1,6-naphthyridin-1-yl)methyl]benzoic acid (120 mg) m.p. 260°-262° C.; NMR (d$_6$-DMSO): 1.19(t, 3H), 1.51(t, 3H), 2.98(q, 2H), 3.72(q, 2H), 5.56(s, 2H), 5.91(s, 1H), 7.35(d, 2H), 7.47(s, 1H), 7.6-7.8(complex m, 5H), 7.88(d, 2H); mass spectrum (CI, ammonia): 445(M+H)$^+$; microanalysis, found: C, 64.5; H, 5.4; N, 5.9%; C$_{26}$H$_{24}$N$_2$O$_3$S requires: C, 64.9; H, 5.2; N, 5.8%.

EXAMPLE 10

Ethyl 5,7-diethyl-2-oxo-1-[(2'-(2-triphenylmethyl-2H-tetrazol-5-yl)biphenyl-4-yl)methyl]-1,2-dihydro-1,6-naphthyridin-3-carboxylate (A) (0.42 g) was added to a mixture of methanol (5 ml), dichloromethane (1 ml) and concentrated hydrochloric acid (0.15 ml) and the mixture was stirred for 20 minutes. Volatile material was removed by evaporation and the residue was triturated with ether to give a white solid. The solid was purified by dissolution in hot ethanol and precipitation by adding ether to give ethyl 5,7-diethyl-2-oxo-1-[(2'-(1H-tetrazol-5-yl)biphenyl-4-yl)methyl]-1,2-dihydro-1,6-naphthyridine-3-carboxylate hydrochloride (0.186 g); NMR (d$_6$-DMSO): 1.25(t, 3H), 1.32(t, 3H), 1.34(t, 3H), 2.95(q, 2H), 3.35(q, 2H), 4.34(q, 2H), 5.55(s, 2H), 7.07(d, 2H), 7.21(d, 2H), 7.4-7.8(complex m, 6H), 8.7(s, 1H); mass spectrum (+ve FAB, DMSO/NBA): 509 (M+H)$^+$; microanalysis, found: C, 62.5; H, 5.6; N, 14.8%; C$_{29}$H$_{28}$N$_6$O$_3$.HCl.0.14 (CH$_3$CO$_2$C$_2$H$_5$).0.5 H$_2$O requires: C, 62.6; H, 5.5; N, 14.8%.

(i) The starting material A was obtained as follows:

4-amino-2,6-diethylpyridine-3-carbaldehyde (1.78 g), diethylmalonate (1.92 g), ethanol (15 ml) and piperidine (4 drops) were heated at reflux for 16 hours. Volatile material was removed by evaporation and the residue was recrystallised from ethyl acetate/petroleum ether to give ethyl 5,7-diethyl-2-oxo-1,2-dihydro-1,6-naphthyridine-3-carboxylate (B) (1.4 g), m.p. 159°–160° C.; NMR (CDCl$_3$): 1.34(t, 3H), 1.38(t, 3H), 1.47(t, 3H), 2.87(q, 2H), 3.14(q, 2H), 4.47(q, 2H), 7.03(s, 1H), 8.78(s, 1H), 12.2(s, 1H); mass spectrum (CI, ammonia): 275 (M+H)$^+$; microanalysis, found: C, 65.8; H, 6.8; N, 10.4%; C$_{15}$H$_{18}$N$_2$O$_3$ requires: C, 65.7; H, 6.6; N, 10.2%.

(ii) A solution of compound B (0.822 g) in DMF (10 ml) was added dropwise to a stirred suspension of sodium hydride (50% dispersion in oil, 0.158 g) in DMF (3 ml) and the mixture was stirred until effervescence ceased. A solution of 5-[2-(4'-bromomethylbiphenylyl)]-2-triphenylmethyl-2H-tetrazole (2.1 g) in DMF (15 ml) was then added dropwise and the resulting mixture was stirred for 16 hours. Volatile material was removed by evaporation and the residue was partitioned between ethyl acetate and water. The organic phase was separated, dried (MgSO$_4$) and solvent was removed by evaporation to give an oil. The oil was purified by flash chromatography, eluting with ethyl acetate/petroleum ether (3:1 v/v) to give ethyl 5,7-diethyl-2-oxo-1-[(2'-(2-triphenylmethyl-2H-tetrazol-5-yl)biphenyl-4-yl)methyl]-1,2-dihydro-1,6-naphthyridine-3-carboxylate (A) (1.32 g) as a solid, m.p. 110°–112° C.; NMR (CDCl$_3$): 1.17(t, 3H), 1.36(t, 3H), 1.44(t, 3H), 2.69(q, 2H), 3.13(q, 2H), 4.46(q, 2H), 5.4(s, 2H), 6.8(s, 1H), 6.85–8.0(complex m, 23H), 8.71(s, 1H); mass spectrum (+ve FAB): 751 (M+H)$^+$; microanalysis, found: C, 76.4; H, 5.8; N, 10.9%; C$_{48}$H$_{42}$N$_6$O$_3$ requires: C, 76.8; H, 5.6; N, 11.2%.

EXAMPLE 11

5,7-Diethyl-2-oxo-1-[(2'-(2-triphenylmethyl-2H-tetrazol-5-yl)biphenyl-4-yl)methyl]-1,2-dihydro-1,6-naphthyridine-3-carboxylic acid (A) (165 mg) was dissolved in a mixture of methanol (4 ml), dichloromethane (1 ml) and concentrated hydrochloric acid (0.1 ml) and the mixture was stirred for 15 minutes. Volatile material was then removed by evaporation. The residue was dissolved in methanol (2 ml) and a solid was precipitated by the addition of ether. The solid was collected by filtration and purified by repeated precipitation from methanolic solution with ether to give 5,7-diethyl-2-oxo-1-[(2'-(1H-tetrazol-5-yl)biphenyl-4-yl)methyl]-1,2-dihydro-1,6-naphthyridin-3-carboxylic acid hydrochloride (75 mg) as a solid; NMR (d$_6$-DMSO+d$_4$-acetic acid): 1.24(t, 3H), 1.34(t, 3H), 2.89(q, 2H), 3.29(q, 2H), 5.64(s, 2H), 7.1(d, 2H), 7.25(d, 2H), 7.41(s, 1H), 7.45–7.75(complex m, 4H), 8.95(s, 1H); mass spectrum (+ve FAB, methanol/NBA): 481 (M+H)$^+$; microanalysis, found: C, 57.8; H, 5.0; N, 14.3%; C$_{27}$H$_{24}$N$_6$O$_3$·HCl·2.5H$_2$O·0.1(CH$_3$CO$_2$C$_2$H$_5$) requires: C, 57.6; H, 5.4; N, 14.7%.

The starting material A was obtained as follows:

Ethyl 5,7-diethyl-2-oxo-1-[(2'-(2-triphenylmethyl-2H-tetrazol-5-yl)biphenyl-4-yl)methyl]-1,2-dihydro-1,6-naphthyridine-3-carboxylate (0.41 g) was dissolved in dioxan (5 ml) containing aqueous 1M sodium hydroxide solution (0.55 ml) and the mixture was stirred for 16 hours. Volatile material was removed by evaporation and the residue was partitioned between ethyl acetate and water. The aqueous phase was separated, acidified to pH 4–5 with 1M aqueous citric acid solution and then extracted twice with dichloromethane. The combined extracts were dried (MgSO$_4$) and the solvent was removed by evaporation. The residue was purified by flash chromatography, eluting initially with ethyl acetate/petroleum ether (2:1 v/v), followed by ethyl acetate and then methanol/ethyl acetate (1:9 v/v), to give 5,7-diethyl-2-oxo-1-[(2'-(2-triphenylmethyl-2H-tetrazol-5-yl)biphenyl-4-yl)methyl]-1,2-dihydro-1,6-naphthyridine-3-carboxylic acid (A) (0.184 g) as a solid; NMR (d$_6$-DMSO+d$_4$-acetic acid): 1.15(t,3H), 1.32(t,3H), 2.68(q,2H), 3.22(q,2H), 5.66(s,2H), 6.8–7.9(complex m,24H), 9.06(s,1H); mass spectrum(+ve FAB, DMSO/NBA): 745(M+Na)$^+$; microanalysis, found: C, 66.9; H, 5.0; N, 10.0%; C$_{46}$H$_{38}$N$_6$O$_3$·1.7SiO$_2$ requires: C, 67.0; H, 4.6; N, 10.2%.

EXAMPLE 12

5,7-diethyl-2-oxo-1-[(2'-(2-triphenylmethyl-2H-tetrazol-5-yl)biphenyl-4-yl)methyl]-1,2-dihydro-1,6-naphthyridine-3-carboxamide (A) (500 mg) was dissolved in a mixture of methanol (5 ml), dichloromethane (3 ml) and concentrated hydrochloric acid (0.7 ml) and the mixture was stirred for 30 minutes. Volatile material was removed by evaporation and the residue was dissolved in a minimum of methanol. Ether was added to precipitate a solid which was collected by filtration. The solid was recrystallised from acetonitrile/methanol to give 5,7-diethyl-2-oxo-1-[(2'-(1H-tetrazol-5-yl)biphenyl-4-yl)methyl]-1,2-dihydro-1,6-naphthyridine-3-carboxamide hydrochloride (220 mg), m.p. 264° C. (dec); NMR (d$_6$-DMSO+d$_4$-acetic acid): 1.29(t, 3H), 1.39(t, 3H), 3.02(q, 2H), 3.42(q, 2H), 5.66(s, 2H), 7.1(d, 2H), 7.25(d, 2H), 7.45–7.75(complex m, 5H), 9.03(s, 1H); mass spectrum (+ve FAB, methanol/DMSO/NBA): 480 (M+H)$^+$; microanalysis, found: C, 61.7; H, 4.9; N, 18.7%; C$_{27}$H$_{25}$N$_7$O$_2$HCl·0.5H$_2$O requires: C, 61.7; H, 4.9; N, 18.6%.

The starting material A was obtained as follows:

Concentrated aqueous ammonia solution (d 0.88) was added dropwise to a solution of ethyl 5,7-diethyl-2-oxo-1-[(2'-(2-triphenylmethyl-2H-tetrazol-5-yl)biphenyl-4-yl)methyl]-1,2-dihydro-1,6-naphthyridine-3-carboxylate (600 mg) in a mixture of methanol (7 ml) and dichloromethane (1.5 ml) until the solution became cloudy. Dichloromethane (2 ml) was added to give a clear solution and the mixture was stirred for 3 days. Volatile material was then removed by evaporation to give 5,7-diethyl-2-oxo-1-[(2'-(2-triphenylmethyl-2H-tetrazol-5-yl)-biphenyl-4-yl)methyl]-1,2-dihydro-1,6-naphthyridine-3-carboxamide as a solid (500 mg), which was used without further purification or characterisation.

EXAMPLE 13

Using an analogous procedure to that described in Example 10, but starting from 5,7-diethyl-2-oxo-1-[(2'-(2-triphenylmethyl-2H-tetrazol-5-yl)biphenyl-4-yl)methyl]-1,2-dihydro-1,6-naphthyridine-3-N,N-diethylcarboxamide (A) (490 mg) there was thus obtained 5,7-diethyl-2-oxo-1-[(2'-(1H-tetrazol-5-yl)biphenyl-4-yl)methyl]-1,2-dihydro-1,6-naphthyridine-3-N,N-diethylcarboxamide hydrochloride (241 mg) as a solid, m.p. 174° C. (dec); NMR (d$_6$-DMSO+d$_4$-acetic acid): 1.07(t, 3H), 1.18(t, 3H), 1.27(t, 3H), 1.31(t, 3H), 2.96(q, 2H), 3.21(q, 2H), 3.33(q, 2H), 3.38(q, 2H), 5.58(s, 2H), 7.09(d, 2H), 7.23(d, 2H), 7.45–7.75(complex m, 5H), 8.4(s, 1H); mass spectrum (+ve FAB, methanol/NBA): 536 (M+H)$^+$; microanalysis, found: C, 64.6; H, 6.5; N, 16.4%;

$C_{31}H_{33}N_7O_2.HCl.0.1(CH_3CO_2C_2H_5).0.4 H_2O$ requires: C, 64.1; H, 6.1; N, 16.7%.

The starting material A was obtained as follows:

(i) Diethylamine (0.63 ml) was added dropwise to a stirred solution of trimethylaluminium (2M solution in toluene; 3 ml) in dichloromethane (5 ml) under an atmosphere of argon. The mixture was stirred for 30 minutes then a solution of ethyl 5,7-diethyl-2-oxo-1,2-dihydro-1,6-naphthyridine-3-carboxylate (548 mg) in dichloromethane (5 ml) was added dropwise. The resulting mixture was heated at reflux for 4 hours then cooled in ice. A mixture of 2M hydrochloric acid (1 ml) and methanol (1 ml) was added dropwise. The mixture was filtered and the filtrate was concentrated by evaporation to give a brown oil which was purified by flash chromatography, eluting with methanol/ethyl acetate (1:24 v/v), to give 5,7-diethyl-2-oxo-1,2-dihydro-1,6-naphthyridine-3-N,N-diethylcarboxamide (B) (391 mg) as a solid, m.p. 56°-59° C.; NMR (CDCl$_3$): 1.17(t, 3H), 1.25-1.4(complex m, 9H), 2.85(q, 2H), 3.07(q, 2H), 3.32(q, 2H), 3.63(q, 2H), 6.95(s, 1H), 8.08(s, 1H), 12.28(s, 1H); mass spectrum (CI, ammonia): 302 (M+H)+; microanalysis, found C, 66.4; H, 7.6; N, 13.6%; $C_{17}H_{23}N_3O_2.0.25H_2O$ requires: C, 66.7; H, 7.7; N, 13.7%.

(ii) Compound B (370 mg) was alkylated with 5-[2-(4'-bromomethylbiphenyl)]-2-triphenylmethyl-2H-tetrazole (900 mg) using a similar procedure to that described in Example 10, part (ii). The product was purified by flash chromatography, eluting with methanol/dichloromethane (1:19 v/v), followed by a second flash chromatography, eluting with methanol/ethyl acetate/petroleum ether (1:16:16 v/v/v) to give 5,7-diethyl-2-oxo-1-[(2'-(2-triphenylmethyl-2H-tetrazol-5-yl)biphenyl-4-yl)methyl-1,2-dihydro-1,6-naphthyridine-3-N,N-diethylcarboxamide (A) (580 mg) as a solid, m.p. 103°-109° C.; NMR (CDCl$_3$): 0.96(t, 3H), 1.18(t, 3H), 1.4(t, 6H), 2.9-3.35(complex m, 8H), 5.5(broad, 2H), 6.85-7.55(complex m, 23H), 7.93(complex m, 1H), 8.24(s, 1H); mass spectrum (+ve FAB, methanol/NBA): 778 (M+H)+; microanalysis, found: C, 76.7; H, 6.2; N, 12.5%; $C_{50}H_{47}N_7O_2.0.25H_2O$ requires: C, 76.7; H, 6.1; N, 12.5%.

EXAMPLES 14-18

Using an analogous procedure to that described in Example 10, but starting from the appropriate starting material of formula III wherein L is triphenylmethyl, the following compounds of formula I were obtained in yields of 55 to 100%:

(Example 14): 5,7-diethyl-3-nitro-1-[(2'-(1H-tetrazol-5-yl)biphenyl-4-yl)methyl]-1,6-naphthyridin-2(1H)-one hydrochloride as a solid; NMR (d$_6$-DMSO): 1.22(t, 3H), 1.30(t, 3H), 2.88(q, 2H), 3.25(q, 2H), 5.58(s, 2H), 7.08(d, 2H), 7.24(d, 2H), 7.4-7.75(complex m, 5H), 9.15(s, 1H); mass spectrum (+ve FAB, dMSO/glycerol): 482 (M+H)+; microanalysis, found: C, 58.5; H, 4.8; N, 17.7%; $C_{26}H_{23}N_2O_3.HCl.H_2O.0.1(CH_3CO_2C_2H_5)$ requires: C, 58.2; H, 4.9; N, 18.0%.

(Example 15): 5,7-diethyl-3-(2-pyridyl)-1-[(2'-(1H-tetrazol-5-yl)biphenyl-4-yl)methyl]-1,6-naphthyridin-2(1H)-one hydrochloride as a solid; NMR (d$_6$-DMSO+d$_4$-acetic acid): 1.30(t, 3H), 1.42(t, 3H), 3.05(q, 2H), 3.45(q, 2H), 5.71(s, 2H), 7.11(d, 2H), 7.30(d, 2H), 7.4-7.8(complex m, 6H), 8.25(t, 1H), 8.50(d, 1H), 8.88(d, 1H), 9.03(s, 1H); mass spectrum (+ve FAB, methanol/NBA): 514 (M+H)+; microanalysis, found: C, 61.6; H, 5.6; N, 15.8%; $C_{31}H_{27}N_2O.2HCl.H_2O.0.4(C_2H_5)_2O$ requires: C, 61.7; H, 5.2; N, 15.5%.

(Example 16): 3-cyano-5,7-diethyl-1-[(2'-(1H-tetrazol-5-yl)biphenyl-4-yl)methyl]-1,6-naphthyridin-2(1H)-one hydrochloride as a solid, m.p. >190° C. (dec); NMR (d$_6$-DMSO+d$_4$-acetic acid): 1.29(t, 3H), 1.37(t, 3H), 2.97(q, 2H), 3.34(q, 2H), 5.63(s, 2H), 7.15(d, 2H), 7.31(d, 2H), 7.5-7.8(complex m, 5H), 9.28(s, 1H); mass spectrum (+ve FAB, methanol/NBA): 462 (M+H)+; microanalysis, found: C, 64.5; H, 5.2; N, 19.0%; $C_{27}H_{23}N_7O.HCl.0.15(CH_3CO_2C_2H_5)$ requires: C, 64.6; H, 5.2; N, 18.9%.

(Example 17): 5,7-diethyl-3-(3-pyridyl)-1-[(2'-(1H-tetrazol-5-yl)biphenyl-4-yl)methyl]-1,6-naphthyridin-2(1H)-one as a solid, m.p. >170° C. (dec); NMR (d$_6$-DMSO): 1.28(t, 3H), 1.36(t, 3H), 3.04(q, 2H), 3.50(q, 2H), 5.66(s, 2H), 7.08(d, 2H), 7.30(d, 2H), 7.45-7.75-(complex m, 5H), 7.94(dd, 1H), 8.70(d, 1H), 8.73(s, 1H), 8.86(d, 1H), 9.21(d, 1H); mass spectrum (+ve FAB, methanol/NBA): 514 (M+H)+; microanalysis, found: C, 63.6; H, 5.2; N, 16.5%; $C_{31}H_{27}N_7O$ requires: C, 63.5; H, 5.0; N, 16.7%.

(Example 18): 5,7-diethyl-3-phenylsulphinyl-1-[(2'-(1H-tetrazol-5-yl)biphenyl-4-yl)methyl]-1,6-naphthyridin-2(1H)-one as a solid; m.p. 172° C. (decomp); NMR (d$_6$-DMSO): 1.22(t, 3H), 1.37(t, 3H), 2.91(q, 2H), 3.38(dq, 2H), 5.43(d, 1H), 5.51(d, 1H), 6.98(d, 2H), 7.07(d, 2H), 7.4-7.7(complex m, 8H), 7.84(complex m, 2H), 8.59(s, 1H); mass spectrum (+ve FAB, methanol/NBA): 561 (M+H)+; microanalysis, found: C, 64.1; H, 5.1; N, 14.2%; $C_{32}H_{28}N_6O_2S$ requires; C, 64.4; H, 4.9; N, 14.1%.

The starting materials of formula III used in Examples 14 to 18 were obtained in yields of 30 to 73% using a similar procedure to that described in Example 10, part (ii), starting from the appropriate compounds of formula IV as follows:

(Example 14A): 5,7-diethyl-3-nitro-1-[(2'-(2-triphenylmethyl-2H-tetrazol-5-yl)biphenyl-4-yl)methyl]-1,6-naphthyridin-2(1H)-one as a foam; NMR (CDCl$_3$): 1.20(t, 3H), 1.38(t, 3H), 2.75(q, 2H), 3.14(q, 2H), 5.45(s, 2H), 6.35-7.5(complex m, 23H), 7.9(m, 1H), 8.85(s, 1H); mass spectrum (+ve FAB, methanol/NBA): 724 (M+H)+; microanalysis, found: C, 74.3; H, 5.5; N, 12.6%; $C_{45}H_{37}N_7O_3$ requires: C, 74.7; H, 5.2; N, 13.5%.

(Example 15A): 5,7-diethyl-3-(2-pyridyl)-1-[(2'-(2-triphenylmethyl-2H-tetrazol-5-yl)biphenyl-4-yl)methyl]-1,6-naphthyridin-2(1H)-one as a solid, m.p. 79°-83° C.; NMR (d$_6$-DMSO): 1.12(t, 3H), 1.31(t, 3H), 2.62(q, 2H), 3.16(q, 2H), 5.58(s, 2H), 6.8-8.0(complex m, 26H), 8.45(dt, 1H), 8.75(dq, 1H), 8.98(s, 1H); mass spectrum (+ve FAB, DMSO/NBA): 756 (M+H)+; microanalysis, found: C, 79.5; H, 6.2; N, 11.7%; $C_{50}H_{41}N_7O$ requires: C, 79.4; H, 5.5; N, 13.0%.

(Example 16A): 3-cyano-5,7-diethyl-1-[(2'-(2-triphenylmethyl-2H-tetrazol-5-yl)biphenyl-4-yl)methyl]-1,6-naphthyridin-2(1H)-one as a solid, m.p. 111°-115° C. (dec); NMR (CDCl$_3$): 1.19(t, 3H), 1.36(t, 3H), 2.75(q, 2H), 3.10(q, 2H), 5.38(s, 2H), 6.8-7.5(complex m, 23H), 7.90(m, 1H), 8.5(s, 1H); mass spectrum (+ve FAB, DMSO/NBA); 704 (M+H)+.

(Example 17A): 5,7-diethyl-3-(3-pyridyl)-1-[(2'-(2-triphenylmethyl-2H-tetrazol-5-yl)biphenyl-4-yl)methyl]-1,6-naphthyridin-2(1H)-one as a foam; NMR (CDCl$_3$): 1.21(t, 3H), 1.40(t, 3H), 2.76(q, 2H), 3.19(q, 2H), 5.46(s, 2H), 6.85-7.5(complex m, 24H), 7.89(dd, 1H), 8.13(s, 1H), 8.18(ddd, 1H), 8.65(dd, 1H), 8.90(d, 1H); mass spectrum (+ve FAB, methanol/NBA): 756 (M+H)+; microanalysis, found: C, 79.0; H, 5.3; N, 12.8%; $C_{50}H_{41}N_7O$ requires: C, 79.4; H, 5.5; N, 13.0%.

(Example 18A): 5,7-diethyl-3-phenylsulphinyl-1-[(2'-(2-triphenylmethyl-2H-tetrazol-5-yl)biphenyl-4-yl)methyl]-1,6-naphthyridin-2(1H)-one as a solid, m.p. 94°-100° C.; NMR (CDCl$_3$): 1.15(t, 3H), 1.40(t, 3H), 2.69(q, 2H), 3.24(q, 2H), 5.25(d, 1H), 5.35(d, 1H), 6.75-7.55(complex m, 26H), 7.85-8.0(complex m, 3H), 8.70(s, 1H); mass spectrum (+ve FAB, methanol/NBA): 803 (M+H)$^+$; microanalysis, found: C, 75.8; H, 5.4; N, 10.6%; C$_{51}$H$_{42}$N$_6$O$_2$S requires: C, 76.3; H, 5.3; N, 10.5%.

The starting materials of formula IV used in Examples 14 to 18 were obtained as follows:

(Example 14B): Using an analogous procedure to that described in Example 10, part (i), but using ethyl 2-nitroacetate in place of diethylmalonate, there was thus obtained 5,7-diethyl-3-nitro-1,6-naphthyridin-2(1H)-one as a solid, in 57% yield; m.p. 213°-215° C. (dec); NMR (CDCl$_3$): 1.37(t, 3H), 1.40(t, 3H), 2.92(q, 2H), 3.15(q, 2H), 7.08(s, 1H), 8.93(s, 1H), 12.01(broad, 1H); mass spectrum (CI, ammonia): 248 (M+H)$^+$; microanalysis, found; C, 58.5; H, 5.3; N, 16.8%; C$_{12}$H$_{13}$N$_3$O$_3$ requires: C, 58.3; H, 5.3; N, 17.0%.

(Example 15B): Using an analogous procedure to that described in Example 10, part (i), but using ethyl 2-(2-pyridyl)acetate in place of diethylmalonate, there was thus obtained 5,7-diethyl-3-(2-pyridyl)-1,6-naphthyridin-2(1H)-one as a solid, in 37% yield; m.p. 141°-143° C.; NMR (d$_6$-DMSO): 1.26(t, 3H), 1.31(t, 3H), 2.76(q, 2H), 3.10(q, 2H), 6.96(s, 1H), 7.37(ddd, 1H), 7.84(dt, 1H), 8.49(dt, 1H), 8.69(dq, 1H), 8.90(s, 1H), 12.16(s, 1H); microanalysis, found: C, 71.3; H, 5.9; N, 14.6%; C$_{17}$H$_{17}$N$_3$O.0.5H$_2$O requires: C, 70.8; H, 6.2; N, 14.6%.

(Example 16B): Using an analogous procedure to that described in Example 10, part (i), but using ethyl 2-cyanoacetate in place of diethyl malonate, there was thus obtained 3-cyano-5,7-diethyl-1,6-naphthyridin-2(1H-one as a solid, in 50% yield; m.p. 258°-259° C.; NMR (CDCl$_3$): 1.36(t, 3H), 1.39(t, 3H), 2.92(q, 2H), 3.12(q, 2H), 7.11(s, 1H), 8.56(s, 1H), 12.4(broad, 1H).

(Example 17B): Using an analogous procedure to that described in Example 10, part (i), but starting from ethyl 2-(3-pyridyl)acetate in place of diethylmalonate and refluxing the reaction mixture for 5 days, there was thus obtained 5,7-diethyl-3-(3-pyridyl)-1,6-naphthyridin-2(1H)-one as a solid, in 61% yield; m.p. 231°-234° C.; NMR (CDCl$_3$+d$_6$-DMSO): 1.03(t, 3H), 1.08(t, 3H), 2.54(q, 2H), 2.83(q, 2H), 6.68(s, 1H), 7.10(m, 1H), 7.78(s, 1H), 7.83(m, 1H), 8.31(dd, 1H), 8.59(d, 1H), 11.65(broad, 1H); microanalysis, found: C, 72.7; H, 6.0; N, 15.2; C$_{17}$H$_{17}$N$_3$O requires: C, 73.1; H, 6.1; N, 15.0%.

(Example 18B): Using an analogous procedure to that described in Example 10, part (i), but starting from ethyl 2-(phenylsulphinyl)acetate in place of diethylmalonate, there was thus obtained 5,7-diethyl-3-phenylsulphinyl-1,6-naphthyridin-2(1H)-one as a solid, in 56% yieldp m.p.>230° C. (dec); NMR (d$_6$-DMSO): 1.23(t, 3H), 1.32(t, 3H), 2.75(q, 2H), 3.15(q, 2H), 6.96(s, 1H), 7.5-7.9(complex m, 5H), 8.46(s, 1H), 12.3(broad, 1H); mass spectrum (CI, ammonia): 327 (M+H)$^+$; microanalysis, found: C, 65.7; H, 5.5; N, 8.1%; C$_{18}$H$_{18}$N$_2$O$_2$S requires: C, 66.2; H, 5.5; N, 8.6%.

EXAMPLE 19

Methyl 4-[(5,7-diethyl-2-oxo-3-phenylsulphinyl-1,2-dihydro-1,6-naphthyridin-1-yl)methyl]benzoate (A) (474 mg) was suspended in a mixture of methanol (6 ml) and 1M aqueous sodium hydroxide solution (3 ml) and the mixture was heated at reflux for 2 hours. The mixture was then cooled and partitioned between water (50 ml) and dichloromethane (10 ml). The aqueous phase was separated and acidified with acetic acid. The resultant precipitate was collected by filtration and dried under vacuum to give 4-[(5,7-diethyl-2-oxo-3-phenylsulphinyl-1,2-dihydro-1,6-naphthyridin-1-yl)methyl]benzoic acid (338 mg) as a solid; NMR (d$_6$-DMSO): 1.14(t, 3H), 1.32(t, 3H), 2.72(q, 2H), 3.20(q, 2H), 5.45(d, 1H), 5.55(d, 1H), 7.16(s, 1H), 7.19(d, 2H), 7.54(m, 3H), 7.82(m, 4H),8.58(s, 1H), 12.87(broad, 1H); mass spectrum (+ve FAB, methanol/DMSO/NBA): 461 (M+H)$^+$; microanalysis, found: C, 67.7; H, 5.3; N, 6.2%; C$_{26}$H$_{24}$N$_2$O$_4$S requires: C, 67.8; H, 5.3; N, 6.1%.

The starting material A was obtained as follows:

Sodium hydride (50% dispersion in oil; 105 mg) was added to a solution of 5,7-diethyl-3-phenylsulphinyl-1,6-naphthyridin-2(1H)-one (650 mg) in DMF (20 ml) and the mixture was stirred until effervescence ceased. Methyl 4-bromomethylbenzoate (460 mg) was added and the mixture was stirred for 4 hours. Volatile material was removed by evaporation and the residue was partitioned between ethyl acetate and water. The organic phase was separated and dried (MgSO$_4$). The solvent was removed by evaporation to give a residue which was recrystallised from ethyl acetate/petroleum ether to give methyl 4-[(5,7-diethyl-2-oxo-3-phenylsulphinyl-1,2-dihydro-1,6-naphthyridin-1-yl)methyl]benzoate (A) as a white solid (695 mg), m.p. 175°-176° C.; NMR (d$_6$-DMSO): 1.14(t, 3H), 1.33(t, 3H), 2.72(q, 2H), 3.20(q, 2H), 3.82(s, 3H), 5.45(d, 1H), 5.55(d, 1H), 7.15(s, 1H), 7.23(d, 2H), 7.55(m, 3H), 7.83(m, 4H), 8.58(s, 1H); mass spectrum (CI, ammonia): 475 (M+H)$^+$; microanalysis, found: C, 67.8; H, 5.5; N, 6.0%; C$_{27}$H$_{26}$N$_2$O$_4$S requires: C, 68.3; H, 5.5; N, 5.9%.

EXAMPLE 20

Using an analogous procedure to that described in Example 19, but starting from methyl 4-[(5,7-diethyl-2-oxo-3-phenylthio-1,2-dihydro-1,6-naphthyridin-1-yl)methyl]benzoate (A) there was thus obtained 4-[(5,7-diethyl-2-oxo-3-phenylthio-1,2-dihydro-1,6-naphthyridin-1-yl)methyl]benzoic acid as a solid, in 52% yield; m.p. 195°-196° C.; NMR (d$_6$-DMSO): 1.05(t, 3H), 1.15(t, 3H), 2.7(dq, 4H), 5.62(s, 2H), 7.15(s, 1H), 7.35(s, 1H), 7.36(d, 2H), 7.5-7.7(complex m, 5H), 7.90(d, 2H), 12.83(broad, 1H); mass spectrum (CI): 445 (M+H)$^+$; microanalysis, found: C, 69.1; H, 5.5; N, 5.9%; C$_{26}$H$_{24}$N$_2$O$_3$S.0.5H$_2$O requires: C, 68.8; H, 5.5; N, 6.2%.

The starting material A was obtained as follows:

(i) A mixture of 4-amino-2,6-diethylpyridine-3-carbaldehyde (1.8 g), ethyl phenylthioacetate (3.2 ml), piperidine (2 ml) and ethanol (2 ml) was heated at reflux for 72 hours. Volatile material was removed by evaporation and the residue was purified by flash chromatography, eluting with ethyl acetate/petroleum ether (3:7 v/v), to give 5,7-diethyl-3-phenylthio-1,6-naphthyridin-2(1H)-one (1.27 g), m.p. 199°-202° C. (after recrystallisation from ethyl acetate); NMR (d$_6$-DMSO): 1.05(t, 3H), 1.22(t, 3H), 2.7(dq, 4H), 6.92(s, 1H), 7.30(s, 1H), 7.55(m, 5H); mass spectrum (CI, ammonia): 311 (M+H)$^+$; microanalysis, found: C, 69.4; H, 5.9; N, 8.9%; C$_{18}$H$_{18}$N$_2$OS requires: C, 69.6; H, 5.8; N, 9.0%.

(ii) Using a similar procedure to that described in Example 19, part (ii), but starting from 5,7-diethyl-3-phenylthio-1,6-naphthyridin-2(1H)-one, there was thus obtained methyl 4-[(5,7-diethyl-2-oxo-3-phenylthio-1,2-dihydro-1,6-naphthyridin-1-yl)methyl]benzoate (A) as a solid, in 66% yield, m.p. 126°-130° C.; NMR (d6-DMSO): 1.05(t, 3H), 1.12(t, 3H), 2.69(dq, 4H), 3.83(s, 3H), 5.62(s, 2H), 7.08(s, 1H), 7.35(s, 1H), 7.36(d, 2H), 7.5-7.65(complex m, 5H), 7.92(d, 2H); mass spectrum (CI, ammonia): 459 (M+H)+; microanalysis, found: C, 59.6; H, 4.9; N, 5.4%; $C_{27}H_{26}N_2O_3S.1.4SiO_2$ requires: C, 59.8; H, 4.8N, 5.2%.

EXAMPLE 21

Using an analogous procedure to that described in Example 10, but starting from 5,7-diethyl-3-methyl-1-[(2'-(2-triphenylmethyl-2H-tetrazol-5-yl)biphenyl-4-yl)methyl]-1,6-naphthyridin-2(1H)-one there was thus obtained 5,7-diethyl-3-methyl-1-[(2'-(1H-tetrazol-5-yl)biphenyl-4-yl)methyl-1,6-naphthyridin-2(1H)-one hydrochloride, as a solid, in 83% yield, m.p. >250° C.; NMR (d6-DMSO): 1.25(t, 3H), 1.32(t, 3H), 2.27(s, 3H), 2.99(q, 2H), 3.35(q, 2H), 5.59(s, 2H), 7.06(d, 2H), 7.20(d, 2H), 7.45-7.75(m, 5H), 8.30(s, 1H); mass spectrum (+ve FAB, methanol/NBA): 451 (M+H)+; microanalysis, found: C, 66.0; H, 5.5; N, 16.7%; $C_{27}H_{26}N_6O.HCl.0.25H_2O$ requires: C, 66.0; H, 5.6; N, 17.1%.

The starting material A was obtained as follows:

(i) A mixture of 4-amino-2,6-diethylpyridine-3-carbaldehyde (2.0 g), piperidine (0.5 ml) and diethyl methylmalonate (3.0 ml) was heated together at 120° C. for 24 hours. The mixture was then purified by flash chromatography, eluting with ether, to give 5,7-diethyl-3-methyl-1,6-naphthyridin-2(1H)-one as a solid (0.265 g); m.p. 163°-166° C. dec. (after recrystallisation from acetone); NMR (d6-DMSO): 1.22(t, 3H), 1.24(t, 3H), 2.11(s, 3H), 2.71(q, 2H), 2.99(q, 2H), 6.88(s, 1H), 7.96(s, 1H), 11.84(broad, 1H); mass spectrum (CI, ammonia): 217 (M+H)+; microanalysis, found: C, 72.3; H, 7.4; N, 13.1%; $C_{13}H_{16}N_2O$ requires: C, 72.2; H, 7.5; N, 13.0%.

(ii) Using an analogous procedure to that described in Example 10, part (ii), but starting from 5,7-diethyl-3-methyl-1,6-naphthyridin-2(1H)-one, there was thus obtained 5,7-diethyl-3-methyl-1-[(2'-(2-triphenylmethyl-2H-tetrazol-5-yl)biphenyl-4-yl)methyl]-1,6-naphthyridin-2(1H)-one as a foam, in 56% yield, m.p. 65°-79° C.; NMR (d6-DMSO): 1.08(t, 3H), 1.25(t, 3H), 2.24(s, 3H), 2.57(q, 2H), 3.07(q, 2H), 5.47(s, 2H), 6.8-7.8(complex m, 24H), 8.12(s, 1H); mass spectrum (+ve FAB, methanol/NBA): 693 (M+H)+; microanalysis, found: C, 77.1; H, 5.5; N, 11.5%; $C_{46}H_{40}N_6O.H_2O$ requires: C, 77.6; H, 5.9; N, 11.8%.

EXAMPLE 22

Using an analogous procedure to that described in Example 10, but starting from 5,7-diethyl-3-phenyl-1-[(2'-(2-triphenylmethyl-2H-tetrazol-5-yl)biphenyl-4-yl)methyl]-1,6-naphthyridin-2(1H)-one there was thus obtained 5,7-diethyl-3-phenyl-1-[(2'-(1H-tetrazol-5-yl)biphenyl-4-yl)methyl-1,6-naphthyridin-2(1H)-one hydrochloride as a solid, in 58% yield; m.p. 187°-189° C. (dec); NMR (d6-DMSO): 1.28(t, 3H), 1.35(t, 3H), 3.03(q, 2H), 3.48(q, 2H), 5.65(s, 2H), 7.09(d, 2H), 7.28(d, 2H), 7.4-7.7(complex m, 9H), 7.79(dd, 2H), 8.37(s, 1H); mass spectrum (+ve FAB, methanol/NBA): 573 (M+H)+; microanalysis, found: C, 68.4; H, 5.5; N, 14.9%; $C_{32}H_{28}N_6O.HCl.0.5H_2O$ requires: C, 68.8; H, 5.4; N, 15.0%.

The starting material A was obtained as follows:

(i) A mixture of 4-amino-2,6-diethylpyridine-3-carbaldehyde (2.2 g), ethanol (26 ml), aqueous sodium hydroxide solution (10% w/v; 2.2 ml) and phenylacetonitrile (3.8 ml) was heated at reflux for 2 hours. Volatile material was removed by evaporation and the residue was partitioned between ethyl acetate and 2M hydrochloric acid. The organic phase was separated and discarded. The aqueous phase was adjusted to pH 6 with solid sodium carbonate and then extracted twice with dichloromethane. The combined extracts were dried (MgSO4) and solvent was removed by evaporation to give 2-amino-5,7-diethyl-3-phenyl-1,6-naphthyridine (B) as a pale yellow solid (3.2 g); m.p. 109.5°-112° C.; NMR (d6-DMSO): 1.27(t, 3H), 1.28(t, 3H), 2.77(q, 2H), 3.09(q, 2H), 6.41(broad, 2H), 7.05(s, 1H), 7.4-7.6(m, 5H), 7.96(s, 1H); mass spectrum (+ve FAB, methanol/NBA): 278 (M+H)+; microanalysis, found: C, 68.1; H, 6.5; N, 13.1%; $C_{18}H_{19}N_3.HCl.0.25H_2O$ requires: C, 68.0; H, 6.5; N, 13.2%.

(ii) A solution of sodium nitrite (3.2 g) in water (64 ml) was added dropwise over 45 minutes to a solution of compound B (2.0 g) in 2M hydrochloric acid (150 ml). The mixture was stirred for a further 1 hour and then the suspended white solid was collected by filtration and dried under vacuum to give 5,7-diethyl-3-phenyl-1,6-naphthyridin-2(1H)-one (1.0 g); m.p. >260° C.; NMR (d6-DMSO): 1.32(t, 3H), 1.33(t, 3H), 3.07(q, 2H), 3.47(q, 2H), 7.41(s, 1H), 7.43-7.55(m, 3H), 7.74-7.85(m, 2H), 8.31(s, 1H); mass spectrum (+ve FAB, methanol/NBA): 279 (M+H)+; microanalysis, found: C, 76.9; H, 6.6; N, 9.7%; $C_{18}H_{18}N_2O.0.25H_2O$ requires: C, 76.4; H, 6.5; N, 9.9%.

(iii) Using an analogous procedure to that described in Example 10, part (ii), but starting from 5,7-diethyl-3-phenyl-1,6-naphthyridin-2(1H)-one, there was thus obtained 5,7-diethyl-3-phenyl-1-[(2'-(2-triphenylmethyl-2H-tetrazol-5-yl)biphenyl-4-yl)methyl]-1,6-naphthyridin-2(1H)-one (A) as a solid, in 41% yield, m.p. 107°-112° C. (dec); NMR (d6-DMSO): 1.10(t, 3H), 1.28(t, 3H), 2.60(q, 2H), 3.16(q, 2H), 5.54(s, 2H), 6.8-7.85(complex m, 29H), 8.25(s, 1H); mass spectrum (+ve FAB, methanol/NBA): 755 (M+H)+; microanalysis, found: C, 80.8; H, 5.9; N, 10.8%; $C_{51}H_{42}N_6O$ requires: C, 81.1; H, 5.6; N, 11.1%.

EXAMPLE 23

Phthalic anhydride (74 mg) was added to a solution of 1-(4-aminobenzyl)-5,7-diethyl-1,6-naphthyridin-2(1H)-one (A) (153 mg) in THF (10 ml) and the mixture was stirred for 30 minutes. The suspended solid was then collected by filtration and recrystallised from aqueous dimethylacetamide to give 2-[4-(5,7-diethyl-2-oxo-1,2-dihydro-1,6-naphthyridin-1-ylmethyl)phenyl-carbamoyl]benzoic acid (90 mg), m.p. 237°-240° C.; NMR (d6-DMSO): 1.19(t, 3H), 1.25(t, 3H), 2.72(q, 2H), 3.06(q, 2H), 5.43(s, 2H), 6.70(d, 1H), 7.12(s, 1H), 7.20(d, 2H), 7.45-7.65(m, 5H), 7.85(d, 1H), 8.18(d, 1H); mass spectrum (+ve FAB, DMSO/NBA): 456 (M+H)+; microanalysis, found: C, 69.5; H, 5.5; N, 9.5%; $C_{27}H_{25}N_3O_4.0.5H_2O$ requires: C, 69.8; H, 5.6; N, 9.1%.

The starting material A was obtained as follows:

(i) Sodium hydride (50% dispersion in oil; 0.2 g) was added to a stirred suspension of 5,7-diethyl-1,6-naphthyridin-2(1H)-one (1.0 g) in DMF (10 ml) under an atmosphere of argon. The mixture was stirred until effervescence ceased and 4-nitrobenzyl bromide (1.1 g) was added. The mixture was then stirred for 16 hours. The mixture was then poured into water (50 ml) and extracted twice with ethyl acetate. The combined extracts were washed with saturated sodium chloride solution, dried (MgSO4) and solvent was removed by evaporation to give an oil. The oil was purified by flash chromatography, eluting with ethyl acetate/dichloromethane (1:4 v/v) to give 5,7-diethyl-1-(4-nitrobenzyl)-1,6-naphthyridin-2(1H)-one (B) as a solid (1.03 g); m.p. 105°–106° C.; NMR (CDCl$_3$): 1.22(t, 3H), 1.36(t, 3H), 2.77(q, 2H), 3.11(q, 2H), 5.57(s, 2H), 6.69(s, 1H), 6.77(d, 1H), 7.38(d, 2H), 8.03(d, 1H), 8.19(d, 2H); mass spectrum (CI, ammonia): 338 (M+H)$^+$; microanalysis, found: C, 67.0; H, 5.7; N, 12.4%; C$_{19}$H$_{19}$N$_3$O$_3$ requires: C, 67.6; H, 5.7; N, 12.5%.

(ii) A solution of compound B (1.0 g) in THF (50 ml) was stirred with platinum oxide (0.1 g) under a hydrogen atmosphere until the uptake of hydrogen ceased. The catalyst was removed by filtration and the solvent was removed by evaporation to give 1-(4-aminobenzyl)-5,7-diethyl-1,6-naphthyridin-2(1H)-one (A) as a solid, in % yield; m.p. 162°–165° C.; NMR (CDCl$_3$): 1.25(t, 3H), 1.34(t, 3H), 2.81(q, 2H), 3.09(q, 2H), 3.65(broad, 2H), 5.36(s, 2H), 6.62(d, 2H), 6.73(d, 1H), 6.95(s, 1H), 7.06(d, 2H), 7.95(d, 1H); mass spectrum (CI, ammonia): 308 (M+H)$^+$; microanalysis, found: C, 74.0; H, 6.8; N, 13.3; C$_{19}$H$_{21}$N$_3$O requires: C, 74.2; H, 6.9; N, 13.7%.

EXAMPLE 24

Triethylamine (0.7 ml) was added to a solution of 1-(4-aminobenzyl)-5,7-diethyl-1,6-naphthyridin-2(1H)-one (0.62 g) in dichloromethane (100 ml) and the stirred mixture was cooled to −78° C. Trifluoromethanesulphonic anhydride (0.34 ml) was then added dropwise and the mixture was stirred for 3 hours. Volatile material was removed by evaporation and the residue was purified by flash chromatography, eluting with ethyl acetate, to give 5,7-diethyl-1-(4-trifluoromethylsulfonamido)benzyl-1,6-naphthyridin-2(1H)-one (0.45 g) as a solid, m.p. 209°–211° C. (after trituration with ether and recrystallisation from ethyl acetate/petroleum ether); NMR (d$_6$-DMSO): 1.15(t, 3H), 1.25(t, 3H), 2.72(q, 2H), 3.07(q, 2H), 5.46(s, 2H), 6.72(d, 1H), 7.12(s, 1H), 7.16(d, 2H), 7.22(d, 2H), 8.22(d, 1H); mass spectrum (+ve FAB, methanol/NBA): 440 (M+H)$^+$; microanalysis, found: C, 54.8; H, 4.7; N, 9.2%; C$_{20}$H$_{20}$F$_3$N$_3$O$_3$S requires: C, 54.7; H, 4.6; N, 9.6%.

EXAMPLE 25

Using an analogous procedure to that described in Example 23, but employing 3,6-dichlorophthalic anhydride in place of phthalic anhydride, there was thus obtained 3,6-dichloro-2-[4-(5,7-diethyl-2-oxo-1,2-dihydro-1,6-naphthyridin-1-ylmethyl)phenylcarbamoyl]benzoic acid, as a solid, in 24% yield; m.p. 172°–174° C. (after recrystallisation from methanol); NMR (d$_6$-DMSO): 1.19(t, 3H), 1.24(t, 3H), 2.73(q, 2H), 3.06(q, 2H), 5.45(s, 2H), 6.70(d, 1H), 7.13(s, 1H), 7.23(d, 2H), 7.57(d, 2H), 7.64(s, 2H), 8.20(d, 1H); mass spectrum (+ve FAB, methanol/NBA): 524 (M+H)$^+$; microanalysis, found: C, 60.6; H, 4.5; N, 8.5%; C$_{27}$H$_{23}$Cl$_2$N$_3$O$_3$.0.5H$_2$O: C, 60.7; H, 4.5; N, 7.9%.

EXAMPLE 26

Potassium hydroxide (0.112 g) was added to a solution of methyl 4-[(5,7-diethyl-2-oxo-1,2-dihydro-1,6-naphthyridin-1-yl)-methyl]benzoate (A) (0.35 g) in ethanol (10 ml) and the mixture was heated at reflux for 90 minutes. Volatile material was removed by evaporation and the residue was dissolved in a minimum of water which was then acidified with acetic acid. Ether was added to the mixture and the solid which crystallised was collected by filtration. Further solid was obtained by adding petroleum ether to the ether phase of the filtrate. The combined solids were recrystallised from ethyl acetate/petroleum ether to give 4-[(5,7-diethyl-2-oxo-1,2-dihydro-1,6-naphthyridin-1-yl)methyl]benzoic acid (0.175 g), as a solid, m.p. 143°–146° C.; NMR (CDCl$_3$): 1.21(t, 3H), 1.35(t, 3H), 2.79(q, 2H), 3.12(q, 2H), 5.56(s, 2H), 6.77(s, 1H), 6.80(d, 1H), 7.30(d, 2H), 7.81(d, 1H), 8.05(d, 2H); mass spectrum (CI. ammonia): 337 (M+H)$^+$; microanalysis, found: C, 71.3; H, 6.3; N, 7.9%; C$_{20}$H$_{20}$N$_2$O$_3$ requires: C, 71.4; H, 6.0; N, 8.3%.

The starting material A was obtained as follows:

Sodium hydride (50% dispersion in oil; 1.05 g) was added to a stirred solution of 5,7-diethyl-1,6-naphthyridin-2(1H)-one (4.0 g) in DMF (75 ml) and the mixture was stirred until effervesence ceased. Methyl 4-bromomethylbenzoate (4.58 g) was added and the mixture was stirred under argon for 4 hours. The mixture was then poured into water and extracted twice with ethyl acetate. The combined organic extracts were washed with saturated sodium chloride solution, dried (MgSO$_4$) and solvent was removed by evaporation. The resultant solid was purified by flash chromatography, eluting with ethyl acetate/petroleum ether (3:1 v/v gradually increasing to 1:0 v/v) to give methyl 4-[(5,7-diethyl-2-oxo-1,2-dihydro-1,6-naphthyridin-1-yl)methyl]benzoate as a solid (5.0 g); m.p. 128°–130° C.; NMR (d$_6$-DMSO): 1.15(t, 3H), 1.25(t, 3H), 2.69(q, 2H), 3.06(q, 2H), 3.83(s, 3H), 5.56(s, 2H), 6.71(d, 1H), 7.04(s, 1H), 7.35(d, 2H), 7.91(d, 2H), 8.22(d, 1H); mass spectrum (+ve FAB, methanol/DMSO/NBA): 351 (M+H)$^+$; microanalysis, found: C, 71.8; H, 6.3; N, 8.2%; C$_{21}$H$_{22}$N$_2$O$_3$ requires: C, 72.0; H, 6.3; N, 8.0%.

EXAMPLE 27

1-(3-Dimethylaminopropyl-3-ethylcarbodiimide hydrochloride (0.19 g), benzenesulphonamide (0.157 g) and 4-dimethylaminopyridine (0.122 g) were added to a solution of 4-[(5,7-diethyl-2-oxo-1,2-dihydro-1,6-naphthyridin-1-yl)methyl]benzoic acid (0.336 g) in dichloromethane (25 ml) and the mixture was stirred for 16 hours. The reaction mixture was then paritioned between water and dichloromethane. The organic phase was separated and washed with saturated sodium chloride solution and dried (MgSO$_4$). The solvent was removed by evaporation to give a gum which was purified by flash chromatography, eluting with methanol/dichloromethane (1:19 v/v, gradually increasing to 1:9 v/v), to give 5,7-diethyl-1-(4-phenylsulfonamidocarbonyl)benzyl-1,6-naphthyridin-2(1H)-one as a solid (0.14 g), m.p. 190°–200° C.; NMR (CDCl$_3$+d$_6$-DMSO): 1.18(t, 3H), 1.34(t, 3H), 2.72(q, 2H), 3.08(q, 2H), 5.49(s, 2H), 6.74(d, 1H), 6.75(s, 1H), 7.18(d, 2H), 7.35–7.55(m, 3H), 7.95–8.10(m, 5H); mass spectrum (+ve FAB, methanol/NBA): 476 (M+H)$^+$; microanalysis, found: C, 62.1; H, 5.0; N, 8.3%; C$_{26}$H$_{25}$N$_3$O$_4$S.1.5H$_2$O requires: C, 62.2; H, 5.6; N, 8.4%.

EXAMPLE 28

Using an analogous procedure to that described in Example 28, but using methanesulphonamide (0.12 g) in place of benzenesulphonamide and 0.23 g of the carbodiimide hydrochloride, there was thus obtained 5,7-diethyl-1-(4-methylsulfonamidocarbonyl)benzyl-1,6-naphthyridin-2(1H)-one as a solid (0.06 g), m.p. 225°–255° C.; NMR (d$_6$-DMSO): 1.14(t, 3H), 1.24(t, 3H), 2.68(q, 2H), 2.82(s, 3H), 3.06(q, 2H), 5.50(s, 2H), 6.70(d, 1H), 7.05(s, 1H), 7.17(d, 2H), 7.86(d, 2H), 8.22(d, 1H); mass spectrum (+ve FAB, methanol/glycerol):

414 (M+H)+; microanalysis, found: C, 54.3; H, 5.8; N, 8.5%; $C_{21}H_{23}N_3O_4S \cdot H_2O$ requires: C, 54.0; H, 6.2; N, 9.0%.

EXAMPLE 29

Using an analogous procedure to that described in Example 27, but using 2-toluenesulfonamide in place of benzenesulphonamide, there was thus obtained 5,7-diethyl-1-(4-(2-tolyl)sulphonamidocarbonyl)benzyl-1,6-naphthyridin-2(1H)-one as a solid, in 29% yield; m.p. 243°-246° C. (after recrystallisation from ethanol/ether); NMR ($d_6$-DMSO): 1.13(t, 3H), 1.24(t, 3H), 2.68(q, 2H), 3.05(q, 2H), 5.48(s, 2H), 6.69(d, 1H), 7.03(s, 1H), 7.1-7.35(complex m, 5H), 7.75-7.9(m, 3H), 8.20(d, 1H); mass spectrum (+ve FAB, methanol/NBA): 490 (M+H)+; microanalysis, found: C, 62.7; H, 5.1; N, 8.1%; $C_{27}H_{27}N_3O_4S \cdot 0.5SiO_2$ requires: C, 62.4; H, 5.2; N, 8.1%.

EXAMPLE 30

Using an analogous procedure to that described in Example 2, but starting from 5,7-diethyl-4-phenylthio-1-[(2'-(2-triphenylmethyl-2H-tetrazol-5-yl)biphenyl-4-yl)methyl]-1,6-naphthyridin-2(1H)-one (A), there was thus obtained 5,7-diethyl-4-phenylthio-1-[(2'-(1H-tetrazol-5-yl)biphenyl-4-yl)methyl]-1,6-naphthyridin-2(1H)-one as a solid, in 76% yield; m.p. 195°-198° C. (dec) (after reprecipitation from ethanol solution by addition of ether); NMR($d_6$-DMSO): 1.21(t, 3H), 1.49(t, 3H), 2.94(q, 2H), 3.67(q, 2H), 5.49(s, 2H), 5.89(s, 1H), 7.05(d, 2H), 7.17(d, 2H), 7.4-7.8(complex m, 10H); mass spectrum (+ve FAB, DMSO/NBA): 545(M+H)+; microanalysis, found: C, 66.2; H, 4.9; N, 14.5%; $C_{32}H_{28}N_6OS$ requires: C, 66.1; H, 5.0; N, 14.5%.

The starting material A was obtained as follows:

Sodium hydride (50% dispersion in oil; 100 mg) was added to a stirred solution of thiophenol (0.2 ml) in dimethylacetamide (10 ml) and the mixture was stirred until effervescence ceased. 4-Chloro-5,7-diethyl-1-[(2'-(2-triphenylmethyl-2H-tetrazol-5-yl)biphenyl-4-yl)methyl]-1,6-naphthyridin-2(1H)-one (0.7 g) was added to the solution and the mixture was stirred at 50° C. for 4 hours. The reaction mixture was then poured into water and extracted twice with ethyl acetate. The combined extracts were washed with water, saturated sodium chloride solution and dried (MgSO4). Solvent was removed by evaporation to leave an oil which was purified by flash chromatography, eluting with ethyl acetate/petroleum ether (3:1 v/v, increasing to 2:5 v/v) to give 5,7-diethyl-4-phenylthio-1-[(2'-(2-triphenylmethyl-2H-tetrazol-5-yl)biphenyl-4yl)methyl[-1,6-naphthyridin-2(1H)-one (A) as a solid (0.53 g); m.p. 166°-168° C. (after recrystallisation from acetonitrile); NMR ($d_6$-DMSO): 1.07(t, 3H), 1.40(t, 3H), 2.58(q, 2H), 3.47(q, 2H), 5.40(s, 2H), 5.80(s, 1H), 6.8-7.8(complex m, 29H); mass spectrum (+ve FAB): 787 (M+H)+; microanalysis, found: C, 78.1; H, 5.1; N, 10.9%; $C_{51}H_{42}N_6OS$ requires: C, 77.8; H, 5.4; N, 10.7%.

EXAMPLE 31

Using an analogous procedure to that described in Example 10, but starting from 5,7-diethyl-4-methyl-1-[(2'-(2-triphenylmethyl-2H-tetrazol-5-yl)biphenyl-4-yl)methyl]-1,6-naphthyridin-2(1H)-one (A) there was thus obtained 5,7-diethyl-4-methyl-1-[(2'-(1H-tetrazol-5-yl)-biphenyl-4-yl)methyl]-1,6-naphthyridin-2(1H)-one hydrochloride as a solid, in 92% yield; m.p. 261°-263° C.; NMR ($d_6$-DMSO): 1.21(t, 3H), 1.34(t, 3H), 2.72(s, 3H), 2.97(q, 2H), 3.43(q, 2H), 5.57(s, 2H), 6.88(s, 1H), 7.06(d, 2H), 7.19(d, 2H), 7.45-7.7(complex m, 5H); mass spectrum (+ve FAB, methanol/NBA): 451 (M+H)+; microanalysis, found: C, 64.3; H, 5.7; N, 16.7%; $C_{27}H_{26}N_6O \cdot HCl \cdot H_2O$ requires: C, 64.1; H, 5.5; N, 16.6%.

The starting material A was obtained as follows:

(i) A solution of 4-amino-2,6-diethylpyridine-3-carbaldehyde (1.78 g) in ether (50 ml) was added dropwise to a stirred and refluxing solution of methylmagnesium iodide in ether [obtained from magnesium (1.78 g) and methyl iodide (3.8 ml) in ether (10 ml)]. After the addition was complete, the mixture was stirred and heated at reflux for a further 1 hour. The mixture was cooled in an ice bath and concentrated aqueous ammonia solution (20 ml) was added cautiously, followed by water (100 ml). The mixture was extracted twice with ethyl acetate and the combined extracts were washed with water, saturated sodium chloride solution and dried (MgSO4). Volatile material was removed by evaporation to leave a solid which was recrystallised from ethyl acetate/petroleum ether to give 4-amino-2,6-diethyl-3-(2-hydroxyethyl)pyridine (B) (0.72 g), m.p. 153°-156° C.; NMR ($d_6$-DMSO): 1.12(t, 6H), 1.36(d, 3H), 2.44(q, 2H), 2.55(dq, 2H), 5.08(dq, 1H), 5.42(d, 1H), 5.80(s, 2H), 6.25(s, 1H); mass spectrum (CI, ammonia): 195 (M+H)+; microanalysis, found: C, 68.0; H, 9.2; N, 14.4%; $C_{11}H_{18}N_2O$ requires: C, 68.0; H, 9.3; N, 14.4%.

(ii) Activated manganese dioxide (1.0 g) was added to a stirred solution of compound B (0.5 g) in toluene (150 ml) and the mixture was heated at reflux for 16 hours. The mixture was filtered and the filtrate was concentrated by evaporation. The residue was purified by flash chromatography, eluting with methanol/dichloromethane (1:9 v/v) to give 3-acetyl-4-amino-2,6-diethylpyridine (C) (0.24 g) as a solid, m.p. 104°-106° C.; NMR ($d_6$-DMSO): 1.13(t, 3H), 1.15(t, 3H), 2.44(s, 3H), 2.51(dq, 4H), 6.08(s, 2H), 6.33(s, 1H); mass spectrum (CI, ammonia): 193 (M+H)+; microanalysis, found: C, 67.8; H, 8.3; N, 14.6%; $C_{11}H_{16}N_2O \cdot 0.125 H_2O$ requires: C, 67.9; H, 8.4; N, 14.4%.

(iii) A mixture of compound C (1.1 g) and (carbethoxymethylene)triphenylphosphorane (6 g) in xylene (200 ml) was stirred and heated at reflux for 4 hours. The solution was then concentrated by evaporation and a solution of sodium (2.6 g) in methanol (200 ml) was added. The mixture was stirred and heated at reflux for 4 hours. Volatile material was removed by evaporation and water was added to the residue. The mixture was then acidified by the addition of concentrated hydrochloric acid and extracted twice with ether. The ether extracts were discarded. The aqueous phase was basified with solid potassium carbonate and extracted twice with ethyl acetate. The combined extracts were washed with water, saturated sodium chloride solution and dried (MgSO4). Solvent was removed by evaporation to leave a residue which was recrystallised from acetone to give 5,7-diethyl-4-methyl-1,6-naphthyridin-2(1H)-one (D) (0.31 g) as a solid, m.p. 220°-223° C.; NMR ($d_6$-DMSO): 1.22(t, 3H), 1.24(t, 3H), 2.62(s, 3H), 2.69(q, 2H), 3.16(q, 2H), 6.33(s, 1H), 6.91(s, 1H), 11.68(s, 1H); mass spectrum (CI, ammonia): 217 (M+H)+; microanalysis, found: C, 71.5; H, 7.1; N, 12.9%; $C_{13}H_{16}N_2O$ requires: C, 72.2; H, 7.5; N, 13.0%.

(iv) Compound B was alkylated using an analogous procedure to that described in Example 10, part (ii). The product was purified by flash chromatography, eluting with ethyl acetate/petroleum ether (2:5 v/v, increasing to 1:1 v/v), to give 5,7-diethyl-4-methyl-1-[(2'-(2-triphenylmethyl-2H-tetrazol-5-yl)biphenyl-4-yl)methyl]-1,6-naphthyridin-2(1H)-one (A) as a solid, in 46% yield; m.p. 156°–158° C.; NMR (d$_6$-DMSO): 1.06(t, 3H), 1.25(t, 3H), 2.53(q, 2H), 2.71(s, 3H), 3.22(q, 2H), 5.47(s, 2H), 6.65(s, 1H), 6.8–7.8(complex m, 24H); mass spectrum (+ve FAB, methanol/NBA): 693(M+H)$^+$; microanalysis, found: C, 79.9; H, 6.0; N, 12.1%; C$_{46}$H$_{40}$N$_6$O requires: C, 79.7; H, 5.8; N, 12.1%.

EXAMPLE 32

Using an analogous procedure to that described in Example 2, but starting from 5,7-diethyl-3,4-dimethyl-1-[(2'-(2-triphenylmethyl-2H-tetrazol-5-yl)biphenyl-4-yl)methyl]-1,6-naphthyridin-2(1H)-one (A), there was thus obtained 5,7-diethyl-3,4-dimethyl-1-[(2'-(1H-tetrazol-5-yl)biphenyl-4-yl)methyl]-1,6-naphthyridin-2(1H)-one hydrochloride as a solid, in 88% yield; m.p. 283°–285° C.; NMR (d$_6$-DMSO): 1.21(t, 3H), 1.38(t, 3H), 2.27(s, 3H), 2.97(q, 2H), 3.45(q, partly hidden by water peak), 5.61(s, 2H), 7.06(d, 2H), 7.18(d, 2H), 7.45–7.75(complex m, 5H); mass spectrum (+ve FAB, methanol/NBA): 465 (M+H)$^+$; microanalysis, found: C, 66.4; H, 5.9; N, 16.6%; C$_{28}$H$_{28}$N$_6$O.HCl0.25H$_2$O requires: C, 66.5; H, 5.5; N, 16.6%.

The starting material A was obtained as follows:

(i) Using an analogous procedure to that described in Example 31, part (iii), but starting from (carbethoxyethylidene)triphenylphosphorane in place of (carbethoxymethylene)triphenylphosphorane, there was thus obtained 5,7-diethyl-3,4-dimethyl-1,6-naphthyridin-2(1H)-one (B) as a solid, in 29% yield; m.p. 213°–215° C; NMR (d$_6$-DMSO): 1.21(t, 3H), 1.25(t, 3H), 2.09(s, 3H), 2.54(s, 3H), 2.68(q, 2H), 3.15(q, 2H), 6.88(s, 1H), 11.70(s, 1H); mass spectrum (+ve FAB, methanol/NBA): 231 (M+H)$^+$; microanalysis, found: C, 72.4; H, 7.9; N, 12.0%; C$_{14}$H$_{18}$N$_2$O.0.125H$_2$O requires: C, 72.2; H, 7.7; N, 12.0%.

(ii) Compound B was alkylated using an analogous procedure to that described in Example 10, part (ii). The product was purified by flash chromatography, eluting with ethyl acetate/petroleum ether (2:3 v/v), to give 5,7-diethyl-3,4-dimethyl-1-[(2'-(2-triphenylmethyl-2H-tetrazol-5-yl)biphenyl-4-yl)methyl]-1,6-naphthyridin-2(1H)-one as a solid, in 47% yield; m.p. 159°–160° C.; NMR (d$_6$-DMSO): 1.06(t, 3H), 1.28(t, 3H), 2.24(s, 3H), 2.52(q, 2H), 2.61(s, 3H), 3.15(q, 2H), 5.48(s, 2H), 6.8–7.8(complex m, 24H); mass spectrum (+ve FAB, methanol/NBA): 707 (M+H)$^+$; microanalysis, found: C, 78.8; H, 6.3; N, 11.4%; C$_{47}$H$_{42}$N$_6$O.0.5H$_2$O requires: C, 78.8; H, 6.0; N, 11.7%.

EXAMPLE 33

A solution of 1-(4-aminobenzyl)-5,7-diethyl-1,6-naphthyridin-2(1H)-one (0.309 g) in THF (10 ml) was added dropwise to a solution of 2-sulphobenzoic acid cyclic anhydride (0.184 g) in THF (10 ml). The mixture was stirred for 3 hours and the suspended solid was collected by filtration. The solid was recrystallised from aqueous DMF to give 2-[4-(5,7-diethyl-2-oxo-1,2-dihydro-1,6-naphthyridin-1-ylmethyl)phenylcarbamoyl]benzenesulphonic acid as a solid, in 52% yield; m.p. 233°–236° C.; NMR (d$_6$-DMSO): 1.27(t, 3H), 1.29(t, 3H), 2.93(q, 2H), 3.23(q, partly hidden by water peak), 5.55(s, 2H), 6.98(d, 1H), 7.29(d, 2H), 7.48(m, 2H), 7.60(d, 2H), 7.62(s, 1H), 7.70(m, 1H), 7.86(m, 1H), 8.37(d, 1H), 11.31(s, 1H); mass spectrum (+ve FAB, methanol/NBA): 492 (M+H)$^+$; microanalysis, found: C, 62.3; H, 5.2; N, 8.5%; C$_{26}$H$_{25}$N$_3$O$_5$S.0.5H$_2$O requires: C, 62.3; H, 5.2; N, 8.4%.

EXAMPLE 34

Using an analogous procedure to that described in Example 10, but starting from 5,7-diethyl-3-methoxy-1-[(2'-(2-triphenylmethyl-2H-tetrazol-5-yl)biphenyl-4-yl)methyl]-1,6-naphthyridin-2(1H)-one (A), there was thus obtained 5,7-diethyl-3-methoxy-1-[(2'-(1H-tetrazol-5-yl)biphenyl-4-yl)methyl]-1,6-naphthyridin-2(1H)-one, as a solid, in 94% yield (after purification by reprecipitation from methanol solution by addition of ether); NMR (d$_6$-DMSO): 1.24(t, 3H), 1.33(t, 3H), 2.98(q, 2H), 3.39(q, 2H), 3.99(s, 3H), 5.60(s, 2H), 7.06(d, 2H), 7.20(d, 2H), 7.40(s, 1H), 7.45–7.7(m, 5H); mass spectrum (+ve FAB, methanol/NBA): 467 (M+H)$^+$; microanalysis, found: C, 63.1; H, 5.4; N, 15.9%; C$_{27}$H$_{26}$N$_6$O$_2$.0.75H$_2$O requires: C, 62.7; H, 5.5; N, 16.3%.

The starting material A was obtained as follows:

(i) A mixture of 4-amino-2,6-diethylpyridine-3-carbaldehyde (0.75 g), methoxyacetonitrile (3 ml) and sodium methoxide (0.45 g) was heated at reflux for 90 minutes. The mixture was allowed to cool, dissolved in methanol/dichloromethane (1:1 v/v; 8 ml) and purified by flash chromatography, eluting with ethyl acetate, to give 2-amino-5,7-diethyl-3-methoxy-1,6-naphthyridine (B) as a solid (0.12 g), m.p. 223°–227° C.; NMR (d$_6$-DMSO): 1.25(t, 3H), 1.29(t, 3H), 2.75(q, 2H), 3.09(q, 2H), 3.95(s, 3H), 6.89(broad s, 1H), 7.01(s, 1H), 7.38(s, 1H); mass spectrum (CI, ammonia): 232 (M+H)$^+$; microanalysis, found: C, 66.5; H, 7.4; N, 17.8%; C$_{13}$H$_{17}$N$_3$O.0.25H$_2$O requires: C, 66.2; H, 7.4; N, 17.8%.

(ii) A solution of sodium nitrite (4.5 g) in water (90 ml) was added dropwise over one hour to a stirred solution of compound B (2.8 g) in 2M hydrochloric acid (150 ml). Stirring was continued for a further 30 minutes after the addition was complete. Further sodium nitrite (4.5 g) in water (45 ml) was then added dropwise in three equal portions, each portion being added over 30 minutes with 30 minutes stirring in between additions. The mixture was then stirred for 16 hours. The mixture was then adjusted to pH9 by addition of solid sodium bicarbonate and extracted twice with dichloromethane. The combined extracts were dried (MgSO$_4$) and solvent was removed by evaporation. The residue was recrystallised from ethyl acetate/acetone to give 5,7-diethyl-3-methoxy-1,6-naphthyridin-2(1H)-one (C) as a solid (0.53 g), m.p. 217°–220° C.; NMR (d$_6$-DMSO): 1.22(t, 3H), 1.26(t, 3H), 2.71(q, 2H), 3.01(q, 2H), 3.86(s, 3H), 6.88(s, 1H), 7.18(s, 1H), 12.00(s, 1H); mass spectrum (+ve FAB): 233 (M+H)$^+$; microanalysis, found: C, 66.1; H, 6.9; N, 11.9%; C$_{13}$H$_{16}$N$_2$O$_2$.0.25H$_2$O requires: C, 65.9; H, 6.8; N, 11.8%.

(iii) Compound C was alkylated using an analogous procedure to that described in Example 10, part (ii) to give 5,7-diethyl-3-methoxy-1-[(2'-(2-triphenylmethyl-2H-tetrazol-5-yl)biphenyl-4-yl)methyl]-1,6-naphthyridin-2(1H)-one (A) as a solid, in 52% yield; m.p. 87°–95° C.; NMR (d$_6$-DMSO): 1.08(t, 3H), 1.28(t, 3H), 2.55(q, 2H), 3.08(q, 2H), 3.94(s, 3H), 5.49(s, 2H), 6.8–7.8(complex m, 25H); mass spectrum (+ve FAB): 709 (M+H)$^+$; microanalysis, found: C, 77.1; H, 5.8; N, 11.9%; C$_{46}$H$_{40}$N$_6$O$_2$.0.25H$_2$O requires: C, 77.4; H, 5.7; N, 11.8%.

EXAMPLE 35

5,7-Diethyl-3-methoxy-1-[(2'-(1H-tetrazol-5-yl)biphenyl-4-yl)methyl]-1,6-naphthyridin-2(1H)-one (80 mg) was suspended in dichloromethane (1 ml) and a 1M solution of boron tribromide in dichloromethane (0.5 ml) was added. The mixture was stirred for 16 hours then methanol (3 ml) was added dropwise. The mixture was heated at reflux for 5 minutes and volatile material was then removed by evaporation. The residue was recrystallised from ethanol/ether to give 5,7-diethyl-3-hydroxy-1-[(2'-(1H-tetrazole-5-yl)biphenyl-4-yl)methyl]-1,6-naphthyridin-2(1H)-one hydrobromide as a solid (45 mg), m.p. 190°–194° C.; NMR (d$_6$-DMSO): 1.24(t, 3H), 1.30(t, 3H), 2.92(q, 2H), 3.22(q, 2H), 5.64(s, 2H), 7.07(d, 2H), 7.22(d, 2H), 7.45–7.75(m, 6H); mass spectrum (+ve FAB, methanol/NBA): 453 (M+H)$^+$; microanalysis, found: C, 57.1; H, 4.9; N, 14.7%; $C_{26}H_{24}N_6O_2 \cdot HBr \cdot 1.5H_2O$ requires: C, 56.7; H, 5.1; N, 15.2%.

EXAMPLE 36

Using a analogous procedure to that described in Example 26, but starting from ethyl 2-[4-(5,7-diethyl-2-oxo-1,2-dihydro-1,6-naphthyridin-1-ylmethyl)phenoxymethyl]benzoate (A) there was thus obtained 2-[4-(5,7-diethyl-2-oxo-1,2-dihydro-1,6-napthyridin-1-ylmethyl)phenoxymethyl]benzoic acid as a solid, in 47% yield: m.p. 183°–184° C. (after recrystallisation from ethyl acetate/petroleum ether); NMR (d$_6$-DMSO): 1.17(t, 3H), 1.23(t, 3H), 2.71(q, 2H), 3.04(q, 2H), 5.40(s, 4H), 6.68(d, 1H), 6.91(d, 2H), 7.13(s, 1H), 7.19(d, 2H), 7.35–7.65(m, 3H), 7.90(d, 1H), 8.18(d, 1H); mass spectrum (+ve FAB, methanol/NBA): 443 (M+H)$^+$; microanalysis, found: C, 73.4; H, 6.0; N, 6.3%; $C_{27}H_{26}N_2O_4$ requires: C, 73.3; H, 5.9; N, 6.3%.

The starting material A was obtained as follows:

(i) A mixture of p-hydroxybenzaldehyde (3.05 g), ethyl 2-bromomethylbenzoate (5.4 g) and potassium carbonate (5.52 g) in acetone (100 ml) was stirred and heated at reflux for 4 hours. The mixture was allowed to cool, filtered and the filtrate concentrated by evaporation to give an oil. The oil was dissolved in ethyl acetate and the solution was washed with 2M aqueous sodium hydroxide solution, followed by water and then saturated sodium chloride solution. The organic phase was dried (MgSO$_4$) and concentrated by evaporation to give an oil. The oil was purified by flash chromatography, eluting with ethyl acetate/petroleum ether (1:4 v/v) to give ethyl 2-[(4-formylphenoxy)methyl]benzoate (B) as a solid (5.6 g), m.p. 69°–70° C.; NMR (d$_6$-DMSO): 1.24(t, 3H), 4.26(q,2H), 5.52(s, 2H), 7.17(d, 2H), 7.4–8.0(m, 6H), 9.87(s, 1H); mass spectrum (CI, ammonia): 2.85 (M+H)$^+$.

(ii) Sodium borohydride (0.3 g) was added to a solution of compound B (1.04 g) in ethanol (100 ml) and the mixture was stirred for 16 hours. The solvent was removed by evaporation and water was added to the residue. The mixture was then acidified with concentrated hydrochloric acid and extracted twice with ethyl acetate. The combined extracts were dried (MgSO$_4$) and concentrated by evaporation to give ethyl 2-[(4-hydroxymethyl)phenoxy)methyl]benzoate (C) as an oil (0.5 g); NMR (d$_6$-DMSO): 1.27(t, 3H), 4.27(q, 2H), 4.41(s, 2H), 5.0(broad, 1H), 5.38(s, 2H), 6.92(d, 2H), 7.23(d, 2H), 7.4–7.7(m, 3h), 7.89(d, 1H); mass spectrum (CI, ammonia): 3.04 (M+NH$_4$)$^+$.

(iii) Thionyl chloride (1 ml) and DMF (2 drops) were added to a solution of compound C (0.46 g) in THF (25 ml) and the mixture was stirred for 1 hour. Volatile material was removed by evaporation and toluene was added to the residue. The mixture was again concentrated by evaporation to give ethyl 2-[(4-(chloromethyl)phenoxy)methyl]-benzoate (D) (0.45 g), which was used without further purification or characterisation.

(iv) Using an analogous procedure to that described in Example 26, but using Compound D in place of methyl 4-bromomethylbenzoate, there was thus obtained ethyl 2-[4-(5,7-diethyl-2-oxo-1,2-dihydro-1,6-napthyridin-1-ylmethyl)phenoxymethyl]benzoate (A) as a colourless oil, in 66% yield; NMR (d$_6$-DMSO): 1.16(t, 3H), 1.20(t, 3H), 1.23(t, 3H), 2.71(q, 2H), 3.04(q, 2H), 4.22(q, 2H), 5.34(s, 2H), 5.41(s, 2H), 6.68(d, 1H), 6.91(d, 2H), 7.12(s, 1H), 7.19(d, 2H), 7.4–7.7(m, 3H), 7.87(d, 1H), 8.18(d, 1H); mass spectrum (+ve FAB, methanol/NBA): 471 (M+H)$^+$.

EXAMPLE 37

A mixture of 4-(5,7-diethyl-2-oxo-1,2-dihydro-1,6-naphthyridin-1-ylmethyl)phenylboronic acid (A) (0.6 g), N-tert-butyl-2-iodobenzenesulphonamide (0.7 g), tetrakis(triphenylphosphine)palladium(O) (0.1 g), 2M aqueous sodium carbonate solution (2 ml) and toluene (4 ml) was stirred and heated at reflux for 4 hours. The mixture was then poured into water and extracted twice with ethyl acetate. The combined extracts were washed with water, followed by saturated sodium chloride solution and dried (MgSO$_4$). The solvent was removed by evaporation and the residue was purified by flash chromatography, eluting with ethyl acetate/petroleum ether (3:2 v/v) and increasing to neat ethyl acetate, to give N-tert-4'-[(5,7-diethyl-2-oxo-1,2-dihydro-1,6-napthyridin-1-yl)methyl]-biphenyl-2-sulphonamide as a solid (0.15 g), m.p. 163°–165° C.; NMR (d$_6$-DMSO): 0.93(s, 9H), 1.19(t, 3H), 1.26(t, 3H), 2.72(q, 2H), 3.06(q, 2H), 5.53(s, 2H), 6.35(s, 1H), 6.71(d, 1H), 7.12(s, 1H) 7.22–7.77(m, 7H), 8.02(dd, 1H), 8.21(d, 1H); mass spectrum (+ve FAB, methanol/NBA): 504 (M+H)$^+$; microanalysis, found: C, 67.9; H, 6.5; N, 8.2%; $C_{29}H_{33}N_3O_3S \cdot 0.5H_2O$ requires: C, 68.0; H, 6.6; N, 8.2%

The starting material A as obtained as follows:

Using a analogous procedue to that described in Example 26, but using 4-bromomethylphenylboronic acid (obtained as described in *J. Am. Chem. Soc.*, 1958, 80, 835–838) in place of methyl 4-bromomethylbenzoate, there was thus obtained (without purification by flash chromatography) 4-(5,7-diethyl-2-oxo-1,2-dihydro-1,6-napthyridin-1-ylmethyl)phenylboronic acid (A) as a solid, in 79% yield, which was used without further purification or characterisation.

N-tert-butyl-2-iodobenzenesulphonamide was itself obtained as follows:

2-Iodobenzenesulphonyl chloride (5.0 g) in THF (70 ml) was added dropwise to a stirred solution of tert-butylamine (11.4 ml) in THF (100 ml) and the mixture was heated at reflux for 3 hours. Volatile material was removed by evaporation and the residue was partitioned between water and ethyl acetate. The organic phase was separated and washed successively with 2M aqueous hydrochloric acid, water, 2M aqueous sodium carbonate solution, saturated sodium chloride solution and then dried (MgSO$_4$). The solvent was removed by evaporation to give N-tert-butyl-2-iodobenzenesulphonamide (4.2 g) as a yellow solid, m.p. 149°–150° C. (after recrystallisation from ethyl acetate/petroleum ether); NMR (d₆-DMSO): 1.13(s, 9H), 7.26(dt, 1H), 7.45(s, 1H), 7.57(dt, 1H), 8.07(dd, 1H), 8.11(dd, 1H); mass spectrum (CI, ammonia): 357 (M+NH₄)⁺; microanalysis, found: C, 35.7; H, 4.0; N, 4.0%; C₁₀H₁₄INO₂S requires: C, 35.4; H, 4.2; N, 4.1%.

EXAMPLE 38

A solution of N-tert-butyl-4'-[(5,7-diethyl-2-oxo-1,2-dihydro-1,6-naphthyridin-1-yl)methyl]biphenyl-2-sulphonamide (200 mg) in trifluoroacetic acid (5 ml) was heated at reflux for 3 hours. Volatile material was removed by evaporation and water was added to the residue. The resultant solution was basified by the addition of solid potassium carbonate and then extracted twice with ethyl acetate. The combined extracts were washed with water, saturated sodium chloride solution and then dried (MgSO₄). The solvent was removed by evaporation to give 4'-[(5,7-diethyl-2-oxo-1,2-dihydro-1,6-naphthyridin-1-yl)methyl]biphenyl-2-sulphonamide as a solid (137 mg); m.p. 199°-200° C.; NMR (d₆-DMSO): 1.18(t, 3H), 1.26(t, 3H), 2.73(q, 2H), 3.07(q, 2H), 5.54(s, 2H), 6.72(d, 1H), 7.1-7.7(m, 10H), 8.01(dd, 1H), 8.23(d, 1H); mass spectrum (+ve FAB, methanol/NBA): 448 (M+H)⁺; microanalysis, found: C, 67.0; H, 5.5; N, 9.2%; C₂₅H₂₅N₃O₃S requires: C, 67.1; H, 5.6; N, 9.4%.

EXAMPLE 39

A mixture of 4'-[(5,7-diethyl-2-oxo-1,2-dihydro-1,6-naphthyridin-1-yl)methyl]biphenyl-2-sulphonamide (250 mg), acetyl chloride (2 ml) and acetic acid (1 ml) was heated at reflux for 4 hours. The mixture was then concentrated by evaporation and the residue was purified by repeated precipitation from ethanol solution by the addition of ether to give N-acetyl-4'-[(5,7-diethyl-2-oxo-1,2-dihydro-1,6-naphthyridin-1-yl)methyl]biphenyl-2-sulphonamide hydrochloride as an amorphous solid (153 mg); NMR (d₆-DMSO): 1.27(t, 3H), 1.31(t, 2H), 1.69(s, 3H), 2.99(q, 2H), 3.36(q, 2H), 5.63(s, 2H), 6.98(d, 1H), 7.2-7.4(complex m, 5H), 7.5-7.8(m, 3H), 8.06(dd, 1H), 8.40(d, 1H), 11.53(s, 1H); mass spectrum (+ve FAB, methanol/NBA): 490 (M+H)⁺; microanalysis, found: C, 59.9; H, 5.4; N, 7.7%; C₂₇H₂₇N₃O₄S.HCl.H₂O requires: C, 59.6; H, 5.5; N, 7.7%.

EXAMPLE 40

A solution of ethyl isocyanate (0.04 ml) in acetone (2 ml) and a solution of sodium hydroxide (1M aqueous sodium hydroxide solution (0.5 ml) diluted with acetone (1.5 ml)) were added dropwise and simultaneously to a stirred and ice-cooled solution of 4'-[(5,7-diethyl-2-oxo-1,2-dihydro-1,6-napthyridin-1-yl)methyl]biphenyl-2-sulphonamide (220 mg) in acetone (20 ml). When the addition was complete the mixture was stirred and allowed to warm to ambient temperature. After 2 hours a further quantity of ethyl isocyanate (0.2 ml) was added and the mixture was stirred for a further 1 hour. Volatile material was removed by evaporation and water (20 ml) was added to the residue. The mixture was acidified to pH 5 by the addition of acetic acid and then saturated with solid sodium chloride. The mixture was extracted twice with ethyl acetate and the combined extracts were washed with saturated sodium chloride solution and dried (MgSO₄). The solvent was removed by evaporation to give 1-ethyl-3-[4'-(5,7-diethyl-2-oxo-1,2-dihydro-1,6-naphthyridin-1-ylmethyl)biphenyl-2-ylsulphonyl]urea (117 mg) as a solid, m.p. 183°-184° C. (after recrystallisation from ethyl acetate/petroleum ether); NMR (d₆-DMSO): 0.89(t, 3H), 1.19(t, 3H), 1.26(t, 3H), 2.73(q, 2H), 2.90(dq, 2H), 3.07(q, 2H), 5.55(s, 2H), 6.03(t, 1H), 6.73(d, 1H), 7.18(s, 1H), 7.2-7.35(m, 5H), 7.58(dt, 1H), 7.65(dt, 1H), 8.03(dd, 1H), 8.24(d, 1H), 9.88(s, 1H); mass spectrum (+ve FAB, DMSO/NBA): 519 (M+H)⁺; microanalysis, found: C, 65.0, H, 5.7, N, 10.8%; C₂₈H₃₀N₄O₄S requires: C, 64.8; H, 5.8; N, 10.8%.

EXAMPLE 41

Using an analogous procedure to that described in Example 2, but starting from 5,7-diethyl-1-[(2'-(2-triphenylmethyl-2H-tetrazol-5-yl)biphenyl-4-yl)methyl]-1,6-naphthyridin-4(1H)-one (A), there was thus obtained 5,7-diethyl-1-[(2'-(1H-tetrazol-5-yl)biphenyl-4-yl)methyl]-1,6-napthyridin-4(1H)-one hydrochloride as a solid, in 76% yield; m.p. 218°-220° C. (decomposition); NMR (d₆-DMSO): 1.15-1.34(m, 6H), 2.97(q, 2H), 3.60(q, 2H), 5.58(s, 2H), 6.40(d, 1H), 7.11(d, 2H), 7.26(d, 2H), 7.45-7.72(m, 5H), 8.29(d, 1H); mass spectrum (+ve FAB, DMSO/NBA): 437 (M+H)⁺; microanalysis, found: C, 64.7; H, 5.5; N, 17.4%; C₂₆H₂₄N₆O.HCl.0.5H₂O requires: C, 64.8; H, 5.2; N, 17.4%

The starting material (A) was obtained as follows:

(i) A mixture of 4-amino-2,6-diethylpyridine (0.85 g) and diethyl ethoxymethylenemalonate (1.25 g) was heated at 110° C. for 1 hour. A eutectic mixture of 26.5% v/v diphenyl and 73.5% v/v diphenyl oxide (5 ml) was added and the mixture was heated at reflux for 10 minutes. The mixture was cooled and diluted with hexane (70 ml). The resultant precipitate was collected by filtration to give ethyl 5,7-diethyl-4-oxo-1,4-dihydro-1,6-naphthyridine-3-carboxylate (B) as a light brown solid (1.02 g), m.p. 210°-215° C.; NMR (d₆-DMSO): 1.15-1.35(m, 9H), 2.77(q, 2H), 3.34(q, 2H), 4.21(q, 2H), 7.13(s, 1H), 8.42(s, 1H), 12.10 (brs, 1H).

(ii) A mixture of compound B (1.0 g) and 1M sodium hydroxide solution (20 ml) was heated on a steam-bath for 3 hours. The mixture was cooled, diluted with water (20 ml) and acidified to pH6 will 2M hydrochloric acid solution. The precipitated solid was collected by filtration and recrystallised from acetone to give 5,7-diethyl-4-oxo-1,4-dihydro-1,6-naphthyridine-3-carboxylic acid (C) (533 mg) as a solid, m.p. 246°-248° C. (decomposition); NMR (d₆-DMSO): 1.24(t, 3H), 1.28(t, 3H), 2.85(q, 2H), 3.45(q, 2H), 7.34(s, 1H), 8.87(s, 1H), 15.02(brs, 1H).

(iii) Compound C (510 mg) was heated at 250° C. for 10 minutes. The residue was cooled to ambient temperature and purified by flash chromatography, eluting with methanol/dichloromethane (5: 95 v/v), to give 5,7-diethyl-1,6-napthyridin-4(1H)-one (350 mg) as a solid, m.p. 207°-208° C.; NMR (d₆-DMSO): 1.17(t, 3H), 1.24(t, 3H), 2.74(q, 2H), 3.36(q, 2H). 6.04(dd, 1H), 7.04(s, 1H), 7.78(dd, 1H), 11.58(brs, 1H); mass spectrum (+ve CI): 203 (M+H)⁺; microanalysis; found: C, 70.2; H, 6.7, N, 13.6%; C₁₂H₁₄N₂O.0.2H₂O requires C, 70.0, H, 7.0, N, 13.6%.

(iv) Using an analogous procedure to that described in Example 1, but starting from 5,7-diethyl-1,6-napthyrid-4(1H)-one there was obtained 5,7-diethyl-1-[2'-(2-triphenylmethyl-2H-tetrazol-5-yl)biphenyl-4-yl)methyl]-1,6-napthyridin-4(1H)-one as a solid, in 70% yield; m.p. 175°-178° C. (decomposition); NMR: 1.09(t, 3H), 1.24(t, 3H), 2.62(q, 2H), 3.46(q, 2H), 4.96(s, 2H), 6.16(d, 1H), 6.67(s, 1H), 6.75-6.88(m, 6H), 7.0-7.28(m, 15H), 7.30-7.44(m, 2H), 7.80-7.88(m, 1H); ¹³C NMR: (benzylic CH$_2$) 55.7; mass spectrum (+ve FAB, methanol/NBA): 679 (M+H)$^+$; microanalysis, found: C, 78.5; H, 5.8; N, 12.4%; C$_{45}$H$_{38}$N$_6$O.0.25(CH$_3$CO$_2$C$_2$H$_5$) requires: C, 78.9, H, 5.7, N, 12.0%.

EXAMPLE 42

2M Sodium hydroxide solution (3 ml) was added to a solution of methyl 4'-[(5,7-diethyl-2-oxo-1,2-dihydro-1,6-naphthyridin-1-yl)methyl]biphenyl-2-carboxylate (A) (300 mg) in methanol (5 ml) and the mixture was heated at reflux for 2 hours. The mixture was cooled to ambient temperature and volatile material was removed by evaporation. The residue was dissolved in water and the solution adjusted to pH 5 with acetic acid. The precipitated solid was collected by filtration to give 4'-[(5,7-diethyl-2-oxo-1,2-dihydro-1,6-naphthyridin-1-yl)methyl]biphenyl-2-carboxylic acid (100 mg) as a solid; m.p. 238°–240° C.; NMR (d$_6$-DMSO): 1.18(t, 3H), 1.26(t, 3H), 2.72(q, 2H), 3.60(q, 2H), 5.2(s, 2H), 6.70(d, 1H), 7.15(s, 1H), 7.23–7.71(m, 5H), 8.21(d, 1H), 12.65(broad s, 1H); mass spectrum (+ve FAB, methanol/NBA): 435 (M+Na)$^+$, 413(M+H)$^+$; microanalysis, found: C, 74.1; H, 5.6; N, 6.5%; C$_{26}$H$_{26}$N$_2$O$_3$.0.5.H$_2$O requires; C, 74.0; H, 5.9; N, 6.6%.

The starting material A was obtained as follows:

5,7-Diethyl-1,6-naphthyridin-2(1H)-one (404 mg) was added to a mixture of potassium tert-butoxide (235 mg) and 1,4,7,10,13,16-hexaoxacyclooctadecane (20 mg) in THF (20 ml) and the mixture was stirred for 5 minutes. Methyl 4'-(bromomethyl)biphenyl-2-carboxylate (710 mg) (prepared as described in European patent application, publication no. 291969) was added and the mixture was stirred for 16 hours. Volatile material was removed by evaporation and the residue was purified by flash chromatography eluting with ethyl acetate/hexane (1:1 v/v) to give methyl 4'-[(5,7-diethyl-2-oxo-1,2-dihydro-1,6-naphthyridin-1-yl)methyl]biphenyl-2-carboxylate (A) (680 mg) as a foam; NMR (d$_6$-DMSO): 1.18(t, 3H), 1.25(t, 3H), 2.72(q, 2H), 3.06(q, 2H), 3.54(s, 3H), 5.53(s, 2H), 6.72(d, 1H), 7.14(s, 1H), 7.20–7.74(m, 8H), 8.22(s, 1H); mass spectrum (CI, ammonia): 427 (M+H)$^+$.

EXAMPLE 43

Using an analogous procedure to that described in Example 1, but starting from 5-methyl-7-propyl-1-[(2'-(2-triphenylmethyl-2H-tetrazol-5-yl)biphenyl-4-yl)methyl]-1,6-naphthyridin-2(1H)-one (A), there was thus obtained 5-methyl-7-propyl-1-[(2'-(1H-tetrazol-5-yl)biphenyl-4-yl)methyl]-1,6-naphthyridin-2(1H)-one hydrochloride as a solid, in 22% yield; m.p. 219°–221° C.; NMR (d$_6$-DMSO): 0.84(t, 3H), 1.79(m, 2H), 2.93(t, 2H), 2.50(s, 3H), 5.55(s, 2H), 6.95(d, 1H), 7.04–7.69(m, 9H), 8.30(d, 1H); mass spectrum (+ve FAB, methanol/NBA): 437 (M+H)$^+$; microanalysis, found: C, 63.7; H, 5.7; N, 17.1%; C$_{26}$H$_{24}$N$_6$O.HCl.H$_2$O requires: C, 63.5; H, 5.5; N, 17.1%.

The starting material A was prepared as follows:

(i) Using an analogous procedure to that described in Example 2, part (i), but starting from 3-amino-2-hexenenitrile (obtained as described in *J. Het. Chem.*, 1989, 26, 1575–8) and methyl acetoacetate, there was thus obtained methyl 4-amino-2-methyl-6-propylpyridine-3-carboxylate (B) as a solid, in 72% yield; m.p. 72°–76° C.; NMR (d$_6$-DMSO): 0.88(t, 3H), 1.6(m, 2H), 2.42(t, 2H), 3.80(s, 3H), 6.8(s, 1H), 6.63(broad s, 2H).

(ii) Using an analogous procedure to that described in Procedure 1, part (iv), but starting from compound B, there was thus obtained 4-amino-3-hydroxymethyl-2-methyl-6-propylpyridine (C) as a solid, in 97% yield; m.p. 98°–101° C.; NMR (d$_6$-DMSO): 0.94(t, 3H), 1.64(m, 2H), 2.37(s, 3H), 2.46(t, 2H), 4.47(s, 2H), 4.77(s, 1H), 5.65(s, 2H), 6.32(s, 1H); mass spectrum (CI, ammonia): 181 (M+H)$^+$.

(iii) Using an analogous procedure to that described in Procedure 1, part (v), but starting from compound C, there was thus obtained 4-amino-2-methyl-6-propyl-pyridine-3-carbaldehyde (D) as a solid, in 100% yield; m.p. 94°–97° C.; NMR (d$_6$-DMSO): 0.89(t, 3H), 1.61(m, 2H), 2.45(t, 2H), 2.59(s, 3H), 6.37(s, 1H), 7.72(s, 2H), 10.24(s, 1H); mass spectrum (CI, ammonia): 179 (M+H)$^+$.

(iv) Using an analogous procedure to that described in Procedure 1, part (vi), but starting from compound D, there was thus obtained 5-methyl-7-propyl-1,6-naphthyridin-2(1H)-one (E) as a solid, in 40% yield; m.p. 148°–150° C.; NMR (d$_6$-DMSO): 0.91(t, 3H), 1.48(m, 2H), 2.64(s, 3H), 2.68(t, 2H), 6.48(d, 1H), 6.90(s, 1H), 8.05(d, 1H), 11.85(s, 1H); mass spectrum (CI, ammonia): 203 (M+H)$^+$.

(v) Using an analogous procedure to that described in Example 1, but starting from compound E and 5-[2-(4'-bromomethylbiphenylyl)]-2-triphenylmethyl-2H-tetrazole, there was thus obtained 5-methyl-7-propyl-1-[(2'-(2-triphenylmethyl-2H-tetrazol-5-yl)biphenyl-4-yl)methyl]-1,6-naphthyridin-2(1H)-one (A) as a foam, in 70% yield; NMR (d$_6$-DMSO): 0.76(t, 3H), 1.55(m, 2H), 2.51(t, 2H), 2.57(s, 3H), 5.45(s, 2H), 6.65(d, 1H), 6.8–7.8-(complex m, 25H), 8.16(d, 1H); mass spectrum (+ve FAB, methanol/NBA): 679 (M+H)$^+$.

EXAMPLE 44

Using an analogous procedure to that described in Example 2, but starting from 5-methyl-7-propyl-1-[(2'-(2-triphenylmethyl-2H-tetrazol-5-yl)biphenyl-4-yl)methyl]-1,2,3,4-tetrahydro-1,6-naphthyridin-2-one (A), there was thus obtained 5-methyl-7-propyl-1-[(2'-(1H-tetrazol-5-yl)biphenyl-4-yl)methyl]-1,2,3,4-tetrahydro-1,6-naphthyridin-2-one hydrochloride as a solid, in 58% yield; m.p. 226°–228° C.;NMR (d$_6$-DMSO): 0.77(t, 3H), 1.58(m, 2H), 2.64(s, 3H), 2.83(m, 4H), 3.01(t, 2H), 5.24(s, 2H), 7.04(d, 2H), 7.17 (s, 1H), 7.20(d, 2H), 7.42–7.7(m, 4H); mass spectrum (+ve FAB, DMSO/thioglycerol/glycerol/trifluoroacetic acid): 439 (M+H)$^+$; microanalysis, found: C, 64.5; H, 5.8; N, 17.6%; C$_{26}$H$_{26}$N$_6$O.HCl.0.5H$_2$O requires: C, 64.4; H, 5.8; N, 17.4%.

The starting material A was prepared as follows:

(i) Using an analogous procedure to that described in Procedure 3, but starting from 5-methyl-7-propyl-1,6-naphthyridin-2(1H)-one (B), there was thus obtained 5-methyl-7-propyl-1,2,3,4-tetrahydro-1,6-naphthyridin-2-one (C) as a solid in 95% yield; NMR (d$_6$-DMSO): 0.89(t, 3H), 1.60(m, 2H), 2.34(s, 3H), 2.5(m, 4H), 2.81(t, 2H), 6.49(s, 1H), 10.21(broad s, 1H).

(ii) Using an analogous procedure to that described in Example 42, but starting from compound C and 5-[2-(4'-bromomethylbiphenylyl)]-2-triphenylmethyl-2H-tetrazole there was obtained 5-methyl-7-propyl-1-[2'-(2-triphenylmethyl-2H-tetrazol-5-yl)biphenyl-4-yl)methyl]-1,2,3,4-tetrahydro-1,6-naphthyridin-2-one (A) as a foam, in 40% yield; NMR (d$_6$-DMSO): 0.70(t, 3H), 1.47(m, 2H), 2.39(m, 5H), 2.74(d, 2H), 2.86(d, 2H), 5.1(s, 2H), 6.62(s, 1H), 6.83–7.78(complex m, 23H); mass spectrum (+ve FAB, DMSO/NBA): 703 (M+Na)$^+$, 681 (M+H)$^+$.

EXAMPLE 45

Using an analogous procedure to that described in Example 2, but starting from 5,7-diethyl-2-oxo-1-[(2'-(2-triphenylmethyl-2H-tetrazol-5-yl)biphenyl-4-yl)methyl]-1,2,3,4-tetrahydro-1,6-naphthyridine-6-oxide (A), there was thus obtained 5,7-diethyl-2-oxo-1-[(2'-(1H-tetrazol-5-yl)biphenyl-4-yl)methyl]-1,2,3,4-tetrahydro-1,6-naphthyridine-6-oxide hydrochloride as a solid, in 38% yield; m.p. 182°-190° C.; NMR (d$_6$-DMSO): 1.1–1.3(m, 6H), 2.8–3.2(m, 8H), 5.2(s, 2H), 7.1(d+s, 3H), 7.25(d, 2H), 7.5–7.7(m, 4H); mass spectrum (+ve FAB, methanol/NBA): 455 (M+H)$^+$; microanalysis, found: C, 63.6; H, 5.7; N, 16.7%; C$_{26}$H$_{26}$N$_6$O$_2$.HCl requires: C, 63.6; H, 5.5; N, 17.1%.

The starting material (A) was obtained as follows:

A solution of 5,7-diethyl-1-[(2'-(2-triphenylmethyl-2H-tetrazol-5-yl)biphenyl-4-yl)methyl]-1,2,3,4-tetrahydro-1,6-naphthyridin-2-one (0.95 g) and m-chloroperbenzoic acid (0.85 g) in chloroform (50 ml) was heated at reflux for 2 hours. Saturated sodium carbonate solution (50 ml) was added and the organic layer was separated, washed with saturated sodium chloride solution (50 ml) and dried (MgSO$_4$). The solvent was removed by evaporation and the residue was purified by flash chromatography, eluting with methanol/ethyl acetate (1:9 v/v), to give 5,7-diethyl-2-oxo-1-[(2'-(2-triphenyl-2H-tetrazol-5-yl)biphenyl-4-yl)methyl]-1,2,3,4-tetrahydro-1,6-naphthyridine-6-oxide (A) (330 mg) as a foam; NMR: 1.1(t, 6H), 2.7–2.9(m, 4H), 2.95–3.15(m, 4H), 5.1(s, 2H), 6.6(s, 1H), 6.9–7.05(m, 8H), 7.15(d, 2H), 7.2–7.4(m, 10H), 7.45–7.5(m, 2H), 7.9–7.95(m, 1H).

EXAMPLE 46

5,7-Diethyl-1-[(2'-(1-(4-nitrophenyl)-1H-tetrazol-5-yl)biphenyl-4-yl)methyl]-1,2,3,4-tetrahydro-1,6-naphthyridin-2-one (A) (5.0 g) was added to a solution of sodium (2.05 g) in methanol (100 ml) and the solution was heated at reflux for 16 hours under an atmosphere of argon. The mixture was cooled to 0° C. and acidified with concentrated hydrochloric acid (20 ml). The precipitated solid was collected by filtration and recrystallised successively from isopropanol (60 ml), water (30 ml) and ethanol (10 ml) to give 5,7-diethyl-1-[(2'-(1H-tetrazol-5-yl)biphenyl-4-yl)methyl]-1,2,3,4-tetrahydro-1,6-naphthyridin-2-one hydrochloride (2.36 g), m.p. 260°-263° C. (decomposition); microanalysis, found: C, 65.6; H, 5.9; N, 17.8%; C$_{26}$H$_{26}$N$_6$O.HCl requires: C, 65.7; H, 5.7; N, 17.7.

The starting material (A) was obtained as follows:

(i) Thionyl chloride (120.5 g) was added to a stirred mixture of 2-bromobenzoic acid (194 g) in toluene (500 ml) and DMF (5 ml) and the mixture was heated at 80° C. for 4 hours. The solution was cooled to 20° C. and added slowly to a solution of 4-nitroaniline (133.1 g) in toluene (500 ml) and N-methylpyrrolidone (NMP) (120 ml), maintaining the temperature of the reaction mixture between 20°-25° C. The reaction mixture was then stirred for 24 hours when a solid precipitated. Water (360 ml) was added with rigorous stirring and the suspended solid was collected by filtration and washed successively with water, toluene and acetonitrile to give 2-bromo-N-(4-nitrophenyl)benzamide (B) as a solid, in 87% yield; m.p. 200°-202° C.; NMR (d$_6$-DMSO): 7.4–7.8(m, 7H), 8.0(d, 2H), 8.3(d, 2H), 11.5(brs, 1H); which was used without further purification.

(ii) Triethylamine (1.04 g) was added to a mixture of amide B (3 g) in acetonitrile (12 ml) and DMF (0.189 g) and the mixture was stirred for 90 minutes. Thionyl chloride (1.44 g) was then added slowly keeping the reaction temperature below 25° C. The mixture was stirred for 5 hours at ambient temperature and then cooled to 10° C. Triethylamine (2.83 g) was then added, followed by sodium azide (1.33 g) and tetrabutylammonium bromide (0.42 g). The mixture was stirred for 2 hours at 10° C. and then allowed to warm to ambient temperature and stirred for 24 hours. The mixture was poured into excess water and the precipitated solid collected by filtration. The solid was purified by trituration with a hot mixture of ethyl acetate (26 ml), hexane (2.6 ml) and triethylamine (0.1 ml) to give 5-(2-bromophenyl)-1-(4-nitrophenyl)-1H-tetrazole (C) (2.36 g; 73% yield) as an off-white solid, m.p. 169°-170° C.; NMR (d$_6$-acetone; 270 MHz): 7.61–7.86(m, 6H), 8.41(d, 2H); microanalysis, found: C, 44.8; H, 2.1; N, 20.0; Br, 23.6%; C$_{13}$H$_8$BrN$_5$O$_5$ requires: C, 45.11 H, 2.3; N, 20.2; Br, 23.1%.

(iii) A mixture of 4-methylphenylboronic acid (9.7 g), sodium carbonate (16.7 g), water (100 ml), methanol (50 ml) and toluene (50 ml) was heated to 60° C. to give a clear solution. Compound C (20.0 g) was then added, followed by tetrakis(triphenylphosphine)palladium(0) (0.3 g) and the mixture heated at reflux for 3 hours. Toluene (30 ml) was added and the warm mixture was filtered through diatomaceous earth. The organic phase was separated and the aqueous phase was extracted with toluene (40 ml). The combined organic phases were evaporated to give a solid which was recrystallised from toluene/petroleum ether (100°-120° C.) (1:1 v/v) to give 5-(4'-methylbiphenyl-2-yl)-1-(4-nitrophenyl)-1H-tetrazole (D) (18.7 g; 90% yield), m.p. 164°-166° C.; NMR (CDCl$_3$): 2.3(3H, s), 6.45(2H, d), 6.85(4H, m), 7.38(1H, d), 7.65(2H, m), 7.85(1H, d), 8.0(2H, d).

(iv) A mixture of compound D (8.0 g), N-bromosuccinimide (4.53 g) and azo(bisisobutyronitrile) (73 mg) in methyl chloroform (50 ml) was heated at reflux for 4 hours. The mixture was cooled to ambient temperature, washed with water (3×50 ml), and the suspended solid collected by filtration to give 5-(4'-bromomethylbiphenyl-2-yl)-1-(4-nitrophenyl)-1H-tetrazole (E) (7.3 g), m.p. 192°-195° C.; NMR (CDCl$_3$): 4.4(2H, s), 6.52(2H, d) 6.85(2H, d), 7.07(2H, d), 7.4(1H, d), 7.7(2H, m), 7.9(1H, d).

(v) Potassium tert-butoxide (2.3 g) was added to a solution of 5,7-diethyl-1,2,3,4-tetrahydro-1,6-naphthyridin-2-one (3.5 g) in THF (70 ml) at 0° C. The mixture was stirred for 10 minutes and then compound E (9.5 g) was added. The mixture was stirred for 4 hours and then volatile material was removed by evaporation. Water (50 ml) was added to the residue and the mixture was extracted with ethyl acetate (2×100 ml). The extracts were washed with saturated sodium chloride solution (2×50 ml) and then dried (MgSO$_4$). The solvent was removed by evaporation and the residue was purified by flash chromatography, eluting with ethyl acetate/hexane (1:1 v/v), to give 5,7-diethyl-1-[(2'-(1-(4-nitroophenyl)-1H-tetrazol-5-yl)biphenyl-4-yl)methyl]-1,2,3,4-tetrahydro-1,6-naphthyridin-2-one (A) (4.3 g) as a solid, m.p. 170°-172° C. (after recrystallisation from toluene/hexane); NMR (CDCl$_3$): 1.15(t, 3H), 1.25(t, 3H), 2.7(q, 2H), 2.8–2.95(m, 4H), 3.0–3.1(m, 2H), 5.1(s, 2H), 6.5(s+d, 3H), 6.7(d, 2H), 6.85(d, 2H), 7.35(dd, 1H), 7.6–7.7(m, 2H), 7.75–7.85(m, 2H), 7.9(dd, 1H).

EXAMPLE 47

5,7-Diethyl-1-[(2'-(1-(4-nitrophenyl)-1H-tetrazol-5-yl)biphenyl-4-yl)methyl]-1,6-naphthyridin-2(1H)-one (A) (2.5 g) was added to a solution of sodium (1.65 g) in methanol (100 ml) and the solution was heated at reflux for 36 hours under an atmosphere of argon. Volatile material was removed by evaporation and water (50 ml) was added. The mixture was extracted with ether (2×50 ml) and the aqueous phase was cooled to 0° C. and acidified to pH 5-6 with 20% aqueous citric acid solution. The precipitated solid was collected by filtration, washed with water (20 ml) and hexane (30 ml), and dried under vacuum at 40° C. The solid was suspended in hot ethanol (20 ml) and a saturated solution of hydrogen chloride in ethanol (10 ml) was added. The solid that crystallised out on cooling was collected by filtration and washed with acetone (20 ml) to give 5,7-diethyl-1-[(2'-(1H-tetrazol-5-yl)biphenyl-4-yl)methyl]-1,6-naphthyridin-2(1H)-one hydrochloride (1.26 g); m.p. 272°-273° C.; microanalysis, found: C, 65.1; H, 5.5; N, 16.8%; $C_{26}H_{24}N_6O.HCl.0.5(C_2H_5OH)$ requires: C, 65.3; H, 5.6; N, 16.9%.

The starting material (A) was obtained as follows:

A mixture of 5,7-diethyl-1,6-naphthyridin-2(1H)-one (10.0 g), benzyltriethylammonium chloride (1.1 g), 50% aqueous sodium hydroxide solution (28.4 ml) and toluene (200 ml) was stirred at 50° C. until all solid material dissolved. 5-(4'-Bromomethylbiphenyl-2-yl)-1-(4-nitrophenyl)-1H-tetrazole (24.8 g) was added and the mixture was heated under reflux for 24 hours. The organic layer was separated and last traces of water were removed azeotropically by heating in a Dean-Stark apparatus. Hexane (180 ml) was added to precipitate 5,7-diethyl-1-[(2'-(1-(4-nitrophenyl)-1H-tetrazol-5-yl)biphenyl-4-yl)methyl]-1,6-naphthyridin-2(1H)-one (A) (17.5 g), m.p. 216°-219° C.; NMR (CDCl$_3$): 1.3(t, 3H), 1.4(t, 3H), 2.85(q, 2H), 3.15(q, 2H), 5.4(s, 2H), 6.5(d, 2H), 6.65-6.75(m, 2H), 6.8-6.9(m, 4H), 7.3-7.35(m, 1H), 7.6-7.9(m, 5H), 8:1(d, 1H).

EXAMPLE 48 (Note: all parts by weight)

The compounds of the invention may be administered for therapeutic or prophylactic use to warm-blooded animals such as man in the form of conventional pharmaceutical compositions, typical examples of which include the following:

| a) | Capsule (for oral administration) | |
|---|---|---|
| | Active ingredient* | 20 |
| | Lactose powder | 578.5 |
| | Magnesium stearate | 1.5 |
| b | Tablet (for oral administration) | |
| | Active ingredient* | 50 |
| | Microcrystalline cellulose | 400 |
| | Starch (pregelatinised) | 47.5 |
| | Magnesium stearate | 2.5 |
| c) | Injectable Solution (for intravenous administration) | |
| | Active ingredient* | 0.05-1.0 |
| | Propylene glycol | 5.0 |
| | Polyethylene glycol (300) | 3.0-5.0 |
| | Purified water | to 100% |
| d) | Injectable Suspension (for intramuscular administration) | |
| | Active ingredient* | 0.05-1.0 |
| | Methylcellulose | 0.5 |
| | Tween 80 | 0.05 |
| | Benzyl alcohol | 0.9 |
| | Benzalkonium chloride | 0.1 |
| | Purified water | to 100% |

Note:
the active ingredient* may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

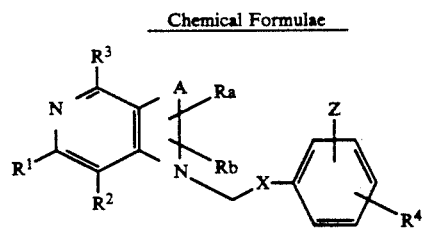

I

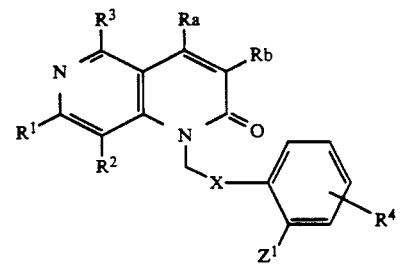

Ia

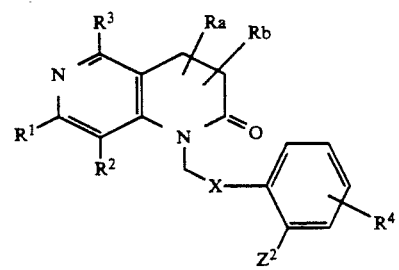

Ib

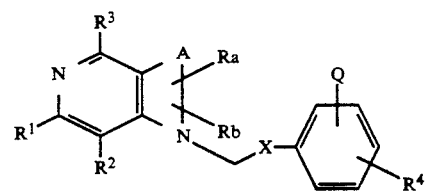

II

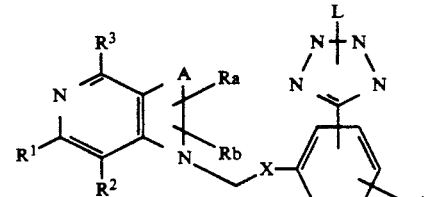

III

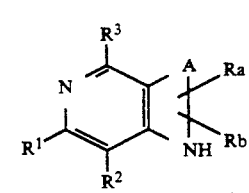

IV

-continued
Chemical Formulae
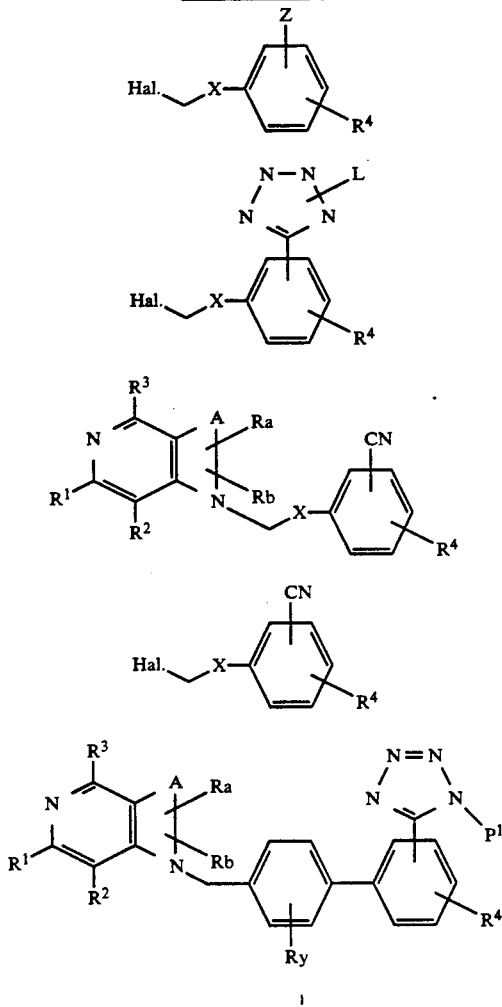
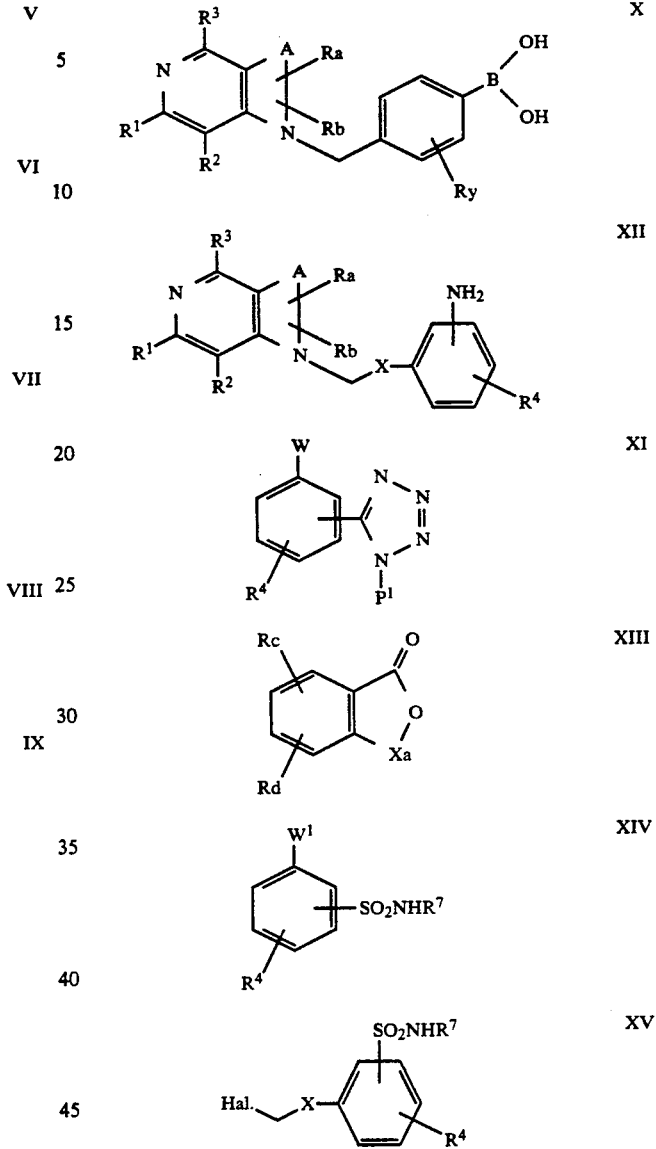
Scheme 1
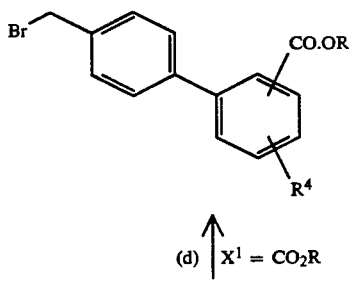

-continued
Scheme 1
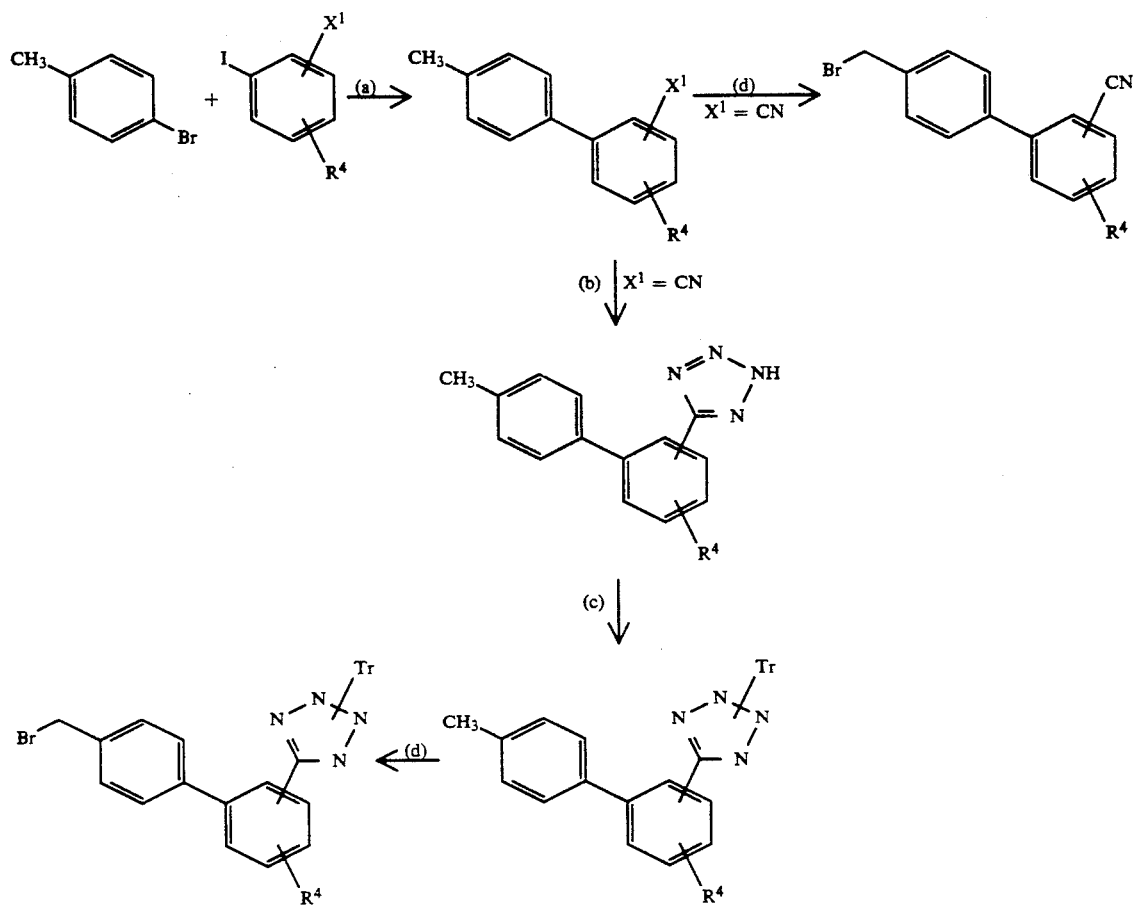
Note:
R = lower alkyl, benzyl, phenyl; Tr = triphenylmethyl (trityl)
Reagents:
(a) BuLi/THF; ZnCl$_2$/Et$_2$O; Pd(Ph$_3$P)$_4$
(b) Bu$_3$Sn.N$_3$/toluene; HCl/toluene
(c) Tr.Cl/Et$_3$N/CH$_2$Cl$_2$
(d) N-bromosuccinimide/azoisobutyronitrile/CCl$_4$
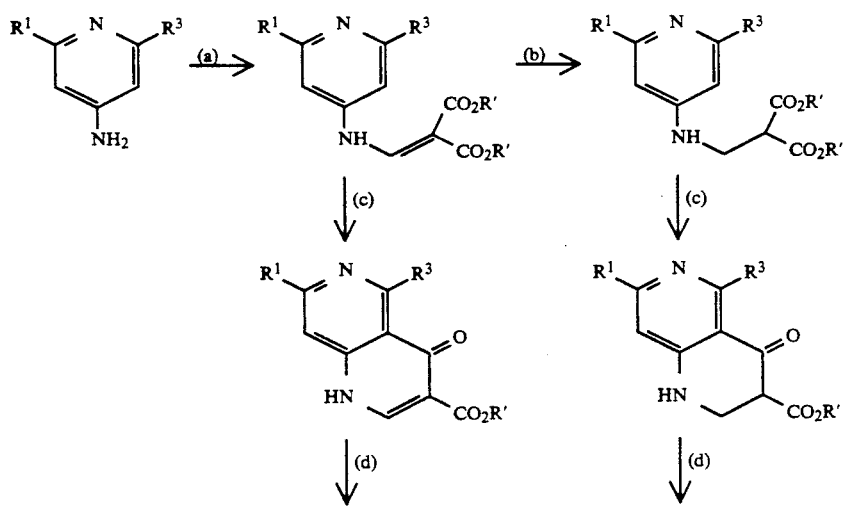
Scheme 2

Scheme 2

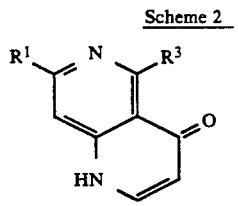
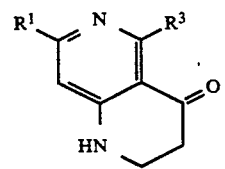

Note:
R' = lower alkyl
Reagents:
(a) R'OCH=C(CO$_2$R')$_2$, 110° C.
(b) hydrogen, Pd on C or PtO$_2$
(c) Ph—Ph/Ph—O—Ph mixture, reflux
(d) (i) NaOH; (ii) as for step (c)

Scheme 2a

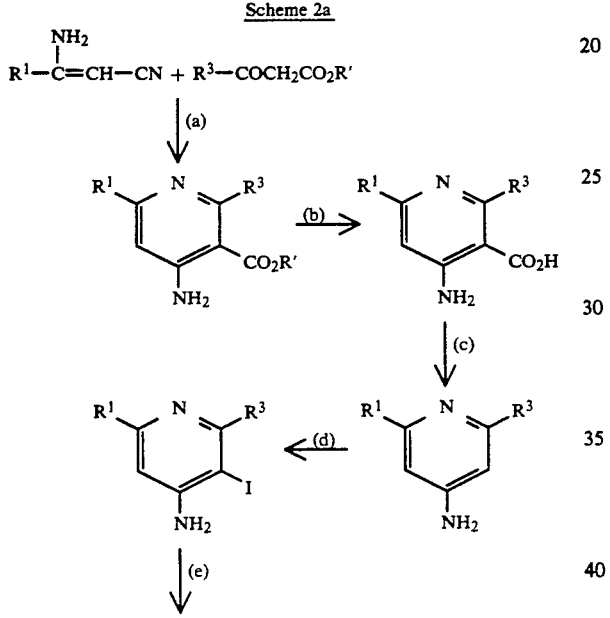

-continued
Scheme 2a

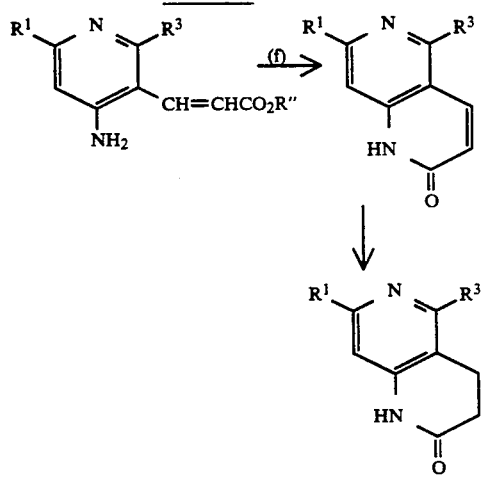

Note:
R' = lower alkyl; R" = lower alkyl
Reagents:
(a) SnCl$_4$, toluene, reflux
(b) aqu. NaOH, methanol, reflux; then HCl
(c) heat, 220° C.
(d) I$_2$, [bis(trifluoroacetoxy)iodo]benzene, CH$_2$Cl$_2$, methanol
(e) Pd(II)acetate, tri(2-methylphenyl)phosphine, Et$_3$N, DMF, 130° C., CH$_2$=CHCO$_2$R"
(f) NaOCH$_3$, methanol, reflux
(h) hydrogen, palladium on carbon, acetic acid/ethanol, 20 atmospheres, 70° C.

Scheme 2b

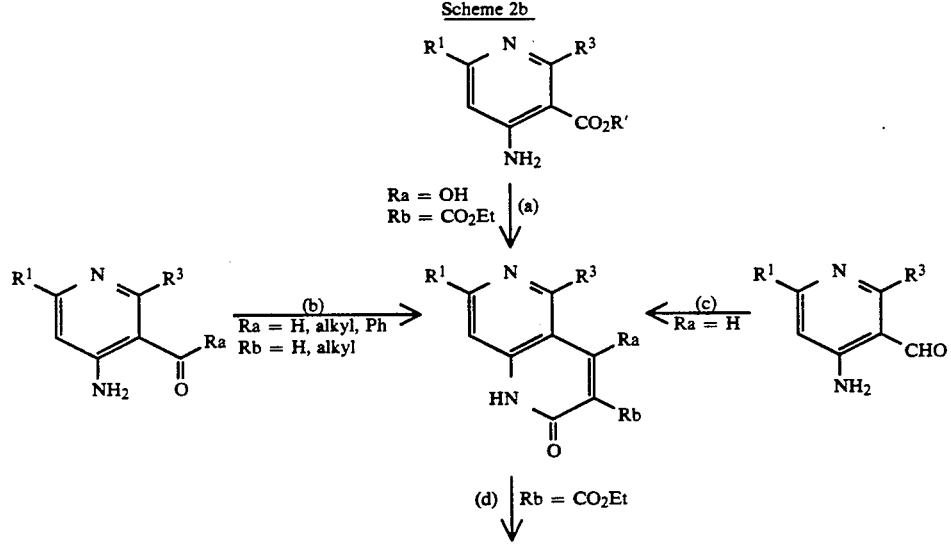

-continued
Scheme 2b

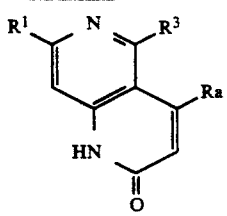

Note:
Et = ethyl; Ph = phenyl; R' = lower alkyl
Reagents:
(a) diethyl malonate, NaOEt, EtOH, 150° C., autoclave
(b) Ph₃P=C(Rb)CO₂Et, xylene or toluene, reflux
(c) RbCH₂CO₂Et (e.g. Rb = CO₂Et, Ph, Pyridyl, CN, SPh), EtOH, piperidine, reflux
(d) aqu.HCl, dioxan, reflux Scheme 3

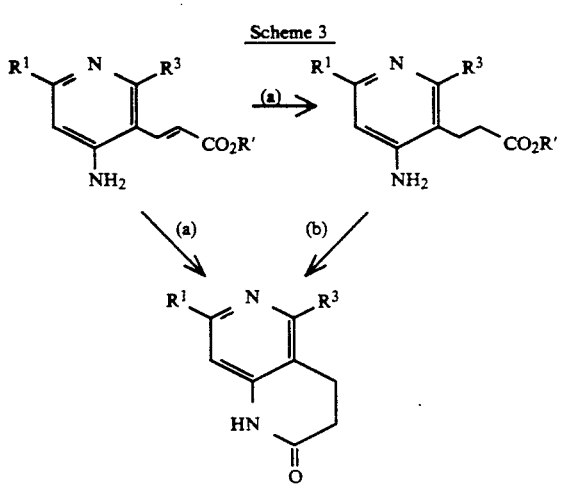

Note:
R' = lower alkyl
Reagents:
(a) hydrogen, Pd on C or PtO₂
(b) heat

Scheme 4

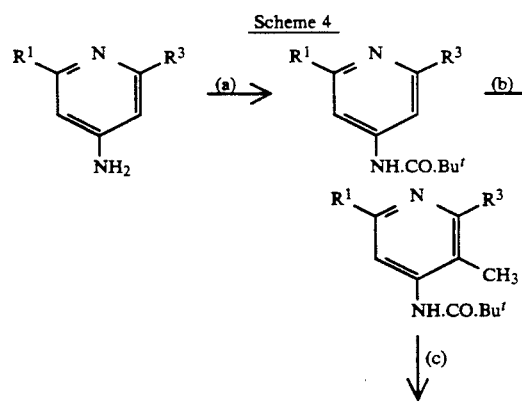

-continued
Scheme 4

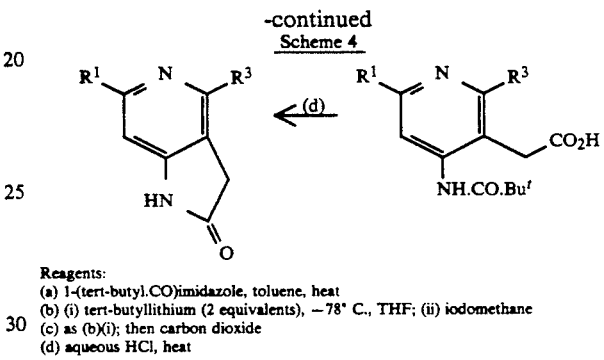

Reagents:
(a) 1-(tert-butyl.CO)imidazole, toluene, heat
(b) (i) tert-butyllithium (2 equivalents), −78° C., THF; (ii) iodomethane
(c) as (b)(i); then carbon dioxide
(d) aqueous HCl, heat Scheme 5

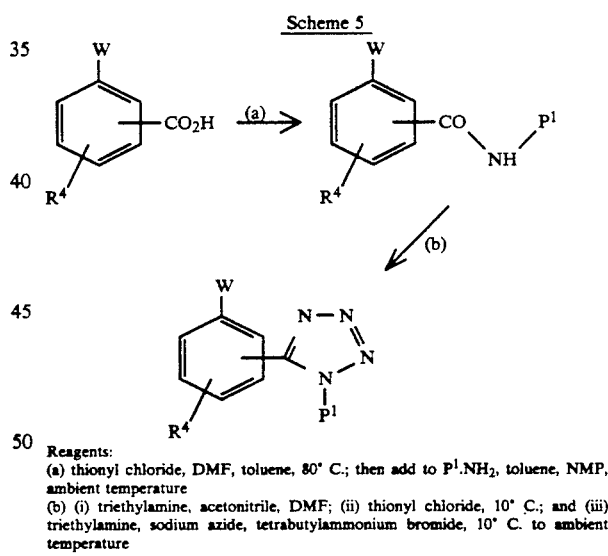

Reagents:
(a) thionyl chloride, DMF, toluene, 80° C.; then add to P¹.NH₂, toluene, NMP, ambient temperature
(b) (i) triethylamine, acetonitrile, DMF; (ii) thionyl chloride, 10° C.; and (iii) triethylamine, sodium azide, tetrabutylammonium bromide, 10° C. to ambient temperature Scheme 6

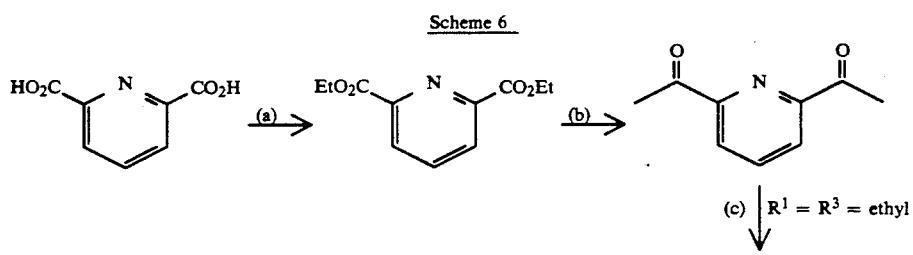

(c) | R¹ = R³ = ethyl

Scheme 6

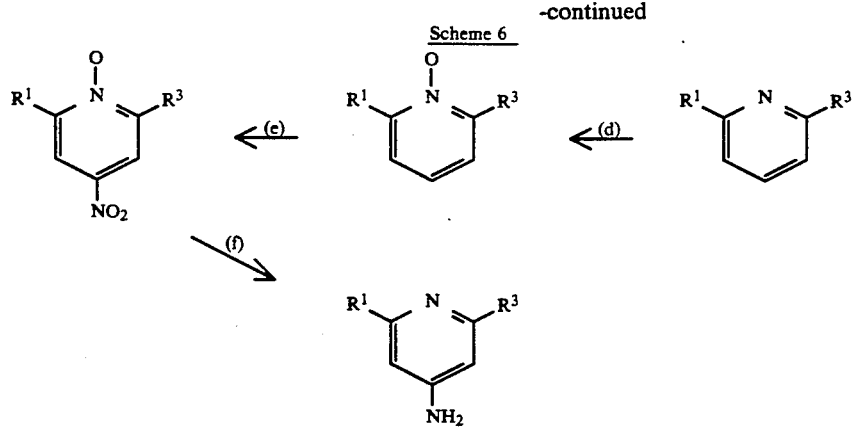

-continued

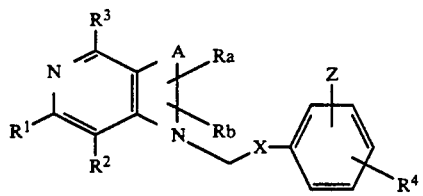

Reagents:
(a) thionyl chloride, ethanol, DMF, 70° C. to reflux
(b) (i) NaOEt, t-butyl acetate, 1,2-dimethoxyethane, reflex (ii) aqu. HCl, reflux
(c) (i) hydrazine hydrate, ethanol, reflux (ii) potassium t-butoxide, toluene, reflux
(d) hydrogen peroxide, acetic acid, 20–90° C.
(e) Conc. sulphuric acid, conc. nitric acid, 90° C.
(f) (i) PCl$_3$, chloroform, reflux (ii) catalytic hydrogenation over palladium on carbon

What we claim is:

1. A heterocyclic derivative of the formula I wherein $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, (1–4C)alkoxy or phenyl substituent; $R^2$ is hydrogen, (1–4C)alkyl, (1–4C)alkoxy, halogeno, trifluoromethyl, carboxy, (1–4C)alkoxycarbonyl, (3–6C)alkenyloxycarbonyl, cyano, nitro, carbamoyl, (1–4C)alkanoyl, N-alkylcarbamoyl and di-(N-alkyl)carbamoyl of up to 7 carbon atoms, amino, alkylamino and dialkylamino of up to 6 carbon atoms, 3-(1–4C)alkylureido and (1–4C)alkanoylamino; $R^3$ is selected from halogeno, (1–4C)alkoxy, hydroxy, amino, alkylamino and dialkylamino of up to 6 carbon atoms, and any of the values defined for $R^1$; A is a linking group of the formula —CH=CH—CO—, —CO—CH=CH—, —CO—CH$_2$—CH$_2$— or —CH$_2$—CH$_2$—CO—; each of Ra and Rb is independently an indicated hydrogen or an optional substituent on linking group A independently selected from (1–4C)alkyl, substituted (1–4C)alkyl containing one or more fluoro substituents or bearing a (3–8C)cycloalkyl, (1–4C)alkoxy or phenyl substituent, (3–8C)cycloalkyl, phenyl, pyridyl, (1–4C)alkoxy, halogeno, carboxy, (1–4C)alkoxycarbonyl, (3–6C)alkenyloxycarbonyl, carbamoyl, N-alkylcarbamoyl and di-(N-alkyl)carbamoyl of up to 7 carbon atoms, cyano, nitro, (1–4C)alkanoyl, (1–4C)alkylthio, (1–4C)alkylsulphinyl, (1–4C)alkylsulphonyl, phenylthio, phenylsulphinyl or phenylsulphonyl; $R^4$ is selected from hydrogen, (1–4C)alkyl, (1–4C)alkoxy, halogeno, trifluoromethyl, cyano and nitro; X is a direct bond between the adjacent phenyl and methylene groups; Z is 1H-tetrazol-5-yl, —CO.NH.(1H-tetrazol-5-yl), —NHSO$_2$CF$_3$ or a group of the formula —CO.OR$^5$, —CO.NH.SO$_2$.R$^6$ or —SO$_2$.NHR$^7$ in which $R^5$ is hydrogen or a non-toxic, biodegradable residue of a physiologically acceptable alcohol or phenol, $R^6$ is (1–6C)alkyl, (3–8C)cycloalkyl or phenyl, and $R^7$ is hydrogen, (1–4C)alkyl, (1–4C)alkanoyl or —CO.NH.(1–4C)alkyl; or Z is a 2-carboxybenzamido, 2-sulfobenzamido or 2-carboxybenzyloxy group, the benzene ring of which last three groups may optionally bear 1 or 2 additional substituents independently selected from (1–4C)alkyl, (1–4C)alkoxy and halogeno; and wherein any of said phenyl moieties may be unsubstituted or bear one or two substituents independently selected from (1–4C)alkyl, (1–4C)alkoxy, halogeno, cyano and trifluoromethyl; or an N-oxide thereof; or a non-toxic salt thereof.

2. A compound as claimed in claim 1 wherein $R^1$ is hydrogen, methyl, ethyl, propyl, isopropyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl or 2-phenylethyl; $R^2$ is hydrogen, methyl, ethyl, propyl, isopropyl, butyl, methoxy, ethoxy, fluoro, chloro, bromo, iodo, trifluoromethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, carbamoyl, formyl, acetyl, propionyl, N-methylcarbamoyl, N-ethylcarbamoyl, N,N-dimethylcarbamoyl, N,N-diethylcarbamoyl, amino, methylamino, ethylamino, butylamino, dimethylamino, diethylamino, dipropylamino, 3-methylureido, 3-ethylureido, 3-propylureido, formamido, acetamido or propanamido; $R^3$ is selected from hydrogen, methyl, ethyl, propyl, isopropyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl, 2-phenylethyl, fluoro, chloro, bromo, iodo, methoxy, ethoxy, hydroxy, amino, methylamino, ethylamino, butylamino, dimethylamino, diethylamino and dipropylamino; each of Ra and Rb is independently an indicated hydrogen or an optional substituent on linking group A independently selected from methyl, ethyl, propyl, fluoromethyl, trifluoromethyl, 2,2,2-trifluoroethyl and pentafluoroethyl, cyclopropylmethyl, cyclopentylmethyl, cyclohexylmethyl, 2-methoxyethyl, 2-ethoxyethyl, benzyl, 1-phenylethyl, 2-phenylethyl, cyclopropyl, cyclopentyl, cyclohexyl, phenyl, pyridyl, methoxy, ethoxy, fluoro, chloro, bromo, iodo, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, carbamoyl, N-methylcarbamoyl, N-ethylcarbamoyl, N,N-dimethylcarbamoyl, N,N-diethylcarbamoyl, cyano, nitro, formyl, acetyl, propionyl, methylthio, ethylthio, methylsulphinyl, ethylsulphinyl, methylsulphonyl, ethylsulphonyl, phenylthio, phenylsulphinyl and phenylsulphonyl; $R^4$ is selected from hydrogen, methyl, ethyl, methoxy, ethoxy, fluoro, chloro, bromo, iodo, trifluoromethyl, cyano and nitro; Z is 1H-tetrazol-5-yl, —CO.NH.(1H-tetrazol-5-yl), —NHSO$_2$CF$_3$ or a group of the formula —CO.OR$^5$, —CO.NH.SO$_2$.R$^6$ or —SO$_2$.NHR$^7$ in which $R^5$ is hydrogen or a residue derived from a (1-6C)alkanol, or phenol or glycerol, $R^6$ is methyl, ethyl, propyl, isopropyl, butyl, pentyl, cyclobutyl, cyclopentyl, cyclohexyl or phenyl, and $R^7$ is hydrogen, methyl, ethyl, formyl, acetyl, propionyl, —CONHCH$_3$ or —CONHC$_2$H$_5$; or when X is a direct bond between the adjacent phenyl and methylene groups, Z is a 2-carboxybenzamido, 2-sulfobenzamido or 2-carboxybenzyloxy group, the benzene ring of which last three groups may optionally bear 1 or 2 additional substituents independently selected from methyl, ethyl, methoxy, ethoxy, fluoro, chloro and bromo; and wherein any of said phenyl moieties may be unsubstituted or bear one or two substituents independently selected from methyl, ethyl, methoxy, ethoxy, fluoro, chloro, bromo, cyano and trifluoromethyl.

3. A compound as claimed in claim 1 wherein Z is 1H-tetrazol-5-yl, —CO.NH.(1H-tetrazol-5-yl) or a group of the formula —CO.OR$^5$ or —CO.NH.SO$_2$.R$^6$ in which $R^5$ is hydrogen or a non-toxic, biodegradable residue of a physiologically acceptable alcohol or phenol, and $R^6$ is (1-6C)alkyl, (3-8C)cycloalkyl or phenyl; but excluding those compounds wherein one or both of Ra and Rb is selected from pyridyl, carbamoyl, N-alkylcarbamoyl and di-(N-alkyl)carbamoyl of up to 7 carbon atoms, phenylthio and phenylsulphinyl.

4. A compound of the formula Ia

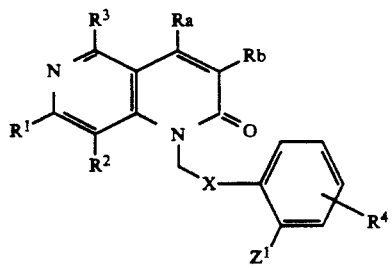

Ia wherein $R^1$, $R^2$, $R^3$, $R^4$, Ra, Rb and X have any of the meanings defined in claim 1, 2 or 3; and $Z^1$ is carboxy or 1H-tetrazol-5-yl; or a non-toxic salt thereof.

5. A compound of the formula Ib

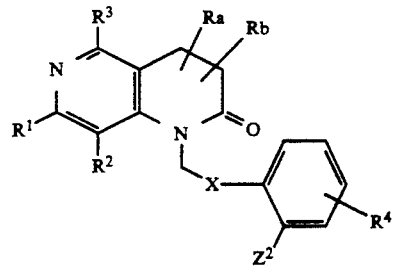

Ib wherein $R^1$, $R^2$, $R^3$, $R^4$, Ra, Rb and X have any of the meanings defined in claim 1, 2 or 3; and $Z^2$ is carboxy or 1H-tetrazol-5-yl; or a non-toxic salt thereof.

6. A salt as claimed in claim 1, 2 or 3 which is selected from salts with acids forming physiologically acceptable anions and, for those compounds of formula I which are acidic, alkali metal, alkaline earth metal, aluminium and ammonium salts, and salts with organic bases affording physiologically acceptable cations.

7. A method for antagonising one or more of the actions of angiotensin II in a warm-blooded animal requiring such treatment which comprises administering to said animal an antagonistically effective amount of a compound of the formula I, or a non-toxic salt thereof, as defined in claim 1.

8. A pharmaceutical composition which comprises a compound of the formula I, Ia or Ib, or a non-toxic salt thereof, as claimed in any of claims 1 to 3, together with a pharmaceutically acceptable diluent or carrier.

9. A compound of the formula III

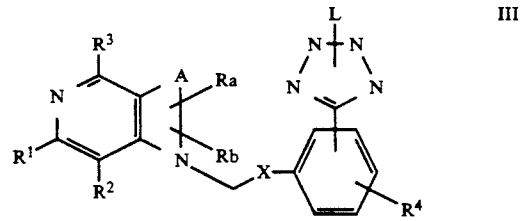

III wherein $R^1$, $R^2$, $R^3$, $R^4$, Ra, Rb, A and X have any of the meanings defined in any of claims 1 to 3, and L is a protecting group.

10. A compound of the formula IX

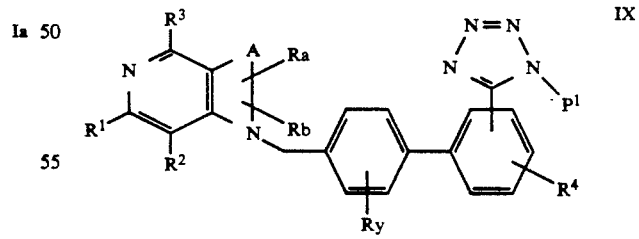

IX wherein $P^1$ is an electron-deficient phenyl group or a pyridyl or pyrimidyl group; Ry is hydrogen, (1-4C)alkyl, (1-4C)alkoxy, halogeno, (1-4C)alkanoyl, trifluoromethyl, cyano or nitro; and $R^1$, $R^2$, $R^3$, $R^4$, Ra, Rb, have any of the meanings defined in any of claims 1 to 3.

* * * * *